（12） United States Patent
Mazlish et al.

(10) Patent No.: US 10,987,468 B2
(45) Date of Patent: Apr. 27, 2021

(54) OPERATING MULTI-MODAL MEDICINE DELIVERY SYSTEMS

(71) Applicant: Bigfoot Biomedical, Inc., Milpitas, CA (US)

(72) Inventors: Bryan Mazlish, Palo Alto, CA (US); Lane Desborough, Thousand Oaks, CA (US)

(73) Assignee: Bigfoot Biomedical, Inc., Milpitas, CA (US)

( * ) Notice: Subject to any disclaimer, the term of this patent is extended or adjusted under 35 U.S.C. 154(b) by 321 days.

(21) Appl. No.: 15/384,493

(22) Filed: Dec. 20, 2016

(65) Prior Publication Data

US 2017/0189614 A1    Jul. 6, 2017

Related U.S. Application Data

(60) Provisional application No. 62/275,213, filed on Jan. 5, 2016.

(51) Int. Cl.
*A61M 5/172*        (2006.01)
*G06F 19/00*        (2018.01)
(Continued)

(52) U.S. Cl.
CPC ........ *A61M 5/1723* (2013.01); *A61M 5/1407* (2013.01); *A61M 5/1452* (2013.01); *A61M 5/14244* (2013.01); *G16H 20/17* (2018.01); *A61M 5/14276* (2013.01); *A61M 2205/3306* (2013.01); *A61M 2205/3553* (2013.01);
(Continued)

(58) Field of Classification Search
CPC .............. A61M 5/1723; A61M 5/1407; A61M 5/14244; A61M 5/1452; A61M 5/14276; A61M 2205/3306; A61M 2205/3553; A61M 2205/3561; A61M 2205/3584; A61M 2205/502; A61M 2205/52; A61M 2205/6009; A61M 2205/702; A61M 2230/7005; A61M 2230/201
See application file for complete search history.

(56) References Cited

U.S. PATENT DOCUMENTS 2,605,765 A    8/1952  Kollsman
3,688,764 A    9/1972  Reed
(Continued)

FOREIGN PATENT DOCUMENTS

CA    2543545 A1    5/2005
CN    1859943 A     11/2006
(Continued)

OTHER PUBLICATIONS

International Primary Report on Patentability in Application No. PCT/US2016/067676, dated Jul. 19, 2018, 9 pages.
(Continued)

*Primary Examiner* — Kami A Bosworth
*Assistant Examiner* — Tezita Z Watts
(74) *Attorney, Agent, or Firm* — TraskBritt

(57) ABSTRACT

A multi-modal medicine delivery system in which some embodiments can be configured to control dispensation of medicine according to any of a plurality of delivery modes, such as by closed-loop delivery modes and open-loop delivery modes, and according to a secondary feedback loop to determine user-specific settings related to dosage delivery.

12 Claims, 15 Drawing Sheets

(51) Int. Cl.
  *A61M 5/14* (2006.01)
  *A61M 5/142* (2006.01)
  *G16H 20/17* (2018.01)
  *A61M 5/145* (2006.01)

(52) U.S. Cl.
  CPC ............... *A61M 2205/3561* (2013.01); *A61M 2205/3584* (2013.01); *A61M 2205/502* (2013.01); *A61M 2205/52* (2013.01); *A61M 2205/6009* (2013.01); *A61M 2205/702* (2013.01); *A61M 2230/005* (2013.01); *A61M 2230/201* (2013.01)

(56) References Cited

U.S. PATENT DOCUMENTS

| | | | |
|---|---|---|---|
| 3,886,938 | A | 6/1975 | Szabo et al. |
| 4,077,405 | A | 3/1978 | Haerten et al. |
| 4,151,845 | A | 5/1979 | Clemens |
| 4,231,368 | A | 11/1980 | Becker |
| 4,235,234 | A | 11/1980 | Martin et al. |
| 4,265,241 | A | 5/1981 | Portner et al. |
| 4,300,554 | A | 11/1981 | Hessberg et al. |
| 4,313,439 | A | 2/1982 | Babb et al. |
| 4,373,527 | A | 2/1983 | Fischell |
| 4,398,908 | A | 8/1983 | Siposs |
| 4,435,173 | A | 3/1984 | Siposs et al. |
| 4,443,218 | A | 4/1984 | Decant et al. |
| 4,475,901 | A | 10/1984 | Kraegen et al. |
| 4,493,704 | A | 1/1985 | Beard et al. |
| 4,529,401 | A | 7/1985 | Leslie et al. |
| 4,552,561 | A | 11/1985 | Eckenhoff et al. |
| 4,564,054 | A | 1/1986 | Gustavsson |
| 4,652,260 | A | 3/1987 | Fenton et al. |
| 4,668,220 | A | 5/1987 | Hawrylenko |
| 4,681,569 | A | 7/1987 | Coble et al. |
| 4,731,726 | A | 3/1988 | Allen, III |
| 4,734,092 | A | 3/1988 | Millerd |
| 4,749,109 | A | 6/1988 | Kamen |
| 4,768,506 | A | 9/1988 | Parker et al. |
| 4,838,857 | A | 6/1989 | Strowe et al. |
| 4,850,817 | A | 7/1989 | Mason et al. |
| 4,902,278 | A | 2/1990 | Maget et al. |
| 5,029,591 | A | 7/1991 | Teves |
| 5,045,064 | A | 9/1991 | Idriss |
| 5,088,981 | A | 2/1992 | Howson et al. |
| 5,088,990 | A | 2/1992 | Hivale et al. |
| 5,176,632 | A | 1/1993 | Bernardi |
| 5,190,522 | A | 3/1993 | Wojcicki et al. |
| 5,209,230 | A | 5/1993 | Swedlow et al. |
| 5,225,763 | A | 7/1993 | Krohn et al. |
| 5,250,027 | A | 10/1993 | Lewis et al. |
| 5,261,882 | A | 11/1993 | Sealfon |
| 5,314,412 | A | 5/1994 | Rex |
| 5,335,994 | A | 8/1994 | Weynant |
| 5,338,157 | A | 8/1994 | Blomquist |
| 5,342,180 | A | 8/1994 | Daoud |
| 5,349,575 | A | 9/1994 | Park |
| 5,389,078 | A | 2/1995 | Zalesky et al. |
| 5,395,340 | A | 3/1995 | Lee |
| 5,411,487 | A | 5/1995 | Castagna |
| 5,527,288 | A | 6/1996 | Gross et al. |
| 5,545,143 | A | 8/1996 | Fischell et al. |
| 5,551,850 | A | 9/1996 | Williamson et al. |
| 5,554,123 | A | 9/1996 | Herskowitz |
| 5,569,186 | A | 10/1996 | Lord et al. |
| 5,626,566 | A | 5/1997 | Petersen et al. |
| 5,637,095 | A | 6/1997 | Nason et al. |
| 5,656,032 | A | 8/1997 | Kriesel et al. |
| 5,665,065 | A | 9/1997 | Colman et al. |
| 5,672,167 | A | 9/1997 | Athayde et al. |
| 5,693,018 | A | 12/1997 | Kriesel et al. |
| 5,718,562 | A | 2/1998 | Lawless et al. |
| 5,741,216 | A | 4/1998 | Hemmingsen et al. |
| 5,766,155 | A | 6/1998 | Hyman et al. |
| 5,772,635 | A | 6/1998 | Dastur et al. |
| 5,800,420 | A | 9/1998 | Gross et al. |
| 5,816,306 | A | 10/1998 | Giacomel |
| 5,822,715 | A | 10/1998 | Worthington et al. |
| 5,851,197 | A | 12/1998 | Marano et al. |
| 5,852,803 | A | 12/1998 | Ashby et al. |
| 5,858,001 | A | 1/1999 | Tsals et al. |
| 5,858,005 | A | 1/1999 | Kriesel |
| 5,873,731 | A | 2/1999 | Prendergast |
| 5,893,838 | A | 4/1999 | Daoud et al. |
| 5,914,941 | A | 6/1999 | Janky |
| 5,919,167 | A | 7/1999 | Mulhauser et al. |
| 5,925,018 | A | 7/1999 | Ungerstedt |
| 5,928,201 | A | 7/1999 | Poulsen et al. |
| 5,947,934 | A | 9/1999 | Hansen et al. |
| 5,951,530 | A | 9/1999 | Steengaard et al. |
| 5,957,889 | A | 9/1999 | Poulsen et al. |
| 5,984,894 | A | 11/1999 | Poulsen et al. |
| 5,984,897 | A | 11/1999 | Petersen et al. |
| 5,997,475 | A | 12/1999 | Bortz |
| 6,003,736 | A | 12/1999 | Ljunggren |
| 6,010,485 | A | 1/2000 | Buch-Rasmussen et al. |
| 6,033,377 | A | 3/2000 | Rasmussen et al. |
| 6,045,537 | A | 4/2000 | Klitmose |
| 6,056,728 | A | 5/2000 | Von Schuckmann |
| 6,074,372 | A | 6/2000 | Hansen |
| 6,106,498 | A | 8/2000 | Friedli et al. |
| 6,110,149 | A | 8/2000 | Klitgaard et al. |
| 6,126,595 | A | 10/2000 | Amano et al. |
| 6,127,061 | A | 10/2000 | Shun et al. |
| 6,156,014 | A | 12/2000 | Petersen et al. |
| 6,171,276 | B1 | 1/2001 | Lippe et al. |
| 6,231,540 | B1 | 5/2001 | Smedegaard |
| 6,233,471 | B1 | 5/2001 | Berner et al. |
| 6,248,067 | B1 | 6/2001 | Causey et al. |
| 6,248,090 | B1 | 6/2001 | Jensen et al. |
| 6,248,093 | B1 | 6/2001 | Moberg |
| 6,251,113 | B1 | 6/2001 | Appelbaum et al. |
| 6,269,340 | B1 | 7/2001 | Ford et al. |
| 6,277,098 | B1 | 8/2001 | Klitmose et al. |
| 6,292,440 | B1 | 9/2001 | Lee |
| 6,302,855 | B1 | 10/2001 | Lav et al. |
| 6,302,869 | B1 | 10/2001 | Klitgaard |
| 6,368,314 | B1 | 4/2002 | Kipfer et al. |
| 6,375,638 | B2 | 4/2002 | Nason et al. |
| 6,379,301 | B1 | 4/2002 | Worthington et al. |
| 6,379,339 | B1 | 4/2002 | Klitgaard et al. |
| 6,381,496 | B1 | 4/2002 | Meadows et al. |
| 6,397,098 | B1 | 5/2002 | Liber et al. |
| 6,404,098 | B1 | 6/2002 | Kayama et al. |
| 6,427,088 | B1 | 7/2002 | Bowman et al. |
| D461,241 | S | 8/2002 | Moberg |
| D461,891 | S | 8/2002 | Moberg |
| 6,434,528 | B1 | 8/2002 | Sanders |
| 6,436,072 | B1 | 8/2002 | Kullas et al. |
| 6,461,329 | B1 | 10/2002 | Van et al. |
| 6,461,331 | B1 | 10/2002 | Van Antwerp |
| 6,474,219 | B2 | 11/2002 | Klitmose et al. |
| 6,485,461 | B1 | 11/2002 | Mason et al. |
| 6,491,684 | B1 | 12/2002 | Joshi et al. |
| 6,508,788 | B2 | 1/2003 | Preuthun |
| 6,524,280 | B2 | 2/2003 | Hansen et al. |
| 6,533,183 | B2 | 3/2003 | Aasmul et al. |
| 6,537,251 | B2 | 3/2003 | Klitmose |
| 6,537,268 | B1 | 3/2003 | Gibson et al. |
| 6,540,672 | B1 | 4/2003 | Simonsen et al. |
| 6,544,212 | B2 | 4/2003 | Galley et al. |
| 6,544,229 | B1 | 4/2003 | Danby et al. |
| 6,547,764 | B2 | 4/2003 | Larsen et al. |
| 6,551,276 | B1 | 4/2003 | Mann et al. |
| 6,554,798 | B1 | 4/2003 | Mann et al. |
| 6,554,800 | B1 | 4/2003 | Nezhadian et al. |
| 6,558,320 | B1 | 5/2003 | Causey et al. |
| 6,558,345 | B1 | 5/2003 | Houben et al. |
| 6,558,351 | B1 | 5/2003 | Steil et al. |
| 6,562,001 | B2 | 5/2003 | Lebel et al. |
| 6,562,011 | B1 | 5/2003 | Buch-Rasmussen et al. |
| 6,564,105 | B2 | 5/2003 | Starkweather et al. |
| 6,569,126 | B1 | 5/2003 | Poulsen et al. |

(56) References Cited

U.S. PATENT DOCUMENTS

| | | |
|---|---|---|
| 6,571,128 B2 | 5/2003 | Lebel et al. |
| 6,572,542 B1 | 6/2003 | Houben et al. |
| 6,572,545 B2 | 6/2003 | Knobbe et al. |
| 6,577,899 B2 | 6/2003 | Lebel et al. |
| 6,582,404 B1 | 6/2003 | Klitgaard et al. |
| 6,585,644 B2 | 7/2003 | Lebel et al. |
| 6,585,699 B2 | 7/2003 | Ljunggreen et al. |
| 6,587,199 B1 | 7/2003 | Luu |
| 6,589,229 B1 | 7/2003 | Connelly et al. |
| 6,599,281 B1 | 7/2003 | Struys et al. |
| 6,605,067 B1 | 8/2003 | Larsen |
| 6,605,072 B2 | 8/2003 | Struys et al. |
| 6,613,019 B2 | 9/2003 | Munk |
| 6,641,533 B2 | 11/2003 | Causey et al. |
| 6,648,821 B2 | 11/2003 | Lebel et al. |
| 6,650,951 B1 | 11/2003 | Jones et al. |
| 6,656,158 B2 | 12/2003 | Mahoney et al. |
| 6,656,159 B2 | 12/2003 | Flaherty |
| 6,659,948 B2 | 12/2003 | Lebel et al. |
| 6,659,978 B1 | 12/2003 | Kasuga et al. |
| 6,659,980 B2 | 12/2003 | Moberg et al. |
| 6,663,602 B2 | 12/2003 | Moeller |
| 6,668,196 B1 | 12/2003 | Villegas et al. |
| 6,669,668 B1 | 12/2003 | Kleeman et al. |
| 6,669,669 B2 | 12/2003 | Flaherty et al. |
| 6,685,674 B2 | 2/2004 | Douglas et al. |
| 6,687,546 B2 | 2/2004 | Lebel et al. |
| 6,689,100 B2 | 2/2004 | Connelly et al. |
| 6,690,192 B1 | 2/2004 | Wing |
| 6,691,043 B2 | 2/2004 | Ribeiro, Jr. |
| 6,692,457 B2 | 2/2004 | Flaherty |
| 6,692,472 B2 | 2/2004 | Hansen et al. |
| 6,694,191 B2 | 2/2004 | Starkweather et al. |
| 6,699,218 B2 | 3/2004 | Flaherty et al. |
| 6,702,779 B2 | 3/2004 | Connelly et al. |
| 6,715,516 B2 | 4/2004 | Ohms et al. |
| 6,716,198 B2 | 4/2004 | Larsen |
| 6,723,072 B2 | 4/2004 | Flaherty et al. |
| 6,723,077 B2 | 4/2004 | Pickup et al. |
| 6,733,446 B2 | 5/2004 | Lebel et al. |
| 6,736,796 B2 | 5/2004 | Shekalim |
| 6,740,059 B2 | 5/2004 | Flaherty |
| 6,740,072 B2 | 5/2004 | Starkweather et al. |
| 6,740,075 B2 | 5/2004 | Lebel et al. |
| 6,744,350 B2 | 6/2004 | Blomquist |
| 6,749,587 B2 | 6/2004 | Flaherty |
| 6,752,785 B2 | 6/2004 | Van et al. |
| 6,752,787 B1 | 6/2004 | Causey et al. |
| 6,758,810 B2 | 7/2004 | Lebel et al. |
| 6,761,286 B2 | 7/2004 | Py et al. |
| 6,768,425 B2 | 7/2004 | Flaherty et al. |
| 6,780,156 B2 | 8/2004 | Haueter et al. |
| 6,786,246 B2 | 9/2004 | Ohms et al. |
| 6,786,890 B2 | 9/2004 | Preuthun et al. |
| 6,796,957 B2 | 9/2004 | Carpenter et al. |
| 6,796,970 B1 | 9/2004 | Klitmose et al. |
| 6,799,149 B2 | 9/2004 | Hartlaub |
| 6,809,653 B1 | 10/2004 | Mann et al. |
| 6,810,290 B2 | 10/2004 | Lebel et al. |
| 6,811,533 B2 | 11/2004 | Lebel et al. |
| 6,811,534 B2 | 11/2004 | Bowman et al. |
| 6,813,519 B2 | 11/2004 | Lebel et al. |
| 6,827,702 B2 | 12/2004 | Lebel et al. |
| 6,830,558 B2 | 12/2004 | Flaherty et al. |
| 6,852,104 B2 | 2/2005 | Blomquist |
| 6,854,620 B2 | 2/2005 | Ramey |
| 6,854,653 B2 | 2/2005 | Eilersen |
| 6,855,129 B2 | 2/2005 | Jensen et al. |
| 6,872,200 B2 | 3/2005 | Mann et al. |
| 6,873,268 B2 | 3/2005 | Lebel et al. |
| 6,878,132 B2 | 4/2005 | Kipfer |
| 6,893,415 B2 | 5/2005 | Madsen et al. |
| 6,899,695 B2 | 5/2005 | Herrera |
| 6,899,699 B2 | 5/2005 | Enggaard |
| 6,922,590 B1 | 7/2005 | Whitehurst |
| 6,923,763 B1 | 8/2005 | Kovatchev et al. |
| 6,925,393 B1 | 8/2005 | Kalatz et al. |
| 6,936,006 B2 | 8/2005 | Sabra |
| 6,936,029 B2 | 8/2005 | Mann et al. |
| 6,945,961 B2 | 9/2005 | Miller et al. |
| 6,948,918 B2 | 9/2005 | Hansen |
| 6,950,708 B2 | 9/2005 | Bowman et al. |
| 6,960,192 B1 | 11/2005 | Flaherty et al. |
| 6,979,326 B2 | 12/2005 | Mann et al. |
| 6,997,911 B2 | 2/2006 | Klitmose |
| 6,997,920 B2 | 2/2006 | Mann et al. |
| 7,005,078 B2 | 2/2006 | Van et al. |
| 7,008,399 B2 | 3/2006 | Larsen et al. |
| 7,014,625 B2 | 3/2006 | Bengtsson |
| 7,018,360 B2 | 3/2006 | Flaherty et al. |
| 7,025,743 B2 | 4/2006 | Mann et al. |
| 7,029,455 B2 | 4/2006 | Flaherty |
| 7,054,836 B2 | 5/2006 | Christensen et al. |
| 7,060,059 B2 | 6/2006 | Keith et al. |
| 7,066,910 B2 | 6/2006 | Bauhahn et al. |
| 7,070,580 B2 | 7/2006 | Nielsen |
| 7,098,803 B2 | 8/2006 | Mann et al. |
| 7,104,972 B2 | 9/2006 | Moller et al. |
| 7,109,878 B2 | 9/2006 | Mann et al. |
| 7,123,964 B2 | 10/2006 | Betzold et al. |
| 7,128,727 B2 | 10/2006 | Flaherty et al. |
| 7,133,329 B2 | 11/2006 | Skyggebjerg et al. |
| 7,172,572 B2 | 2/2007 | Diamond et al. |
| 7,179,226 B2 | 2/2007 | Crothall et al. |
| 7,204,823 B2 | 4/2007 | Estes et al. |
| 7,220,240 B2 | 5/2007 | Struys et al. |
| 7,232,423 B2 | 6/2007 | Mernoee |
| 7,267,665 B2 | 9/2007 | Steil et al. |
| 7,278,983 B2 | 10/2007 | Ireland et al. |
| 7,291,107 B2 | 11/2007 | Hellwig et al. |
| 7,354,420 B2 | 4/2008 | Steil et al. |
| 7,402,153 B2 | 7/2008 | Steil et al. |
| 7,404,796 B2 | 7/2008 | Ginsberg |
| 7,429,255 B2 | 9/2008 | Thompson |
| 7,455,663 B2 | 11/2008 | Bikovsky |
| 7,491,187 B2 | 2/2009 | Van Den Berghe et al. |
| 7,494,481 B2 | 2/2009 | Moberg et al. |
| 7,534,226 B2 | 5/2009 | Mernoe et al. |
| 7,547,281 B2 | 6/2009 | Hayes et al. |
| 7,553,281 B2 | 6/2009 | Hellwig et al. |
| 7,569,030 B2 | 8/2009 | Lebel et al. |
| 7,569,050 B2 | 8/2009 | Moberg et al. |
| 7,570,980 B2 | 8/2009 | Ginsberg |
| 7,591,801 B2 | 9/2009 | Brauker et al. |
| 7,597,682 B2 | 10/2009 | Moberg |
| 7,641,649 B2 | 1/2010 | Moberg et al. |
| 7,651,845 B2 | 1/2010 | Doyle et al. |
| 7,654,982 B2 | 2/2010 | Carlisle et al. |
| 7,670,288 B2 | 3/2010 | Sher |
| 7,704,226 B2 | 4/2010 | Mueller, Jr. et al. |
| 7,708,717 B2 | 5/2010 | Estes et al. |
| 7,734,323 B2 | 6/2010 | Blomquist et al. |
| 7,785,313 B2 | 8/2010 | Mastrototaro |
| 7,789,859 B2 | 9/2010 | Estes et al. |
| 7,794,426 B2 | 9/2010 | Briones et al. |
| 7,806,853 B2 | 10/2010 | Wittmann et al. |
| 7,806,854 B2 | 10/2010 | Damiano et al. |
| 7,806,886 B2 | 10/2010 | Kanderian et al. |
| 7,815,602 B2 | 10/2010 | Mann et al. |
| 7,819,843 B2 | 10/2010 | Mann et al. |
| 7,828,528 B2 | 11/2010 | Estes et al. |
| 7,833,196 B2 | 11/2010 | Estes et al. |
| 7,850,641 B2 | 12/2010 | Lebel et al. |
| 7,875,022 B2 | 1/2011 | Wenger et al. |
| 7,879,026 B2 | 2/2011 | Estes et al. |
| 7,892,199 B2 | 2/2011 | Mhatre et al. |
| 7,904,061 B1 | 3/2011 | Zaffino et al. |
| 7,938,797 B2 | 5/2011 | Estes |
| 7,938,801 B2 | 5/2011 | Hawkins et al. |
| 7,946,985 B2 | 5/2011 | Mastrototaro et al. |
| 7,959,598 B2 | 6/2011 | Estes |
| 7,967,812 B2 | 6/2011 | Jasperson et al. |
| 7,976,492 B2 | 7/2011 | Brauker et al. |
| 8,029,459 B2 | 10/2011 | Rush et al. |

(56) References Cited

U.S. PATENT DOCUMENTS

| | | |
|---|---|---|
| 8,057,436 B2 | 11/2011 | Causey et al. |
| 8,062,249 B2 | 11/2011 | Wilinska et al. |
| 8,088,098 B2 | 1/2012 | Yodfat et al. |
| 8,105,268 B2 | 1/2012 | Lebel et al. |
| 8,114,023 B2 | 2/2012 | Ward et al. |
| 8,152,789 B2 | 4/2012 | Starkweather et al. |
| 8,206,296 B2 | 6/2012 | Jennewine |
| 8,206,350 B2 | 6/2012 | Mann et al. |
| 8,208,984 B2 | 6/2012 | Blomquist et al. |
| 8,221,385 B2 | 7/2012 | Estes |
| 8,226,556 B2 | 7/2012 | Hayes et al. |
| 8,246,540 B2 | 8/2012 | Ginsberg |
| 8,257,300 B2 | 9/2012 | Budiman et al. |
| 8,262,616 B2 | 9/2012 | Grant et al. |
| 8,267,893 B2 | 9/2012 | Moberg et al. |
| 8,273,052 B2 | 9/2012 | Damiano et al. |
| D669,165 S | 10/2012 | Sims et al. |
| 8,282,626 B2 | 10/2012 | Wenger et al. |
| 8,287,487 B2 | 10/2012 | Estes |
| 8,318,154 B2 | 11/2012 | Frost et al. |
| 8,348,844 B2 | 1/2013 | Kunjan et al. |
| 8,348,886 B2 | 1/2013 | Kanderian et al. |
| 8,348,923 B2 | 1/2013 | Kanderian et al. |
| 8,352,011 B2 | 1/2013 | Van Antwerp et al. |
| 8,372,039 B2 | 2/2013 | Mernoe et al. |
| 8,409,142 B2 | 4/2013 | Causey et al. |
| 8,417,311 B2 | 4/2013 | Rule |
| 8,430,847 B2 | 4/2013 | Mernoe et al. |
| 8,439,834 B2 | 5/2013 | Schmelzeisen-Redeker et al. |
| 8,439,897 B2 | 5/2013 | Yodfat et al. |
| 8,454,576 B2 | 6/2013 | Mastrototaro et al. |
| 8,460,231 B2 | 6/2013 | Brauker et al. |
| 8,467,972 B2 | 6/2013 | Rush |
| 8,475,408 B2 | 7/2013 | Mernoe et al. |
| 8,475,409 B2 | 7/2013 | Tsoukalis |
| 8,480,655 B2 | 7/2013 | Jasperson et al. |
| 8,548,544 B2 | 10/2013 | Kircher, Jr. et al. |
| 8,548,552 B2 | 10/2013 | Tsoukalis |
| 8,551,045 B2 | 10/2013 | Sie et al. |
| 8,560,082 B2 | 10/2013 | Wei |
| 8,560,131 B2 | 10/2013 | Haueter et al. |
| 8,562,558 B2 | 10/2013 | Kamath et al. |
| 8,562,587 B2 | 10/2013 | Kovatchev et al. |
| 8,568,713 B2 | 10/2013 | Frost et al. |
| 8,579,854 B2 | 11/2013 | Budiman et al. |
| 8,579,879 B2 | 11/2013 | Palem et al. |
| 8,585,591 B2 | 11/2013 | Sloan |
| 8,585,593 B2 | 11/2013 | Kovatchev et al. |
| 8,585,637 B2 | 11/2013 | Wilinska et al. |
| 8,585,638 B2 | 11/2013 | Blomquist |
| 8,597,274 B2 | 12/2013 | Sloan et al. |
| 8,615,366 B2 | 12/2013 | Galley et al. |
| 8,622,988 B2 | 1/2014 | Hayter |
| 8,679,016 B2 | 3/2014 | Mastrototaro et al. |
| 8,679,060 B2 | 3/2014 | Mernoe et al. |
| 8,690,820 B2 | 4/2014 | Cinar et al. |
| 8,694,115 B2 | 4/2014 | Goetz et al. |
| 8,706,691 B2 | 4/2014 | McDaniel et al. |
| 8,718,949 B2 | 5/2014 | Blomquist et al. |
| 8,721,585 B2 | 5/2014 | Brauker et al. |
| 8,727,982 B2 | 5/2014 | Jennewine |
| 8,734,422 B2 | 5/2014 | Hayter |
| 8,734,428 B2 | 5/2014 | Blomquist |
| 8,747,315 B2 | 6/2014 | Brauker et al. |
| 8,762,070 B2 | 6/2014 | Doyle et al. |
| 8,771,222 B2 | 7/2014 | Kanderian et al. |
| 8,777,896 B2 | 7/2014 | Starkweather et al. |
| 8,777,924 B2 | 7/2014 | Kanderian et al. |
| 8,784,364 B2 | 7/2014 | Kamen et al. |
| 8,784,369 B2 | 7/2014 | Starkweather et al. |
| 8,784,370 B2 | 7/2014 | Lebel et al. |
| 8,795,224 B2 | 8/2014 | Starkweather et al. |
| 8,795,252 B2 | 8/2014 | Hayter |
| 8,808,230 B2 | 8/2014 | Rotstein |
| 8,876,755 B2 | 11/2014 | Taub et al. |
| 8,882,741 B2 | 11/2014 | Brauker et al. |
| 8,903,501 B2 | 12/2014 | Perryman |
| 8,919,180 B2 | 12/2014 | Gottlieb et al. |
| 8,920,401 B2 | 12/2014 | Brauker et al. |
| 8,926,585 B2 | 1/2015 | Brauker et al. |
| 8,945,094 B2 | 2/2015 | Nordh |
| 8,956,291 B2 | 2/2015 | Valk et al. |
| 8,956,321 B2 | 2/2015 | Dejournett |
| 8,977,504 B2 | 3/2015 | Hovorka |
| 8,992,475 B2 | 3/2015 | Mann et al. |
| 9,034,323 B2 | 5/2015 | Frost et al. |
| 9,050,413 B2 | 6/2015 | Brauker et al. |
| 9,056,165 B2 | 6/2015 | Steil et al. |
| 9,056,168 B2 | 6/2015 | Kircher et al. |
| 9,078,963 B2 | 7/2015 | Estes |
| 9,089,305 B2 | 7/2015 | Hovorka |
| 9,149,233 B2 | 10/2015 | Kamath et al. |
| 9,155,843 B2 | 10/2015 | Brauker et al. |
| 9,247,901 B2 | 2/2016 | Kamath et al. |
| 9,314,566 B2 | 4/2016 | Wenger et al. |
| 9,320,471 B2 | 4/2016 | Hayes et al. |
| 9,333,298 B2 | 5/2016 | Kim et al. |
| 9,415,157 B2 | 8/2016 | Mann et al. |
| 9,474,855 B2 | 10/2016 | McCann et al. |
| 9,480,796 B2 | 11/2016 | Starkweather et al. |
| 9,486,172 B2 | 11/2016 | Cobelli et al. |
| 9,486,578 B2 | 11/2016 | Finan et al. |
| 9,561,324 B2 | 2/2017 | Estes |
| 9,878,097 B2 | 1/2018 | Estes |
| 9,968,729 B2 | 5/2018 | Estes |
| 10,449,294 B1 | 10/2019 | Estes |
| 10,569,015 B2 | 2/2020 | Estes |
| 2001/0003542 A1 | 6/2001 | Kita |
| 2001/0041869 A1 | 11/2001 | Causey et al. |
| 2001/0056262 A1 | 12/2001 | Cabiri et al. |
| 2002/0002326 A1 | 1/2002 | Causey et al. |
| 2002/0004651 A1 | 1/2002 | Ljunggreen et al. |
| 2002/0007154 A1 | 1/2002 | Hansen et al. |
| 2002/0013784 A1 | 1/2002 | Swanson |
| 2002/0016534 A1 | 2/2002 | Trepagnier et al. |
| 2002/0016568 A1 | 2/2002 | Lebel et al. |
| 2002/0032402 A1 | 3/2002 | Daoud |
| 2002/0040208 A1 | 4/2002 | Flaherty et al. |
| 2002/0046315 A1 | 4/2002 | Miller et al. |
| 2002/0055845 A1 | 5/2002 | Ueda et al. |
| 2002/0072720 A1 | 6/2002 | Hague et al. |
| 2002/0091358 A1 | 7/2002 | Klitmose |
| 2002/0107476 A1 | 8/2002 | Mann et al. |
| 2002/0126036 A1 | 9/2002 | Flaherty et al. |
| 2002/0133113 A1 | 9/2002 | Madsen et al. |
| 2002/0156462 A1 | 10/2002 | Stultz |
| 2002/0164973 A1 | 11/2002 | Janik et al. |
| 2002/0169439 A1 | 11/2002 | Flaherty |
| 2003/0028089 A1 | 2/2003 | Galley et al. |
| 2003/0055380 A1 | 3/2003 | Flaherty |
| 2003/0060753 A1 | 3/2003 | Starkweather et al. |
| 2003/0065308 A1 | 4/2003 | Lebel et al. |
| 2003/0088238 A1 | 5/2003 | Poulsen et al. |
| 2003/0104982 A1 | 6/2003 | Wittmann et al. |
| 2003/0114836 A1 | 6/2003 | Estes et al. |
| 2003/0121055 A1 | 6/2003 | Kaminski et al. |
| 2003/0125672 A1 | 7/2003 | Adair et al. |
| 2003/0130616 A1 | 7/2003 | Steil et al. |
| 2003/0161744 A1 | 8/2003 | Vilks et al. |
| 2003/0167035 A1 | 9/2003 | Flaherty et al. |
| 2003/0181852 A1 | 9/2003 | Mann et al. |
| 2003/0187525 A1 | 10/2003 | Mann et al. |
| 2003/0191431 A1 | 10/2003 | Mann et al. |
| 2003/0195462 A1 | 10/2003 | Mann et al. |
| 2003/0198558 A1 | 10/2003 | Nason et al. |
| 2003/0199825 A1 | 10/2003 | Flaherty |
| 2003/0208113 A1 | 11/2003 | Mault et al. |
| 2003/0212364 A1 | 11/2003 | Mann et al. |
| 2003/0216683 A1 | 11/2003 | Shekalim |
| 2003/0216686 A1 | 11/2003 | Lynch et al. |
| 2003/0236498 A1 | 12/2003 | Gross et al. |
| 2004/0006316 A1 | 1/2004 | Patton |
| 2004/0010207 A1 | 1/2004 | Flaherty et al. |
| 2004/0019325 A1 | 1/2004 | Shekalim |

(56) References Cited

U.S. PATENT DOCUMENTS

| | | |
|---|---|---|
| 2004/0064088 A1 | 4/2004 | Gorman et al. |
| 2004/0064096 A1 | 4/2004 | Flaherty et al. |
| 2004/0068230 A1 | 4/2004 | Estes et al. |
| 2004/0078028 A1 | 4/2004 | Flaherty et al. |
| 2004/0087894 A1 | 5/2004 | Flaherty |
| 2004/0092865 A1 | 5/2004 | Flaherty et al. |
| 2004/0092878 A1 | 5/2004 | Flaherty |
| 2004/0115068 A1 | 6/2004 | Hansen et al. |
| 2004/0116866 A1 | 6/2004 | Gorman et al. |
| 2004/0127844 A1 | 7/2004 | Flaherty |
| 2004/0153032 A1 | 8/2004 | Garribotto et al. |
| 2004/0158207 A1 | 8/2004 | Nunn et al. |
| 2004/0167464 A1 | 8/2004 | Ireland et al. |
| 2004/0171983 A1 | 9/2004 | Sparks et al. |
| 2004/0176720 A1 | 9/2004 | Kipfer |
| 2004/0176727 A1 | 9/2004 | Shekalim |
| 2004/0187952 A1 | 9/2004 | Jones |
| 2004/0193025 A1 | 9/2004 | Steil et al. |
| 2004/0204673 A1 | 10/2004 | Flaherty |
| 2004/0204744 A1 | 10/2004 | Penner et al. |
| 2004/0220517 A1 | 11/2004 | Starkweather et al. |
| 2004/0220551 A1 | 11/2004 | Flaherty et al. |
| 2004/0235446 A1 | 11/2004 | Flaherty et al. |
| 2004/0260233 A1 | 12/2004 | Garibotto et al. |
| 2005/0010165 A1 | 1/2005 | Hickle |
| 2005/0021005 A1 | 1/2005 | Flaherty et al. |
| 2005/0021104 A1 | 1/2005 | Dilorenzo |
| 2005/0022274 A1 | 1/2005 | Campbell et al. |
| 2005/0033223 A1 | 2/2005 | Herrera |
| 2005/0038332 A1 | 2/2005 | Saidara et al. |
| 2005/0049179 A1 | 3/2005 | Davidson et al. |
| 2005/0065465 A1 | 3/2005 | Lebel et al. |
| 2005/0065760 A1 | 3/2005 | Murtfeldt et al. |
| 2005/0090808 A1 | 4/2005 | Malave et al. |
| 2005/0090851 A1 | 4/2005 | Devlin |
| 2005/0095063 A1 | 5/2005 | Fathallah et al. |
| 2005/0101933 A1 | 5/2005 | Marrs et al. |
| 2005/0107743 A1 | 5/2005 | Fangrow, Jr. |
| 2005/0113745 A1 | 5/2005 | Stultz |
| 2005/0124866 A1 | 6/2005 | Elaz et al. |
| 2005/0137530 A1 | 6/2005 | Campbell et al. |
| 2005/0160858 A1 | 7/2005 | Mernoe |
| 2005/0171512 A1 | 8/2005 | Flaherty |
| 2005/0171513 A1 | 8/2005 | Mann et al. |
| 2005/0182366 A1 | 8/2005 | Vogt et al. |
| 2005/0192561 A1 | 9/2005 | Mernoe |
| 2005/0203461 A1 | 9/2005 | Flaherty et al. |
| 2005/0215982 A1 | 9/2005 | Malave et al. |
| 2005/0222645 A1 | 10/2005 | Malave et al. |
| 2005/0234404 A1 | 10/2005 | Vilks et al. |
| 2005/0238507 A1 | 10/2005 | Diianni et al. |
| 2005/0240544 A1 | 10/2005 | Kil et al. |
| 2005/0245878 A1 | 11/2005 | Mernoe et al. |
| 2005/0251097 A1 | 11/2005 | Mernoe |
| 2005/0267402 A1 | 12/2005 | Stewart et al. |
| 2005/0273059 A1 | 12/2005 | Mernoe et al. |
| 2005/0277890 A1 | 12/2005 | Stewart et al. |
| 2006/0036214 A1 | 2/2006 | Mogensen et al. |
| 2006/0041229 A1 | 2/2006 | Garibotto et al. |
| 2006/0042633 A1 | 3/2006 | Bishop et al. |
| 2006/0069351 A9 | 3/2006 | Safabash et al. |
| 2006/0069382 A1 | 3/2006 | Pedersen |
| 2006/0074381 A1 | 4/2006 | Malave et al. |
| 2006/0075269 A1 | 4/2006 | Liong et al. |
| 2006/0095014 A1 | 5/2006 | Ethelfeld |
| 2006/0125654 A1 | 6/2006 | Liao |
| 2006/0135913 A1 | 6/2006 | Ethelfeld |
| 2006/0142698 A1 | 6/2006 | Ethelfeld |
| 2006/0151545 A1 | 7/2006 | Imhof et al. |
| 2006/0173406 A1 | 8/2006 | Hayes et al. |
| 2006/0173410 A1 | 8/2006 | Moberg et al. |
| 2006/0178633 A1 | 8/2006 | Garibotto et al. |
| 2006/0184104 A1 | 8/2006 | Cheney et al. |
| 2006/0184119 A1 | 8/2006 | Remde et al. |
| 2006/0200073 A1 | 9/2006 | Radmer et al. |
| 2006/0206054 A1 | 9/2006 | Shekalim |
| 2006/0214511 A1 | 9/2006 | Dayan |
| 2006/0224109 A1 | 10/2006 | Steil et al. |
| 2006/0247574 A1 | 11/2006 | Maule et al. |
| 2006/0247581 A1 | 11/2006 | Pedersen et al. |
| 2006/0253086 A1 | 11/2006 | Moberg et al. |
| 2006/0258973 A1 | 11/2006 | Volt |
| 2006/0258976 A1 | 11/2006 | Shturman et al. |
| 2006/0264835 A1 | 11/2006 | Nielsen et al. |
| 2006/0264889 A1 | 11/2006 | Moberg et al. |
| 2006/0264890 A1 | 11/2006 | Moberg et al. |
| 2006/0264894 A1 | 11/2006 | Moberg et al. |
| 2007/0016127 A1 | 1/2007 | Staib et al. |
| 2007/0060870 A1 | 3/2007 | Tolle et al. |
| 2007/0073228 A1 | 3/2007 | Mernoe et al. |
| 2007/0073235 A1 | 3/2007 | Estes et al. |
| 2007/0073236 A1 | 3/2007 | Mernoe et al. |
| 2007/0078818 A1 | 4/2007 | Zivitz et al. |
| 2007/0079836 A1 | 4/2007 | Reghabi et al. |
| 2007/0088271 A1 | 4/2007 | Richards |
| 2007/0093750 A1 | 4/2007 | Jan et al. |
| 2007/0093786 A1 | 4/2007 | Goldsmith et al. |
| 2007/0100222 A1 | 5/2007 | Mastrototaro et al. |
| 2007/0106218 A1 | 5/2007 | Yodfat et al. |
| 2007/0112298 A1 | 5/2007 | Mueller et al. |
| 2007/0118364 A1 | 5/2007 | Wise et al. |
| 2007/0118405 A1 | 5/2007 | Campbell et al. |
| 2007/0123819 A1 | 5/2007 | Mernoe et al. |
| 2007/0124002 A1 | 5/2007 | Estes et al. |
| 2007/0142776 A9 | 6/2007 | Kovelman et al. |
| 2007/0155307 A1 | 7/2007 | Ng et al. |
| 2007/0156092 A1 | 7/2007 | Estes et al. |
| 2007/0156094 A1 | 7/2007 | Safabash et al. |
| 2007/0166170 A1 | 7/2007 | Nason et al. |
| 2007/0167905 A1 | 7/2007 | Estes et al. |
| 2007/0167912 A1 | 7/2007 | Causey et al. |
| 2007/0169607 A1 | 7/2007 | Keller et al. |
| 2007/0173761 A1 | 7/2007 | Kanderian et al. |
| 2007/0179444 A1 | 8/2007 | Causey et al. |
| 2007/0191702 A1 | 8/2007 | Yodfat et al. |
| 2007/0219432 A1 | 9/2007 | Thompson |
| 2007/0219480 A1 | 9/2007 | Kamen et al. |
| 2007/0233521 A1 | 10/2007 | Wehba et al. |
| 2007/0239116 A1 | 10/2007 | Follman et al. |
| 2007/0248238 A1 | 10/2007 | Abreu |
| 2007/0252774 A1 | 11/2007 | Qi et al. |
| 2007/0255250 A1 | 11/2007 | Moberg et al. |
| 2007/0282299 A1 | 12/2007 | Hellwig |
| 2007/0287931 A1 | 12/2007 | Dilorenzo |
| 2008/0009824 A1 | 1/2008 | Moberg et al. |
| 2008/0015422 A1 | 1/2008 | Wessel |
| 2008/0027574 A1 | 1/2008 | Thomas |
| 2008/0031481 A1 | 2/2008 | Warren et al. |
| 2008/0033357 A1 | 2/2008 | Mann et al. |
| 2008/0045891 A1 | 2/2008 | Maule et al. |
| 2008/0051697 A1 | 2/2008 | Mounce et al. |
| 2008/0051698 A1 | 2/2008 | Mounce et al. |
| 2008/0051714 A1 | 2/2008 | Moberg et al. |
| 2008/0051716 A1 | 2/2008 | Stutz |
| 2008/0051730 A1 | 2/2008 | Bikovsky |
| 2008/0051738 A1 | 2/2008 | Griffin |
| 2008/0077081 A1 | 3/2008 | Mounce et al. |
| 2008/0097326 A1 | 4/2008 | Moberg et al. |
| 2008/0097375 A1 | 4/2008 | Bikovsky |
| 2008/0097381 A1 | 4/2008 | Moberg et al. |
| 2008/0103022 A1 | 5/2008 | Dvorak et al. |
| 2008/0109050 A1 | 5/2008 | John |
| 2008/0125700 A1 | 5/2008 | Moberg et al. |
| 2008/0125701 A1 | 5/2008 | Moberg et al. |
| 2008/0129535 A1 | 6/2008 | Thompson et al. |
| 2008/0147004 A1 | 6/2008 | Mann et al. |
| 2008/0147050 A1 | 6/2008 | Mann et al. |
| 2008/0172027 A1 | 7/2008 | Blomquist |
| 2008/0177165 A1 | 7/2008 | Blomquist et al. |
| 2008/0183060 A1 | 7/2008 | Steil et al. |
| 2008/0188796 A1 | 8/2008 | Steil et al. |
| 2008/0198012 A1 | 8/2008 | Kamen |
| 2008/0201325 A1 | 8/2008 | Doniger et al. |
| 2008/0208627 A1 | 8/2008 | Skyggebjerg |

(56) References Cited

U.S. PATENT DOCUMENTS

| | | |
|---|---|---|
| 2008/0215035 A1 | 9/2008 | Yodfat et al. |
| 2008/0234630 A1 | 9/2008 | Iddan et al. |
| 2008/0255516 A1 | 10/2008 | Yodfat et al. |
| 2008/0269683 A1 | 10/2008 | Bikovsky |
| 2008/0269687 A1 | 10/2008 | Chong et al. |
| 2008/0269714 A1 | 10/2008 | Mastrototaro et al. |
| 2008/0269723 A1 | 10/2008 | Mastrototaro et al. |
| 2008/0275384 A1 | 11/2008 | Mastrototaro |
| 2008/0294094 A1 | 11/2008 | Mhatre et al. |
| 2008/0294108 A1 | 11/2008 | Briones et al. |
| 2008/0294109 A1 | 11/2008 | Estes et al. |
| 2008/0294142 A1 | 11/2008 | Patel et al. |
| 2008/0300572 A1 | 12/2008 | Rankers et al. |
| 2008/0306434 A1 | 12/2008 | Dobbles et al. |
| 2008/0306444 A1 | 12/2008 | Brister et al. |
| 2008/0312512 A1 | 12/2008 | Brukalo et al. |
| 2008/0312634 A1 | 12/2008 | Helmerson et al. |
| 2008/0319381 A1 | 12/2008 | Yodfat et al. |
| 2008/0319383 A1 | 12/2008 | Byland et al. |
| 2008/0319384 A1 | 12/2008 | Yodfat et al. |
| 2008/0319394 A1 | 12/2008 | Yodfat et al. |
| 2008/0319414 A1 | 12/2008 | Yodfat et al. |
| 2008/0319416 A1 | 12/2008 | Yodfat et al. |
| 2009/0036760 A1* | 2/2009 | Hayter ................ A61B 5/7221 600/316 |
| 2009/0036870 A1 | 2/2009 | Mounce et al. |
| 2009/0043291 A1 | 2/2009 | Thompson |
| 2009/0048584 A1 | 2/2009 | Thompson |
| 2009/0067989 A1 | 3/2009 | Estes et al. |
| 2009/0069745 A1 | 3/2009 | Estes et al. |
| 2009/0069746 A1 | 3/2009 | Miller et al. |
| 2009/0069749 A1 | 3/2009 | Miller et al. |
| 2009/0069784 A1 | 3/2009 | Estes et al. |
| 2009/0069785 A1 | 3/2009 | Miller et al. |
| 2009/0069787 A1 | 3/2009 | Estes et al. |
| 2009/0076453 A1 | 3/2009 | Mejlhede et al. |
| 2009/0076849 A1 | 3/2009 | Diller |
| 2009/0082728 A1 | 3/2009 | Bikovsky |
| 2009/0093756 A1 | 4/2009 | Minaie et al. |
| 2009/0099507 A1 | 4/2009 | Koops |
| 2009/0105636 A1 | 4/2009 | Hayter et al. |
| 2009/0112333 A1 | 4/2009 | Sahai Anil K |
| 2009/0118664 A1 | 5/2009 | Estes et al. |
| 2009/0143916 A1 | 6/2009 | Boll et al. |
| 2009/0149728 A1 | 6/2009 | Van Antwerp et al. |
| 2009/0156990 A1 | 6/2009 | Wenger et al. |
| 2009/0164190 A1* | 6/2009 | Hayter ................ G06F 19/3456 703/11 |
| 2009/0177142 A1 | 7/2009 | Blomquist et al. |
| 2009/0177154 A1 | 7/2009 | Blomquist |
| 2009/0192722 A1 | 7/2009 | Shariati et al. |
| 2009/0198191 A1 | 8/2009 | Chong et al. |
| 2009/0198215 A1 | 8/2009 | Chong et al. |
| 2009/0221890 A1 | 9/2009 | Saffer et al. |
| 2009/0234213 A1 | 9/2009 | Hayes et al. |
| 2009/0264856 A1 | 10/2009 | Lebel et al. |
| 2009/0275887 A1 | 11/2009 | Estes |
| 2010/0010329 A1 | 1/2010 | Taub et al. |
| 2010/0010330 A1 | 1/2010 | Rankers et al. |
| 2010/0049164 A1 | 2/2010 | Estes |
| 2010/0056992 A1 | 3/2010 | Hayter |
| 2010/0057040 A1 | 3/2010 | Hayter |
| 2010/0057041 A1 | 3/2010 | Hayter |
| 2010/0057042 A1 | 3/2010 | Hayter |
| 2010/0094078 A1 | 4/2010 | Weston |
| 2010/0094251 A1 | 4/2010 | Estes |
| 2010/0121167 A1 | 5/2010 | McGarraugh |
| 2010/0121170 A1 | 5/2010 | Rule |
| 2010/0165795 A1 | 7/2010 | Elder et al. |
| 2010/0168538 A1 | 7/2010 | Keenan et al. |
| 2010/0168820 A1 | 7/2010 | Maniak et al. |
| 2010/0174229 A1 | 7/2010 | Hsu et al. |
| 2010/0174266 A1 | 7/2010 | Estes |
| 2010/0179409 A1 | 7/2010 | Kamath |
| 2010/0185142 A1 | 7/2010 | Kamen et al. |
| 2010/0228110 A1 | 9/2010 | Tsoukalis |
| 2010/0249530 A1 | 9/2010 | Rankers et al. |
| 2010/0273738 A1 | 10/2010 | Valcke et al. |
| 2010/0280441 A1 | 11/2010 | Wilinska et al. |
| 2010/0286601 A1 | 11/2010 | Yodfat et al. |
| 2010/0286653 A1 | 11/2010 | Kubel et al. |
| 2010/0295686 A1* | 11/2010 | Sloan ................... A61B 5/746 340/573.1 |
| 2010/0298685 A1 | 11/2010 | Hayter et al. |
| 2010/0298765 A1 | 11/2010 | Budiman et al. |
| 2010/0324382 A1 | 12/2010 | Cantwell et al. |
| 2010/0324977 A1 | 12/2010 | Dragt |
| 2010/0325864 A1 | 12/2010 | Briones et al. |
| 2011/0009813 A1 | 1/2011 | Rankers |
| 2011/0015511 A1 | 1/2011 | Bousamra et al. |
| 2011/0034909 A1 | 2/2011 | Lebel et al. |
| 2011/0040247 A1 | 2/2011 | Mandro et al. |
| 2011/0071464 A1 | 3/2011 | Palerm |
| 2011/0098637 A1 | 4/2011 | Hill |
| 2011/0098674 A1 | 4/2011 | Vicente et al. |
| 2011/0105955 A1 | 5/2011 | Yudovsky et al. |
| 2011/0106011 A1 | 5/2011 | Cinar et al. |
| 2011/0106050 A1 | 5/2011 | Yodfat et al. |
| 2011/0112505 A1 | 5/2011 | Starkweather et al. |
| 2011/0112506 A1 | 5/2011 | Starkweather et al. |
| 2011/0118699 A1 | 5/2011 | Yodfat et al. |
| 2011/0124996 A1 | 5/2011 | Reinke et al. |
| 2011/0130716 A1 | 6/2011 | Estes et al. |
| 2011/0163880 A1 | 7/2011 | Halff et al. |
| 2011/0172635 A1 | 7/2011 | Estes |
| 2011/0184380 A1 | 7/2011 | Starkweather et al. |
| 2011/0199194 A1 | 8/2011 | Waldock et al. |
| 2011/0208155 A1 | 8/2011 | Palerm et al. |
| 2011/0224523 A1 | 9/2011 | Budiman |
| 2011/0313390 A1 | 12/2011 | Roy et al. |
| 2011/0319813 A1 | 12/2011 | Kamen et al. |
| 2012/0010600 A1 | 1/2012 | Wilinska et al. |
| 2012/0016304 A1 | 1/2012 | Patel et al. |
| 2012/0029468 A1 | 2/2012 | Diperna et al. |
| 2012/0046606 A1 | 2/2012 | Arefieg |
| 2012/0065894 A1 | 3/2012 | Tubb et al. |
| 2012/0078067 A1 | 3/2012 | Kovatchev et al. |
| 2012/0109113 A1 | 5/2012 | Lebel et al. |
| 2012/0123234 A1 | 5/2012 | Atlas et al. |
| 2012/0136336 A1* | 5/2012 | Mastrototaro ...... A61B 5/14532 604/504 |
| 2012/0150556 A1 | 6/2012 | Galasso et al. |
| 2012/0172694 A1 | 7/2012 | Desborough et al. |
| 2012/0172802 A1 | 7/2012 | Blomquist |
| 2012/0185267 A1 | 7/2012 | Kamen et al. |
| 2012/0197207 A1 | 8/2012 | Stefanski |
| 2012/0203467 A1 | 8/2012 | Kamath et al. |
| 2012/0209208 A1 | 8/2012 | Stefanski |
| 2012/0227737 A1 | 9/2012 | Mastrototaro et al. |
| 2012/0238851 A1 | 9/2012 | Kamen et al. |
| 2012/0238853 A1 | 9/2012 | Arefieg |
| 2012/0238999 A1 | 9/2012 | Estes et al. |
| 2012/0245448 A1 | 9/2012 | Shariati et al. |
| 2012/0245556 A1 | 9/2012 | Kovatchev et al. |
| 2012/0245855 A1 | 9/2012 | Kamath et al. |
| 2012/0246106 A1 | 9/2012 | Atlas et al. |
| 2012/0259191 A1 | 10/2012 | Shariati et al. |
| 2012/0259278 A1 | 10/2012 | Hayes et al. |
| 2012/0265126 A1 | 10/2012 | Estes |
| 2012/0277723 A1 | 11/2012 | Skladnev et al. |
| 2012/0283694 A1 | 11/2012 | Yodfat et al. |
| 2012/0289931 A1 | 11/2012 | Robinson et al. |
| 2012/0302991 A1 | 11/2012 | Blomquist et al. |
| 2012/0323590 A1 | 12/2012 | Udani |
| 2012/0330270 A1 | 12/2012 | Colton |
| 2013/0046281 A1 | 2/2013 | Javitt |
| 2013/0053818 A1 | 2/2013 | Estes |
| 2013/0053819 A1 | 2/2013 | Estes |
| 2013/0053820 A1 | 2/2013 | Estes et al. |
| 2013/0102867 A1 | 4/2013 | Desborough et al. |
| 2013/0116649 A1 | 5/2013 | Breton et al. |
| 2013/0138205 A1 | 5/2013 | Kushwaha et al. |
| 2013/0159456 A1 | 6/2013 | Daoud et al. |
| 2013/0165041 A1 | 6/2013 | Bukovjan et al. |

(56) References Cited

U.S. PATENT DOCUMENTS

| | | |
|---|---|---|
| 2013/0204186 A1 | 8/2013 | Moore et al. |
| 2013/0204202 A1 | 8/2013 | Trombly et al. |
| 2013/0218126 A1 | 8/2013 | Hayter et al. |
| 2013/0237932 A1 | 9/2013 | Thueer et al. |
| 2013/0245563 A1 | 9/2013 | Mercer et al. |
| 2013/0245604 A1 | 9/2013 | Kouyoumjian et al. |
| 2013/0253418 A1 | 9/2013 | Kamath et al. |
| 2013/0275139 A1 | 10/2013 | Coleman |
| 2013/0297334 A1 | 11/2013 | Galasso et al. |
| 2013/0338629 A1 | 12/2013 | Agrawal et al. |
| 2013/0338630 A1 | 12/2013 | Agrawal et al. |
| 2013/0345663 A1 | 12/2013 | Agrawal et al. |
| 2014/0005633 A1 | 1/2014 | Finan |
| 2014/0025015 A1 | 1/2014 | Cross et al. |
| 2014/0031759 A1 | 1/2014 | Kouyoumjian et al. |
| 2014/0039383 A1 | 2/2014 | Dobbles et al. |
| 2014/0052091 A1 | 2/2014 | Dobbles et al. |
| 2014/0052092 A1 | 2/2014 | Dobbles et al. |
| 2014/0052093 A1 | 2/2014 | Dobbles et al. |
| 2014/0052094 A1 | 2/2014 | Dobbles et al. |
| 2014/0052095 A1 | 2/2014 | Dobbles et al. |
| 2014/0066884 A1 | 3/2014 | Keenan et al. |
| 2014/0066885 A1 | 3/2014 | Keenan et al. |
| 2014/0066886 A1 | 3/2014 | Roy et al. |
| 2014/0066887 A1 | 3/2014 | Mastrototaro et al. |
| 2014/0066888 A1 | 3/2014 | Parikh et al. |
| 2014/0066889 A1 | 3/2014 | Grosman et al. |
| 2014/0066890 A1 | 3/2014 | Sloan et al. |
| 2014/0066892 A1 | 3/2014 | Keenan et al. |
| 2014/0088557 A1 | 3/2014 | Mernoe et al. |
| 2014/0094766 A1 | 4/2014 | Estes et al. |
| 2014/0107607 A1 | 4/2014 | Estes |
| 2014/0114278 A1 | 4/2014 | Dobbles et al. |
| 2014/0121635 A1 | 5/2014 | Hayter |
| 2014/0128705 A1 | 5/2014 | Mazlish |
| 2014/0128803 A1 | 5/2014 | Dobbles et al. |
| 2014/0163517 A1 | 6/2014 | Finan et al. |
| 2014/0180203 A1 | 6/2014 | Budiman et al. |
| 2014/0180240 A1 | 6/2014 | Finan et al. |
| 2014/0228627 A1 | 8/2014 | Soffer et al. |
| 2014/0228668 A1 | 8/2014 | Wakizaka et al. |
| 2014/0235981 A1 | 8/2014 | Hayter |
| 2014/0249500 A1* | 9/2014 | Estes ................ A61M 5/14244 604/504 |
| 2014/0276553 A1 | 9/2014 | Rosinko et al. |
| 2014/0276554 A1 | 9/2014 | Finan et al. |
| 2014/0276555 A1 | 9/2014 | Morales |
| 2014/0276583 A1 | 9/2014 | Chen et al. |
| 2014/0309615 A1 | 10/2014 | Mazlish |
| 2014/0323959 A1 | 10/2014 | Lebel et al. |
| 2015/0018633 A1 | 1/2015 | Kovachev et al. |
| 2015/0018757 A1 | 1/2015 | Starkweather et al. |
| 2015/0025471 A1 | 1/2015 | Enggaard |
| 2015/0025495 A1 | 1/2015 | Peyser |
| 2015/0030641 A1 | 1/2015 | Anderson et al. |
| 2015/0045737 A1 | 2/2015 | Stefanski |
| 2015/0073337 A1 | 3/2015 | Saint et al. |
| 2015/0080789 A1 | 3/2015 | Estes et al. |
| 2015/0100038 A1 | 4/2015 | McCann et al. |
| 2015/0120323 A1 | 4/2015 | Galasso et al. |
| 2015/0136336 A1 | 5/2015 | Huang |
| 2015/0148774 A1 | 5/2015 | Yao |
| 2015/0157794 A1 | 6/2015 | Roy et al. |
| 2015/0164414 A1 | 6/2015 | Matthews |
| 2015/0165119 A1 | 6/2015 | Palerm et al. |
| 2015/0217051 A1 | 8/2015 | Mastrototaro et al. |
| 2015/0217052 A1 | 8/2015 | Keenan et al. |
| 2015/0265767 A1 | 9/2015 | Vazquez et al. |
| 2015/0265768 A1 | 9/2015 | Vazquez et al. |
| 2015/0314062 A1 | 11/2015 | Blomquist et al. |
| 2015/0320933 A1 | 11/2015 | Estes |
| 2015/0328402 A1 | 11/2015 | Nogueira et al. |
| 2015/0351683 A1 | 12/2015 | Brauker et al. |
| 2015/0352282 A1 | 12/2015 | Mazlish |
| 2015/0352283 A1 | 12/2015 | Galasso |
| 2016/0000998 A1 | 1/2016 | Estes |
| 2016/0030669 A1 | 2/2016 | Harris et al. |
| 2016/0038673 A1 | 2/2016 | Morales |
| 2016/0082187 A1 | 3/2016 | Schiable et al. |
| 2016/0082188 A1 | 3/2016 | Blomquist et al. |
| 2016/0158438 A1 | 6/2016 | Monirabbasi et al. |
| 2016/0162662 A1 | 6/2016 | Monirabbasi et al. |
| 2016/0213841 A1 | 7/2016 | Geismar et al. |
| 2016/0256629 A1 | 9/2016 | Grosman et al. |
| 2017/0182248 A1 | 6/2017 | Rosinko |
| 2017/0203036 A1 | 7/2017 | Mazlish et al. |

FOREIGN PATENT DOCUMENTS

| | | |
|---|---|---|
| DE | 19627619 | 1/1998 |
| DE | 19912459 A1 | 9/2000 |
| DE | 10236669 A1 | 2/2004 |
| DE | 202005012358 U1 | 10/2005 |
| DK | PA200401893 | 12/2004 |
| EP | 0062974 A1 | 10/1982 |
| EP | 0098592 A2 | 1/1984 |
| EP | 0275213 A2 | 7/1988 |
| EP | 0496141 A1 | 7/1992 |
| EP | 0580723 A1 | 2/1994 |
| EP | 0612004 A1 | 8/1994 |
| EP | 0721358 A1 | 7/1996 |
| EP | 1045146 A2 | 10/2000 |
| EP | 1136698 A1 | 9/2001 |
| EP | 1177802 B1 | 9/2004 |
| EP | 1495775 A1 | 1/2005 |
| EP | 1527792 A1 | 5/2005 |
| EP | 1754498 A1 | 2/2007 |
| EP | 1818664 A1 | 8/2007 |
| EP | 1824536 A1 | 8/2007 |
| EP | 1951340 A1 | 8/2008 |
| EP | 2764881 A1 | 8/2014 |
| FR | 2585252 A1 | 1/1987 |
| GB | 0747701 | 4/1956 |
| GB | 2218831 A | 11/1989 |
| JP | 09-504974 A | 5/1997 |
| JP | 11-010036 A | 1/1999 |
| JP | 2000-513974 A | 10/2000 |
| JP | 2002-507459 A | 3/2002 |
| JP | 2002-523149 A | 7/2002 |
| WO | 90/15928 A1 | 12/1990 |
| WO | 95/09021 A1 | 4/1995 |
| WO | 97/21457 A1 | 6/1997 |
| WO | 98/04301 A1 | 2/1998 |
| WO | 98/11927 A1 | 3/1998 |
| WO | 98/57683 A1 | 12/1998 |
| WO | 99/07425 A1 | 2/1999 |
| WO | 99/21596 A1 | 5/1999 |
| WO | 99/39118 A1 | 8/1999 |
| WO | 99/48546 A1 | 9/1999 |
| WO | 01/54753 A2 | 8/2001 |
| WO | 01/72360 A1 | 10/2001 |
| WO | 01/91822 A1 | 12/2001 |
| WO | 01/91833 A1 | 12/2001 |
| WO | 02/40083 A2 | 5/2002 |
| WO | 02/57627 A1 | 7/2002 |
| WO | 02/68015 A2 | 9/2002 |
| WO | 02/81012 A2 | 10/2002 |
| WO | 02/84336 A2 | 10/2002 |
| WO | 2002/100469 A2 | 12/2002 |
| WO | 03/23728 A1 | 3/2003 |
| WO | 03/26728 A1 | 3/2003 |
| WO | 03/26726 A1 | 4/2003 |
| WO | 2003/103763 A1 | 12/2003 |
| WO | 2004/041330 A2 | 5/2004 |
| WO | 2004/056412 A2 | 7/2004 |
| WO | 2004/093648 A2 | 11/2004 |
| WO | 2004/110526 A1 | 12/2004 |
| WO | 2005/002652 A2 | 1/2005 |
| WO | 2005/011779 A1 | 2/2005 |
| WO | 2005/011799 A1 | 2/2005 |
| WO | 2005/039673 A2 | 5/2005 |
| WO | 2005/072794 A2 | 8/2005 |
| WO | 2005/072795 A2 | 8/2005 |
| WO | 2006/061354 A1 | 6/2006 |

(56) References Cited

FOREIGN PATENT DOCUMENTS

| | | |
|---|---|---|
| WO | 2006/067217 A2 | 6/2006 |
| WO | 2006/075016 A1 | 7/2006 |
| WO | 2006/097453 A1 | 9/2006 |
| WO | 2006/105792 A1 | 10/2006 |
| WO | 2006/105793 A1 | 10/2006 |
| WO | 2006/105794 A1 | 10/2006 |
| WO | 2007/005219 A1 | 1/2007 |
| WO | 2007/056247 A2 | 5/2007 |
| WO | 2007/056504 A1 | 5/2007 |
| WO | 2007/056592 A2 | 5/2007 |
| WO | 2007/071255 A1 | 6/2007 |
| WO | 2007/078992 A1 | 7/2007 |
| WO | 2007/141786 A1 | 12/2007 |
| WO | 2008/016621 A1 | 2/2008 |
| WO | 2008/073609 A2 | 6/2008 |
| WO | 2008/089184 A2 | 7/2008 |
| WO | 2009/032402 A1 | 3/2009 |
| WO | 2009/035759 A1 | 3/2009 |
| WO | 2010/045460 A2 | 4/2010 |
| WO | 2010/097796 A1 | 9/2010 |
| WO | 2014/062399 A1 | 4/2014 |
| WO | 2014/074476 A1 | 5/2014 |
| WO | 2014/134459 A1 | 9/2014 |
| WO | 2014/172467 A1 | 10/2014 |
| WO | 2015/191459 A1 | 12/2015 |
| WO | 2016/004210 A1 | 1/2016 |

OTHER PUBLICATIONS

International Search Report and Written Opinion in Application No. PCT/US2016/067676, dated Mar. 31, 2017, 15 pages.
Keith Hynes et al., "DiAs User Interface: A Patient-Centric Interface for Mobile Artificial Pancreas Systems," J Diabetes Sci Tech 7(6):1416-1426, Nov. 2013.
Kovatchev et al., "Safety of Outpatient Closed-Loop Control: First Randomized Crossover Trials of a Wearable Artificial Pancreas," Diabetes Care 37(7):1789-1796, Jul. 2014.
Percival et al., "Closed-Loop Control and Advisory Mode Evaluation of an Artificial Pancreatic β Cell: Use of Proportional-Integral-Derivative Equivalent Model-Based Controllers," J Diabetes Sci Tech 2(4):636-644, Jul. 2008.
Copp et al., "Simultaneous Model Predictive Control and Moving Horizon Estimation for Blood Glucose Regulation in Type 1 Diabetes," Optim. Control Appl. Meth. 2016, 15 pages.
Dassau et al., "12-Week 24/7 Ambulatory Artificial Pancreas With Weekly Adaptation of Insulin Delivery Settings: Effect on Hemoglobin A1c and Hypoglycemia" Diabetes Care, Dec. 1, 2017, 40(12):1719-26.
Dumont, "Feedback control for clinicians," Journal of clinical monitoring and computing, Feb. 1, 2014, 28(1):5-11.
Fischer et al., "In Vivo Comparison of Different Algorithms for the Artificial Beta-Cell," Artificial organs, May 1, 1985, 9(2):173-9.
Salzsieder et al., "Estimation of individually adapted control parameters for an artificial beta cell," Biomed. Biochim. Acta, Jan. 1, 1984, 43(5):585-596.
Shiavon et al., "Quantitative Estimation of Insulin Sensitivity in Type 1 Diabetic Subjects Wearing a Sensor-Augmented Insulin Pump," Diabetes care, May 1, 2014, 37(5):1216-23.
Vozeh et al., "Feedback Control Methods for Drug Dosage Optimisation, Concepts, Classifications and Clinical Application," Clinical pharmacokinetics, Nov. 1, 1985, 10(6):457-76.
"Minimed Inc. Introduces 407C Infusion Pump for General Medication Use" [online]. Business Wire, AllBusiness.com, Aug. 10, 1999 [retrieved on Feb. 28, 2011]. Retrieved from the Internet: <URL: http://www.allbusiness.com/company-activities-management/product-management/6734565-1.html>.
"Using the Deltec Cozmo Insulin Pump Correction Bolus Feature" believed to be publicly available before May 5, 2008, pp. 36-41.
"Which Insulin Pump is Right for Me?", Albany Medical Center, Goodman Diabetes Service, Jan. 2006, 4 pages.
Accu-Chek Spirit, "Pump Therapy Made for You," Roche, 2006, 6 pages.
Animas Corporation, IR1200 User Guide Manual, pp. 29-31, revised Sep. 2006.
Asante Solutions Pearl User Manual, Asante Inc., 2012, 180 pages.
Brown et al., "CGM, Pumps, and SMBG." American Diabetes Association- 71st Scientific Sessions, San Diego, CA, Jun. 24-28, 2011, 38 pages.
CN Office Action dated Jun. 24, 2020 for CN Application No. 201680077880.
Collins and Lee, "Microfluidic flow transducer based on the measurement of electrical admittance," Lab Chip, 2004, 4:7-10.
Cox et al. "Prediction of Severe Hypoglycemia." Diabetes Care, vol. 30, No. 6, Jun. 2007, 4 pages.
Debiotech SA; Debiotech reveals its new miniaturized Disposable Insulin Nanopump} for Diabetes therapy (news release); retrieved from the internet: (http://web.archive.org/web/20060822033820/http://www.debiotech.com/news/nw_159.html); 3 pgs.; Apr. 24, 2006.
DOCNEWS; The latest in high-tech and convenient devices; American Diabetes Assoc.; 2(7); retrieved from the internet: (http://web.archive.org/web/20080526162751/http://docnews.diabetesjournals.org/cgi/content/full/2/7/13?); 3 pgs.; Jul. 1, 2005.
Duden Deutsches Universaiworterbuch, Dudenveriag, Mannheim, 1989, p. 822.
Guarnieri et al.; Flexible versus rigid catheters for chronic administration of exogenous agents into central nervous system tissues (abstract only); J Neurosc Meth; 144(2); pp. 147-152; Jun. 2005.
Insulet Corporation; Innovative New System for Managing Diabetes Receives FDA Clearance; The OmniPod (Registered) Insulin Management System (press release); retrieved from the internet: (http://phx.corporate-ir.net/phoenix.zhtml? c=209336&p=irol-newsArticle_pf&ID=988708&highlight=); 2 pgs.; Feb. 1, 2005.
Insulet Corporation; OmniPod (Registered) Insulin Management System (quick-start guide); 2 pgs.; (Copyright) 2008.
Medtronic News Release, "Medtronic Receives FDA Approval for World's First Insulin Pump with Real-time Continuous Glucose Monitoring," Apr. 13, 2006, 3 pages.
OmniPod Insulin Management System—Investor Relations—Press Release, Feb. 1, 2005, http://investors.insulet.com/phoenix.zhtml? c=209336&p=irol-newsA- rticle&ID=988708&highlight= 1 page.
OmniPod Quick Start Guide, 2007, 2 pages.
Oxford Advanced Learners Dictionary, 4th Ed., Oxford University Press, Oxford, 1989, p. 178.
Patent Abstracts of Japan, vol. 1999, No. 4, and JP 11 010036 , Apr. 30, 1999 and Jan. 19, 1999, Toray Ind. Inc.
The Content of Investigational Device Exemption (IDE) and Premarket Approval (PMA) Application for Low Glucose Suspend (LGS) Device System. Rockville, MD, Food and Drug Administration, 2011, 59 pages.
The Medtronic Diabetes Connection, 2006, 6 pages.
U.S. Appl. No. 60/753,984, filed Dec. 23, 2005.
U.S. Appl. No. 11/362,616.
U.S. Appl. No. 60/753,684, filed Dec. 23, 2005.
Walsh et al., "Guidelines for Insulin Dosing in Continuous Subcutaneous Insulin Infusion Using New Formulas from a Retrospective Study of Individuals with Optimal Glucose Levels", J. Diabetes Science and Technology, vol. 4 Issue 5, Sep. 2010 (8 pages.).
Walsh et al.,"Guidelines for Optimal Bolus Calculator Settings in Adults", J. Diabetes Science and Technology; vol. 5 Issue 1; Jan. 2011 (7 pages).
Xilas Temp Touch, "The latest in high-tech and convenient devices," DOCNews, vol. 2, No. 7, Jul. 1, 2005, http://docnews.diabetesioumals.ord/cgi/content/full/2/7/13, 3 pages.

* cited by examiner

OPERATING MULTI-MODAL MEDICINE DELIVERY SYSTEMS

CROSS-REFERENCE TO RELATED APPLICATIONS

This application claims the benefit of U.S. Provisional Ser. No. 62/275,213 filed Jan. 5, 2016. This disclosure of the prior application is considered part of (and is incorporated by reference in) the disclosure of this application.

TECHNICAL FIELD

This document relates to multi-modal medicine delivery systems and methods for managing chronic diseases, such as diabetes.

BACKGROUND

Diabetes mellitus is a chronic metabolic disorder caused by an inability of a person's pancreas to produce sufficient amounts of the hormone, insulin, such that the person's metabolism is unable to provide for the proper absorption of sugar and starch. This failure leads to hyperglycemia, i.e., the presence of an excessive amount of analyte, such as glucose, within the blood plasma. Persistent hyperglycemia has been associated with a variety of serious symptoms and life threatening long-term complications such as dehydration, ketoacidosis, diabetic coma, cardiovascular diseases, chronic renal failure, retinal damage and nerve damages with the risk of amputation of extremities. Because healing is not yet possible, a permanent therapy is necessary which provides constant glycemic control in order to constantly maintain the level of blood analyte within normal limits. Such glycemic control is achieved by regularly supplying medicines (e.g., drugs, hormones), such as insulin, to the body of the patient to thereby reduce the elevated levels of blood analyte.

Historically, an external biologically effective medicine (e.g., insulin or its analog) is commonly administered by means of multiple, daily injections of rapid and long acting medicine via a hypodermic syringe. While this treatment does not require the frequent estimation of blood analyte, it has been found that the degree of glycemic control achievable in this way is suboptimal because the delivery is unlike physiological hormone production, according to which, hormones enter the bloodstream at a lower rate and over a more extended period of time.

Improved glycemic control may be achieved by the so-called intensive medicine therapy, which is based on multiple daily injections, including one or two injections per day of a long acting medicine for providing a basal level of medicine and additional injections of a rapidly acting medicine before each meal in an amount proportional to the size of the meal. Although traditional syringes have at least partly been replaced by medicine pens, the frequent injections are nevertheless very inconvenient for the patient, particularly those who are incapable of reliably self-administering injections.

Substantial improvements in diabetes therapy have been achieved by the development of other drug delivery devices, such as insulin pumps, relieving the patient of the need for syringes or medicine pens and the administration of multiple, daily injections. Insulin pumps allow for the delivery of insulin (and/or other medications) in a manner that bears greater similarity to the naturally occurring physiological processes and can be controlled to follow standard or individually modified protocols to give the patient better glycemic control. In some circumstances, an insulin pump device can store (via input from a clinician or a user) a number of settings (e.g., dosage parameters or other settings) that are customized by the physician for the particular user. In one example, an infusion pump device can be programmed to store a user's insulin sensitivity (e.g., in units of mg/dL/insulin unit), which can be employed by the infusion pump system when calculating a correction bolus dosage for that particular user. In another example, an infusion pump device can be programmed to store a user's carbohydrate ratio (e.g., in units of g/insulin unit), which can be employed by the infusion pump system when calculating meal bolus dosage for that particular user. In many cases, these user-specific settings are manually input into the infusion pump device via user interface buttons on the infusion pump device. If any of these settings are erroneously input into the infusion pump system (e.g., due to a transcribing error or other error when manually inputting the data), the resulting consequences could lead to improper bolus dosage calculations resulting in blood glucose levels that are unnecessarily too high or too low.

In addition, delivery directly into the intraperitoneal space or intravenously can be achieved by drug delivery devices. Drug delivery devices can be constructed as an implantable device for intraperitoneal arrangement or can be constructed as an external device with an infusion set for subcutaneous infusion to the patient via the transcutaneous insertion of a catheter, cannula or a transdermal medicine transport such as through a patch. External drug delivery devices are mounted on clothing, hidden beneath or inside clothing, or mounted on the body and are generally controlled via a user interface built-in to the device or on a separate remote device.

Drug delivery devices have been utilized to assist in the management of diabetes by infusing medicine or a suitable biologically effective material into the diabetic patient at a basal rate with additional medicine or "bolus" to account for meals or high analyte values, levels, or concentrations. The drug delivery device typically is connected to an infuser, better known as an infusion set, by a flexible tube. The infuser typically has a subcutaneous cannula, and an adhesive backed mount on which the cannula is attached. The cannula may include a quick disconnect to allow the cannula and mount to remain in place on the skin surface of the user while the flexible tubing is disconnected from the infuser. Regardless of the type of drug delivery device, blood analyte monitoring is typically required to achieve acceptable glycemic control. For example, delivery of suitable amounts of medicine by the drug delivery device requires that the patient frequently determine his or her blood analyte level and manually input this value into a user interface for the external drug delivery device, which then may calculate a suitable modification to the default or currently in-use medicine delivery protocol, i.e., dosage and timing, and subsequently communicates with the drug delivery device to adjust its operation accordingly. The determination of blood analyte concentration is typically performed by means of an episodic measuring device such as a hand-held electronic meter, which receives blood samples via enzyme-based test strips and calculates the blood analyte value based on the enzymatic reaction. In recent years, continuous analyte monitoring has also been utilized with drug delivery devices to allow for greater control of the medicine(s) being infused into the diabetic patients.

People with diabetes and their health care provider (HCP) bear a great deal of cognitive burden in managing intensive medicine therapy. Delivering the correct amount of the medicine at the correct time is an extremely challenging endeavor. It requires the patient to make dosing determinations multiple times per day and it requires a combination of the patient and the HCP to re-calibrate the therapeutic parameters of the therapy on an episodic time frame that varies from individual to individual, and within individuals based on age and/or behavior (e.g., change in exercise, change in diet).

In light of the many deficiencies and problems associated with current systems and methods for maintaining proper glycemic control, enormous resources have been put into finding better solutions. A number of new technologies promise to mitigate some of the cognitive burden that intensive insulin therapy now requires. Developing workable solutions to the problem that are simple, safe, reliable and able to gain regulatory approval has, however, proved to be elusive. For years, researchers have contemplated coupling a continuous glucose monitoring system with an insulin delivery device to provide an "artificial pancreas" to assist people living with diabetes. Their efforts have yet to result in a commercial product. What has been needed is a system and method that provides a level of automatic control of drug delivery devices for improved medicine delivery and glycemic control that is simple, safe, and reliable in a real world setting.

BRIEF SUMMARY

Multi-modal medicine delivery systems and methods provided herein can monitor the presence of a blood analyte using one or more blood analyte monitoring devices or methods, control or monitor the dispensation of medicine, and determine and/or update control parameters that control or recommend medicine delivery for multiple operating modes. For example, if the blood analyte is glucose, exemplary modes of medicine delivery include closed-loop modes that regularly update basal rates and the parameters for calculating a bolus using continuous glucose monitoring (CGM) data, partially closed-loop modes that can use blood glucose monitor (BGM) data to update basal rates and bolus control parameters over longer periods of time, manual modes that require a patient to manually control the therapy program using an insulin pump, and advisory modes that recommend dosages for a user to inject using an insulin pen or syringe. By determining optimized control parameters that work across delivery modes, multi-modal medicine delivery systems and methods provided herein can provide superior analyte control even when a user switches to a different delivery mode. For example, a multi-modal medicine delivery system provided herein may be forced to switch away from a fully closed-loop medicine delivery mode if a continuous analyte monitor malfunctions or the system otherwise loses access to continuous data. In some cases, data can be collected when the system is in an advisory or manual mode to optimize control parameters in preparation for a user to switch to a closed loop system (e.g., in preparation for a user to start use of a continuous glucose monitor (CGM) and/or an insulin pump).

Multi-modal medicine delivery systems provided herein are configured, at least in part, by a secondary feedback loop running in parallel across the multiple delivery modes. The multiple delivery modes can include, for example, a closed-loop delivery mode and an open-loop delivery mode. During a closed-loop delivery mode, a multi-modal medicine delivery system may dispense medicine according to an automated control algorithm that adjusts the medicine dispensation rate in response to sensor feedback (e.g., a blood glucose sensor) or other feedback, whereas in an open-loop delivery mode the multi-modal medicine delivery system may dispense medicine based, at least in part, on user input of a predetermined dispensation schedule or manually selected bolus amounts. Other delivery modes are also described herein. In particular embodiments, the multi-modal medicine delivery system can perform a secondary feedback loop in parallel with a delivery mode that is being used to operate the infusion pump system. Such a secondary feedback loop can iteratively obtain data (e.g., blood glucose readings, dosage information, user inputs) from the delivery mode that is being used to operate the multi-modal medicine delivery system as well as from other delivery modes that were previously used to operate the multi-modal medicine delivery system, and can use the data to determine information (e.g., parameters and/or models for dosage delivery) that is used by the multiple delivery modes to dispense medicine.

For example, while a multi-modal medicine delivery system is operating in a closed-loop delivery mode, a secondary feedback loop can, in parallel with and separate from the closed-loop delivery mode, collect data obtained during the closed-loop delivery mode (and other delivery modes) and update, based at least in part on the collected data, user-specific parameters and/or models for dosage delivery that are used for the closed-loop delivery mode (and other delivery modes). Such a secondary feedback loop can additionally provide such updated parameters and/or models for use during closed-loop delivery mode (and subsequent delivery modes) without exiting or otherwise interrupting the closed-loop delivery mode.

In some cases, multi-modal medicine delivery systems can be configured to transition between multiple delivery modes automatically and/or manually. For example, several trigger conditions can be used to automatically determine when to transition between a closed delivery mode to an open delivery mode, such as a signal for a sensor (e.g., glucose monitoring device) becoming unavailable and/or a time period for operating in the closed delivery mode expiring. In another example, a multi-modal medicine delivery system can be configured to provide one or more user interfaces (e.g., graphical user interface, audio user interface, motion-based user interface) through which a user can provide input to indicate a request to transition between delivery modes, such as transitioning from an open delivery mode to a closed delivery mode and/or vice versa.

In one implementation, a method includes selecting a first delivery mode from among a plurality of delivery modes to use for operating a multi-modal medicine delivery system to dispense one or more medications adapted to alter a blood analyte level; delivering the one or more medications to the user according to the first delivery mode, the first delivery mode providing a schedule of medication delivery based upon user-specific dosage parameters and a primary feedback loop corresponding to the first delivery mode; obtaining, while the infusion pump system is operating according to and without exiting the first delivery mode, (i) analyte sensor data and (ii) medicine delivery data or food intake data, the analyte sensor data being generated by an analyte sensor and indicating the blood analyte level for the user at one or more specific times, the medicine delivery data identifying amounts and times at which the one or more medications were delivered to the user, the food intake data identifying amounts and times at which one or more foods were consumed by the user; determining, using a secondary feedback loop, one or more updates to the user-specific dosage parameters based on (i) the analyte sensor data and (ii) the medicine delivery data or the food intake data; delivering the one or more medications to the user according to the first delivery mode based upon the updated user-specific dosage parameters; and switching to a second delivery mode and delivering the one or more medications to the user according to the second delivery mode and the updated user-specific dosage parameters.

Such a method can, in some instances, optionally include one or more of the following features. The analyte sensor data can include data describing blood glucose readings and the medicine delivery data identifies insulin dosages delivered to the user. The switching can include determining whether to transition out of operating the multi-modal medicine delivery system according to the first delivery mode; selecting, in response to a determination to transition out of operating according to the first delivery mode, the second delivery mode to use for operating the multi-modal medicine delivery system from among the plurality of delivery modes; and operating the multi-modal medicine delivery system to dispense the one or more medications according to the second delivery mode and the updated user-specific dosage parameters. The method can further include, while the multi-modal medicine delivery system is operating according to and without exiting the second delivery mode, performing the following: obtaining additional analyte sensor data and additional medicine delivery from operation of the multi-modal medicine delivery system according to the second delivery mode and the updated user-specific dosage parameters; determining, using the secondary feedback loop, one or more additional updates to the user-specific dosage parameters based on (i) the additional analyte sensor data and (ii) the additional medicine delivery data; and delivering the one or more medications to the user according to the second delivery mode based upon the additional updates to the user-specific dosage parameters.

The secondary feedback loop can determine the additional updates to the user-specific dosage parameters based on both (i) the analyte sensor data and the medicine delivery data generated during the first delivery mode, and (ii) the additional analyte sensor data and the additional medicine delivery data generated during the second delivery mode. The determination to transition out of operating according to the first delivery mode can be based on detection of a transition trigger event. The transition trigger event can be detected automatically and is not based on user input. The transition trigger event can include a signal to the analyte sensor being lost or acquired. The transition trigger event can include expiration of a period of time for operating the multi-modal medicine delivery system according to the first delivery mode. The transition trigger event can include one or more calibrations for components of the multi-modal medicine delivery system being incomplete after a threshold period of time. The transition trigger event can include a time-based schedule for a patient using the multi-modal medicine delivery system indicating that a scheduled transition is to occur at the current time. The transition trigger event can include one or more components of the multi-modal medicine delivery system failing one or more safety checks. The transition trigger event can be detected based on user input provided to the multi-modal medicine delivery system. The plurality of delivery modes can include, at least, a closed-loop delivery mode and an open-loop delivery mode, and the first delivery mode can include the closed-loop delivery mode.

In another implementation, a method includes receiving, as part of a secondary feedback loop that is running in parallel with operation of a multi-modal medicine delivery system according to a first delivery mode from among a plurality of delivery modes, (i) analyte sensor data and (ii) medicine delivery data or food intake data, the analyte sensor data being generated by an analyte sensor and indicating the blood analyte level for the user at one or more specific times, the medicine delivery data identifying amounts and times at which the one or more medications were delivered to the user, the food intake data identifying amounts and times at which one or more foods were consumed by the user; determining, by the secondary feedback loop and based, at least in part, on (i) the analyte sensor data and (ii) the medicine delivery data or the food intake data, whether to update one or more user-specific dosage parameters that are used to operate the infusion pump according to the selected delivery mode; generating, by the secondary feedback loop and in response to determining to update the user-specific dosage parameters, one or more updates to the user-specific dosage parameters; and providing the one or more updates for use with the operation of the multi-modal medicine delivery system according to the first delivery mode, wherein the one or more updates are incorporated into the operation of the multi-modal medicine delivery system without interrupting the first delivery mode.

Such a method can, in some instances, optionally include one or more of the following features. The one or more updates can be determined based on on both (i) the analyte sensor data and the medicine delivery data generated during the first delivery mode, and (ii) additional analyte sensor data and additional medicine delivery data generated during a second delivery mode. The secondary feedback loop can repeatedly perform the receiving, determining, generating, and providing steps across the plurality of delivery modes. The secondary feedback loop can be implemented on a mobile computing device that is in wireless communication with a controller device that (i) controls delivery of one or more medications to a patient by the multi-modal medicine delivery system and (ii) operates the multi-modal medicine delivery system according to the first delivery mode. The plurality of delivery modes can include, at least, a closed-loop delivery mode and an open-loop delivery mode, and the first delivery mode can include the closed-loop delivery mode.

In another implementation, a medical multi-modal medicine delivery system includes a medicine delivery system that receives one or more medications for dispensation to a user, the medicine delivery system at least partially containing a mechanism to dispense the one or more medications to the user; a controller configured to control dispensation of the medicine from the portable pump housing; and wherein the controller is configured to control the dispensation of the one or more medications according to (i) a plurality of delivery modes and (ii) one or more user-specific settings that are determined by a secondary feedback loop that is independent of the plurality of delivery modes, wherein the plurality of delivery modes include, at least, a closed-loop delivery mode and an open-loop delivery mode that both operate based, at least in part, on the one or more user-specific settings that are determined by the secondary feedback loop.

The details of one or more implementations of the invention are set forth in the accompanying drawings and the description below. Other features, objects, and advantages of the invention will be apparent from the description and drawings, and from the claims.

BRIEF DESCRIPTION OF DRAWINGS

Like reference symbols in the various drawings may indicate like elements.

DETAILED DESCRIPTION

Multi-modal medicine delivery systems and methods provided herein may be used and performed, respectively, by a user, for example, a type 1 or 2 diabetes patient or a caregiver of a diabetes patient. In some cases, the systems and methods may be adapted for use with additional chronic diseases or conditions, for example, unresponsive infections, cancer, cancer-related pain, chronic pain, gastrointestinal diseases or disorders, congestive heart failure, hemophilia, immune deficiencies, multiple sclerosis, and rheumatoid arthritis.

Figure 1A:
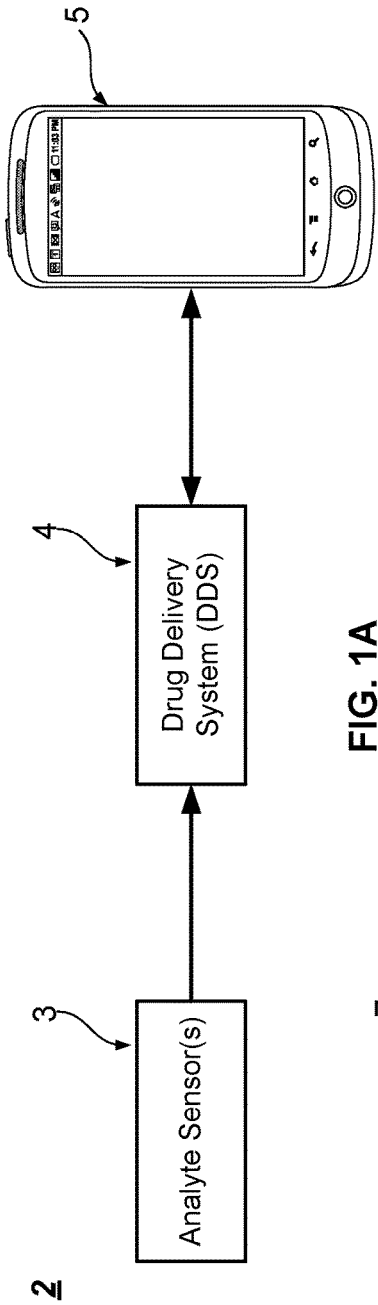
FIGS. 1A and 1B illustrate schematic diagrams of example multi-modal medicine delivery systems for diabetes management.
Figure 1B:
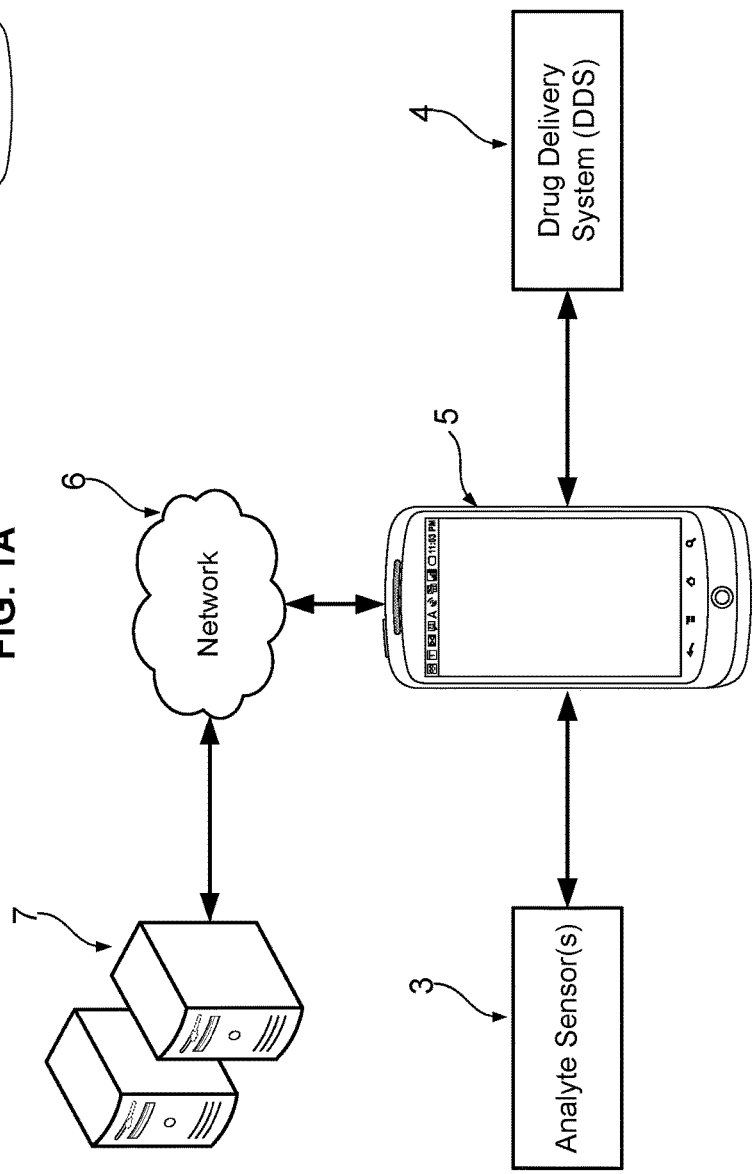

As shown in FIGS. 1A and 1B, an example two-phase multi-modal system 2 for disease management includes an analyte sensor 3 and a computing device 5. In some cases, the example system can further include a drug delivery system 4 (DDS), such as a medical infusion pump. The system 2 functions to guide a patient from complete manual management of a disease, such as diabetes, to or through one or more levels of automation of disease management. Further, the system 2 functions to individualize treatment of the user's condition over time. For example, the system 2 is configured to modify and individualize, over time, a clinician-defined target basal profile and/or basal profile range for a diabetes patient. The system 2 can be used for management of diabetes, but can additionally or alternatively be used for any suitable applications, clinical or otherwise. The system 2 can be configured and/or adapted to function for use with any suitable disease management or treatment plan.

The system 2 includes can include an example analyte sensor 3. The analyte sensor 3 functions to measure one or more analytes, for example, glucose, in a bodily fluid of a user, for example, blood, interstitial fluid, or tears. In some cases, the analyte sensor 3 is a drop-sampled, blood glucose monitor (BGM) or a continuous glucose monitor (CGM) that continuously or near-continuously measures one or more bodily fluids from which blood glucose levels may be inferred. A BGM is typically a small, portable meter that allows a user to measure the level of glucose in the user's blood by piercing his/her skin (e.g., on a finger) and depositing blood on a chemically active, disposable test strip for analysis by the BGM. A CGM is typically a disposable glucose sensor or probe placed just under the skin (i.e., subcutaneously) that measures the interstitial level of glucose through an enzymatic reaction similar to the test strip described above. In some cases, the CGM may be wholly implanted in the patient. In some cases, the CGM requires calibration, for example, one or more times a day, using a BGM.

As shown in FIGS. 1A and 1B, the system 2 includes a computing device 5. In some cases, as shown in FIG. 1A, the computing device 5 receives one or more inputs (e.g., analyte level, dose amount, dose timing, etc.) directly or indirectly from the DDS 4 and/or the analyte sensor 3. For example, the analyte sensor 3 may be coupled to the DDS 4, which is coupled to the computing device 5, as shown in FIG. 1A. Alternatively, in some cases, as shown in FIG. 1B, the computing device 5 is coupled to the analyte sensor 3 and DDS 4, and is configured to communicate bi-directionally with the analyte sensor 3 and DDS 4. For example, the computing device 5 can be programmed to receive one or more readings of an analyte level from the analyte sensor 3 and to alter or adjust a frequency of analyte readings performed by the analyte sensor 3. In some cases, the computing device 5 is further programmed to communicate with the DDS 4 to receive one or more inputs (e.g., dose amount, dose timing, configuration, etc.) and to determine, recommend, and/or deliver one or more doses of a hormone or other medicine needed to regulate the analyte level. One example of such a system 2 includes the computing device 5 receiving a glucose reading from the analyte sensor 3 and communicating with the DDS 4 to determine, recommend, and/or deliver one or more doses of insulin, glucagon, or other medicine.

The computing device 5 may communicate with the analyte sensor 3 and/or DDS 4 wirelessly (e.g., via Bluetooth, low energy Bluetooth, near-field communication, Infrared, WLAN, or other RF technology) or through a wired connection (e.g., IEEE 1394, Thunderbolt, Lightning, DVI, HDMI, Serial, Universal Serial Bus, Parallel, Ethernet, Coaxial, VGA, PS/2). In some cases, one or more functions of the computing device 5, analyte sensor 3, and/or DDS 4 are integrated into one or two devices. For example, the functionality of the computing device 5 can be performed by the analyte sensor 3 and/or the DDS 4 such that the analyte sensor 3 and DDS 4 communicate directly to each other. In some cases, the DDS 4 is a fully integrated device, which includes all functionality needed to test an analyte level, determine a recommended dose of a medicine based on the analyte level, and deliver the recommended dose.

The computing device 5 can be any suitable computing device, such as a desktop computer, laptop, tablet, smartphone, wearable computer, a portable medical controller, other mobile or handheld computing device, or a microprocessor integrated into the DDS 4 and/or analyte sensor 3. In some cases, the computing device 5 is a specialized, application-specific computing device. In some cases, the computing device 5 includes one or more user input elements, for example, one or more buttons, keys, dials, switches, touchscreens, etc., for modulating a function of the computing device 5. In some cases, the computing device 5 includes one or more output elements, for example, one or more audible alarms, tactile feedback, visual indicators such as lights, display screens, etc. In some cases, the computing device can wirelessly communicate with a separate device that includes a user interface.

The computing device 5 includes a processor and memory. The memory can include non-volatile memory (i.e., long-term persistent storage) in the form of mass storage, such as a disk/hard drive or flash memory. The computing device 5 may also include volatile memory (e.g., RAM). In some cases, system instructions are stored on the non-volatile memory, including a first set of instructions for performing one or more first feedback loops and a second set of instructions for performing a second feedback loop. In some cases, the computing device 5 includes instructions for calculating one or more basal or bolus doses of insulin; selecting one or more modes of operation; sending or receiving one or more inputs or instructions, for example, from the system components, a clinician, or a remote server; receiving or storing logged data from the first plurality of feedback loops; and/or modifying one or more system components or operating parameters.

As shown in FIGS. 1A and 1B, the system 2 can include a DDS 4. The DDS 4 is configured and programmed to deliver one or more doses of one or more medicines, for example, insulin and/or glucagon, to a patient, for example, to regulate glucose levels or to more closely align an actual basal profile relative to a target basal profile. In some cases, the DDS 4 can be a syringe, injection pen, and/or infusion pump. In some cases, system 2 provided herein can include multiple DDSs 4 and/or multiple analyte sensors 3. Glucose levels in a patient can vary temporally (e.g., hour to hour, day to day, week to week, and month to month) depending on the patient's activity level, hormones, meal composition and/or timing, stress, baseline metabolic function, and/or a wide variety of other parameters. To regulate glucose levels, the DDS 4 may be configured and/or manually used to deliver a basal dose of insulin (i.e., a near continuous delivery of small amounts of insulin) to offset the user's background metabolic needs for insulin availability and/or one or more bolus doses of insulin (e.g., rapid-acting or short-acting insulin) to counteract the effects of events, for example, meals consumed by the patient.

As shown in FIG. 1B, the system 2 can further include a remote computer system 7 that is accessed by the computing device 5 over one or more networks 6 (e.g., internet, intranet, local area network (LAN), wide area network (WAN), virtual private network (VPN), wireless network, mobile data network, or any combinations thereof). The remote computer system 7 can include one or more computing devices, such as one or more computer servers. One or more inputs (e.g., a timing of a meal, a size of a meal, a quantity of carbohydrates in a meal, a dose of insulin, a blood glucose level, a timing of an activity, an intensity of an activity, a desired aversion to hypoglycemia, one or more insulin absorption profiles, one or more carbohydrate absorption profiles, a circadian rhythm, one or more insulin-to-carbohydrate ratios, one or more insulin sensitivity factors, one or more blood glucose levels, one or more temporal factors, one or more diagnostic markers, one or more hormone levels, and/or one or more basal insulin profiles) may be sent to, stored on, and/or received from the remote computer system 7 and shared with the computing device 5. In some cases, the computing device 5 may transfer, upload, or otherwise transmit data from the analyte sensor 3 and/or DDS 4 to the remote computer system 7, for example, to be evaluated by a healthcare provider or to update the parameters and models. For example, the computing device 5 may store locally one or more inputs from the analyte sensor 3 and/or DDS 4 when the remote computer system 7 is unavailable (e.g., due to a poor or absent network connection).

In some cases, access to a remote computer system 7 may further be used for initial provisioning (e.g., uploading parameters and models) of the computing device 5. For example, a healthcare professional may link patient-identifying information (e.g., a patient's name, birthdate, social security number, health insurance number, phone number, email address, unique user identification code, etc.) identifying a patient to a set of administration parameters selected by a healthcare professional for the patient. The healthcare professional computing device used by the healthcare professional is directly or indirectly connected to a network and includes a screen displaying a graphical user interface configured to receive as inputs from the healthcare professional: patient-identifying information identifying a patient, and a set of administration parameters selected by the healthcare professional for the patient.

A set of administration parameters can, in some cases, be uploaded and/or stored with the patient-identifying information on the remote computer system 7. In some cases, the remote computer system 7 may receive a user input (e.g., a password, patient-identifying information, a patient-specific hyperlink, a captured QR code, a scanned bar code, an RFID tag, an alphanumeric key, etc.) from a patient computing device 5, such that the user input identifies or authenticates the patient computing device 5 as an authorized device associated with the patient (e.g., identified by the patient-identifying information). In some cases, the remote computer system 7 further identifies the set of administration parameters linked to the patient-identifying information and automatically transmits the set of administration parameters to the patient computing device 5. The administration parameters are accessible by, and influence the operation of, the DDS 4 and/or analyte sensor 3 in communication with the patient computing device 5, as shown in FIG. 1B. For example, the administration parameters may influence the operation of the DDS 4 and/or analyte sensor 3 by specifying a target amount of medicine to deliver; a frequency of delivery; and/or conditions, constraints, or algorithms for deviating a medicine administration from the target amount of medicine based on inputs from an analyte sensor 3 or based on user notification (e.g., input indicative of exercise or of a meal).

In some cases, the administration parameters are single values or ranges of values for one or more of: a total daily dose of insulin, a target basal quantity of insulin, a target basal insulin profile, an insulin sensitivity factor, an insulin-carbohydrate ratio, an insulin absorption profile, and/or a carbohydrate absorption profile. Further, in some cases, the administration parameters are inputs to a plurality of modes of operation stored on and executed by the patient computing device 5.

Figure 2:
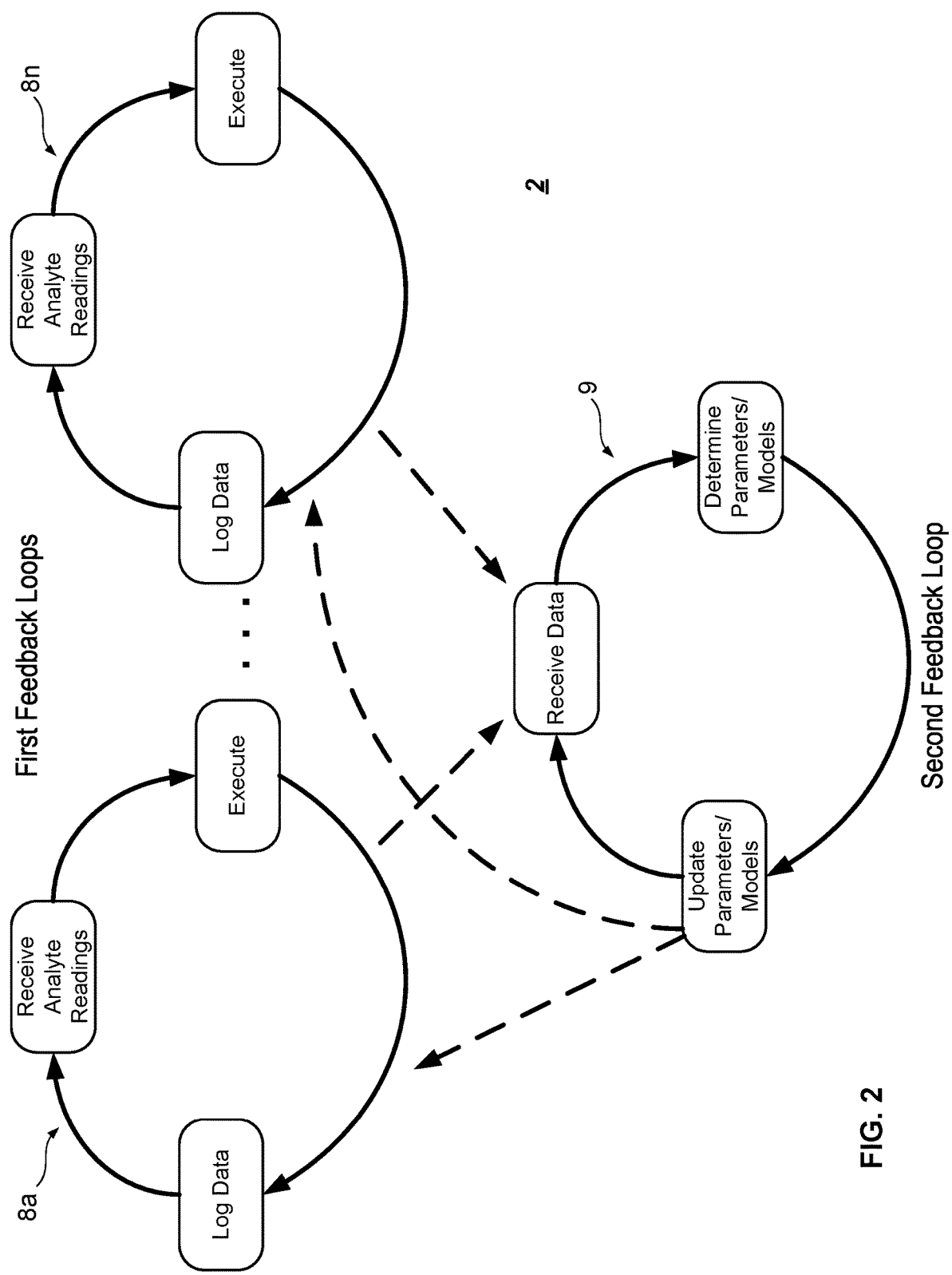
FIG. 2 illustrates a schematic diagram of an example feedback control system for diabetes management.

In some cases, as shown in FIG. 2, the example system 2 for diabetes management can include one or more first feedback loops 8a-8n and a second feedback loop 9. The feedback loops 8-9 manage real time insulin needs in response to user activities and glucose levels and data collection for a user and to individualize or tailor a therapy program to the user across various independent real time feedback loops.

A person with diabetes typically uses a combination of feed-forward control and feedback control in an attempt to maintain target therapeutic levels of blood glucose. Typically, the standard of care is so-called, open-loop therapy, where the individual with diabetes or a caregiver is required to make the decisions for both feed-forward and feedback control mechanisms. For example, when a person with diabetes delivers a bolus of insulin to counteract an upcoming meal he or she is using some pre-determined therapeutic parameters (e.g., carbohydrate ratio) combined with an estimate of the meal size in a feed-forward control action (i.e., the delivery is in anticipation of a future glucose excursion). An example of feedback control can occur when a person with diabetes combines the feedback from an unexpectedly high blood glucose reading with a pre-determined therapeutic parameter (e.g., insulin sensitivity factor) to calculate and deliver a correction bolus to counteract a blood glucose excursion that has already occurred.

As insulin delivery systems become more automated, some or all of the decisions related to these feed-forward and feedback control actions move from the individual with diabetes to a computing device, such as the computing device 5. Because different levels of automation may use different inputs and levels of component availability (e.g., a CGM), it is advantageous for an insulin delivery system (e.g., the system 2) to be able to operate in a variety of different levels of automation depending on what component inputs are currently available to the system and the desires of the individual who is supervising the system. The systems and methods described herein provide a seamless mechanism for maintaining consistency across various modes of automation. For the purposes of this discussion, a first feedback loop 8a-8n may include both feed-forward and feedback control actions.

Each of the plurality of first feedback loops 8a-8n represents a unique mode of operation and automation. In some cases, one of the first feedback loops 8a-8n is a manual mode. The manual mode may be the default mode of the system 2 when a computing device 5 is not connected to the analyte sensor 3 or DDS 4. The manual mode can include a patient manually controlling the therapy program including, for example, calculating and delivering proper insulin doses. In some examples of the manual mode, the patient monitors glucose levels with an analyte sensor 3 and administers insulin doses manually with a pen or syringe. In some cases, an insulin pen can be a smart insulin pen that can communicate a dosage of insulin directly to the system 2. In some cases, a user may input an amount and time of an insulin injection into a user interface for the computing device 5. In some cases, another of the first feedback loops 8a8-n includes fully automated control of the therapy program with the computing device 5, including calculating insulin doses and directing the DDS 4 to deliver the insulin doses. Other examples of first feedback loops 8a-8n are described further below.

In some cases, the plurality of first feedback loops 8a-8n share one or more underlying parameters and models. The shared parameters and models may include one or more of: one or more insulin absorption profiles, one or more carbohydrate absorption profiles, a circadian rhythm, one or more mealtimes, one or more insulin to carbohydrate ratios, one or more insulin sensitivity factors, one or more blood glucose levels, one or more temporal factors, one or more diagnostic markers, one or more hormone levels, and one or more basal insulin profiles. In some cases, there may be one or more sets of shared parameters and models to the first feedback loops 8a-8n that are applicable to a plurality of different periods in the day, week, month, or year. These multiple sets of parameters and models result from different insulin or medicine requirements arising from regular user activities or physiologic needs during those time periods.

In the various modes of the system 2, the first feedback loops 8a-8n are programmed to collect or receive an analyte sensor reading, determine an appropriate medicine dosing based on the analyte sensor reading and one or more of the parameters and models, administer the appropriate medicine dosing, and log data including the analyte sensor reading and the delivered medicine dosing. The means of collecting sensor readings, determining medicine dosing, administering the medicine, and logging the data may vary between the various modes (i.e., the various first feedback loops 8a-8n), but the basic steps remain the same. For example, in some modes, substantially all steps are performed manually, with the exception that upon a user entering the analyte sensor data and medicine dosing data into the computing device 5, the computing device 5 logs the data in memory and/or transmits the data to the remote computer system 7 for logging/storage. In another mode, the collection of sensor readings may be performed manually while one or more other steps are automated. In another mode, the medicine dosing may be performed manually while one or more other steps are automated. In another mode, medicine dosing determinations may be performed manually while one or more other steps are automated. In still another mode, each step may be automated.

Throughout the execution of various modes/first feedback loops 8a-8n, until a second feedback loop 9 (described in more detail below) is performed, the underlying parameters and models can remain constant and available for use in determining the appropriate medicine dosage. For example, the second feedback loop 9 can be performed intermittently, such as every half hour, once an hour, once every 6 hours, once every 12 hours, once every 24 hours, once a week, etc. In another example, the second feedback loop 9 may be performed by another device (e.g., the remote computer system 7, the computing device 5) that is different from the device performing the first feedback loops 8a-8n, so there may be times when the device performing the first feedback loops 8a-8n is not in communication with the other device performing the second feedback loops 9. During periods of time between performance of the second feedback loop 9, the underlying parameters and/or models that are used for the first feedback loops 8a-8n can remain constant (unchanged until updated by the second feedback loop 9).

In some cases, the plurality of first feedback loops 8a-8n operates at a first frequency or rate. The first frequency or rate may occur at a regular interval or an irregular or asynchronous interval based on a configuration of the computing device 5, the selected mode, a user configuration, or one or more underlying parameters and models. In some cases, the second feedback loop 9 operates at a second frequency or rate. The second frequency or rate may occur at a different interval than the first frequency. The second frequency or rate may occur at a regular interval or an irregular or asynchronous interval based on a configuration of the computing device 5 or a user configuration. In some cases, multiple iterations of one or more first feedback loops 8a-8n are operating sequentially during operation of the second feedback loop 9. The first and/or second frequency may depend on one or more events (e.g., meal times, exercise, stress, sleep, etc.), one or more temporal inputs, one or more user inputs, one or more factory or default settings of the computing device, or any other input.

One of the challenges of feedback control is the determination of the gains and dynamics of the system 2 that the automated control is attempting to manage. For a person with diabetes, these gains and system dynamics include insulin sensitivity factors, carbohydrate ratios, duration of insulin action, and other parameters. Some implementations allow the user to safely gain understanding of these parameters prior to initiating use of more automated feedback delivery modes, for example, by encouraging the user to use less automated modes of operation before more automated modes of operation.

The plurality of first feedback loops 8a-8n allow the shared parameters and models to be informed and individualized to a user by the use of less automated modes (e.g., manual mode or advisory mode) by the user. For example, upon initiation of a multi-mode system, it may be advantageous to have a user operate the system in a manual, first feedback mode for some period of time. In this example, doing so would allow the second feedback loop 9 to individualize the shared parameters and models to the user's physiology, prior to initiating a more automated mode (e.g., personal mode or adaptive mode). The ability to individualize the shared parameters and models and to tune the more automated delivery modes by first using the more manual first feedback modes 8a-8n is one of the benefits of at least some implementations of the systems and methods described herein.

In some cases, a user selects one of the plurality of first feedback loops 8a-8n for use or the system 2 selects one of the plurality of first feedback loops 8a-8n for use, for example, based on which system 2 components are connected to the computing device 5 (e.g., type of analyte sensor and/or DDS).

In some cases, the selected first feedback loop from the first feedback loops 8a-8n is substantially manual, such that a user analyzes the reading from the analyte sensor 3, determines a course of action, and executes the course of action. For example, the user may obtain a glucose value from a BGM or CGM, use that value combined with anticipated carbohydrate ingestion to estimate an amount of insulin to inject, which the user then uses an insulin pen to dispense.

In some cases, the selected first feedback loop from the first feedback loops 8a-8n may be partially automated, such that the computing device receives and analyzes the analyte reading, performs calculations based on the underlying parameters and models, and delivers a recommendation that the user then uses to determine and execute a course of action. For example, the blood glucose value from a BGM could pre-populate an insulin bolus calculator that the user uses to make a determination as to how much insulin should be delivered at a point in time.

In some cases, the selected first feedback loop from the first feedback loops 8a-8n is fully automated, such that the computing device 5 receives and analyzes the analyte reading, performs calculations based on the underlying parameters and models, and automatically triggers the system 2 to deliver a recommendation (e.g., exercise, sleep, eat, decrease stress, etc.) or an insulin or glucagon dose. An example of this type of feedback loop is an insulin pump that receives glucose values from a continuous glucose monitor every five minutes, makes a determination as to how much insulin to infuse over the next five minutes, and subsequently delivers said amount of insulin over that time period.

The plurality of first feedback loops 8a-8n may include a variety of modes, such as a manual mode, personalized mode, and an adaptive mode. Further, in some cases, the plurality of first feedback loops 8a-8n can include an advisory mode. Each of the plurality of first feedback loops 8a-8n can represent a unique level of automation. For example, the manual mode can be the lowest level of automation of the plurality of first feedback loops 8a-n while the adaptive mode is the highest level of automation of the plurality of first feedback loops 8a-8n.

In some cases, the computing device 5 will automatically transfer from a higher mode of automation to a lower mode of automation. The computing device 5 may trigger a notification or alert to the user indicating that the computing device 5 has transitioned its mode of operation and is now operating at a lower mode of automation. The notification or alert may include an audible alarm, a tactile alarm, a visible alarm such as a flashing light or a push notification, a text message, an email, an automated voice message, or any other type of notification format, for example, from a factory or default setting or preselected by a user. The computing device 5 may transfer to a lower mode of automation for a variety of reasons including: one or more system components (e.g., an analyte sensor 3 and/or DDS 4) is no longer communicatively coupled to the computing device 5; one or more system components has expired or reached the end of its useful life (e.g., requiring replacement or updating); one or more system components no longer has a power source (e.g., requires battery replacement or charging); the user has previously set a schedule for mode operation (e.g., different mode per time, day, week, month, activity, etc.); the user has failed to perform a required maintenance activity (e.g., change infusion site or calibration CGM); or some other condition that makes operating in the higher mode of automation unsafe.

Alternatively, in some cases, the computing device 5 transfers from a lower mode of automation to a higher mode of automation, for example, based on instructions from a user. The user may enable a higher mode of automation when all of the components required for the higher mode are available (e.g., a CGM and/or DDS 4 is communicatively coupled to the computing device 5) and/or there are no outstanding maintenance actions required by the user. The user may specify a mode of operation based on a temporal input or a desired level of control (e.g., manual versus automated) or therapeutic effect of the system (e.g., target blood glucose level or range). Alternatively, the computing device 5 may transfer from a lower mode of automation to a higher mode of automation automatically, for example, when a particular device such as an analyte sensor 3 and/or DDS 4 is detected to be communicatively coupled to the computing device 5. In some cases, automatically transferring from a lower mode of automation to a higher mode of automation is only enabled when the system properly prompts the user to switch from a lower mode of automation to a higher mode of automation.

Further, when switching between the modes of operation, the use of shared parameters and models across all first feedback loops allows for bumpless control transfer using the computing device 5, such that the control signal is not changed abruptly during switching (e.g., reduced or substantially absent discontinuities in control signal) due to the consistency of the underlying parameters and models used by the various modes. The ability for a user of a manual or semi-automated mode of operation to benefit from the individualization from use in a more automated mode of operation is another one of the significant benefits of at least some of the systems and methods described herein.

In some cases, the manual mode include manual configuration of a continuous basal delivery of insulin and one or more bolus doses of insulin by the DDS 4 (e.g., a syringe). In some cases, the computing device 5 operates in the manual mode when the analyte sensor 3 comprises a BGM or when the user specifies the manual mode of operation using one or more user input elements on the computing device 5. The computing device 5 in the manual mode collects data about analyte levels and one or more basal doses and one or more bolus doses of insulin. For example, a user manually collects one or more analyte sensor 3 readings using a BGM and test strip as described above. Further, the user calculates one or more basal and/or bolus doses of insulin and delivers them through a DDS 4. In some cases, the user inputs the blood glucose value(s) and/or insulin dosing value(s) into the computing device 5 using one or more user interface elements. In some cases, the BGM automatically transmits the blood glucose value(s) to the computing device 5 and in some cases the DDS 4 automatically transmits the insulin dosing value and/or insulin delivery timing to the computing device 5. The data can be collected, logged, and stored by the computing device 5 for later use by the second feedback loop 9.

In some cases, if the user is using an injection pen instead of a syringe, the basal or bolus dose dialed into the injection pen may be automatically tracked and transmitted to the computing device 5 to be logged and stored by the computing device 5. A mode with such functionality and system components can be referred to as an advisory mode. Further, in the advisory mode, the user may calculate, or have calculated, one or more recommended basal or bolus doses of insulin using, for example, an application stored on the computing device 5. In the advisory mode, the user can be responsible for administering the recommended basal or bolus dose.

In some cases, the computing device 5 operates in a personalized mode when the analyte sensor 3 is a CGM and the computing device 5 is connected to an automated DDS 4 (e.g., an insulin delivery system (IDS)) or when the user specifies the personalized mode of operation on the computing device 5 using one or more user interface elements. In some cases, a BGM is also included in the personalized mode in order to calibrate the CGM or in lieu of the CGM when the CGM is unavailable. The DDS 4 can automatically administer insulin to conform to a pre-set or pre-determined basal profile based on one or more inputs. The basal profile may be preset, for example, by a healthcare professional, and stored as a parameter or model. Alternatively, the computing device 5 may determine the basal profile based on other preset underlying parameters and models. The one or more inputs may include one or more of: a timing of a meal, a size of a meal, a quantity of carbohydrates in a meal, a dose of insulin, a blood glucose level, a timing of an activity, an intensity of an activity, a desired aversion to hypoglycemia, one or more insulin absorption profiles, one or more carbohydrate absorption profiles, a circadian rhythm, one or more insulin to carbohydrate ratios, one or more insulin sensitivity factors, one or more blood glucose levels, one or more temporal factors, one or more diagnostic markers, one or more hormone levels, and one or more basal insulin profiles.

Further, the computing device 5 in the personalized mode can be programmed to determine correction and/or prandial (i.e., mealtime) bolus doses of insulin based upon the shared parameters and models, one or more analyte sensor 3 readings, infusion data from the DDS 4, and/or one or more inputs. The DDS 4 may be configured to administer said correction and/or prandial bolus doses.

In some cases, the computing device 5 operates in the adaptive mode when the analyte sensor 3 is a CGM and the computing device 5 is connected to an automated DDS 4 (e.g., infusion pump). The adaptive mode may be a full automation mode. For example, the computing device 5 in the adaptive mode may treat a user-entered or parameterized basal profile as a target profile from which an actual delivery profile for the user may deviate or vary. The computing device 5 in the adaptive mode is programmed to adapt delivery of one or more basal doses and bolus doses of insulin based on at least one of: one or more analyte sensor 3 readings, infusion data from the DDS 4, or one or more inputs (e.g., a timing of a meal, a size of a meal, a quantity of carbohydrates in a meal, a dose of insulin, a blood glucose level, a timing of an activity, an intensity of an activity, a desired aversion to hypoglycemia, one or more insulin absorption profiles, one or more carbohydrate absorption profiles, a circadian rhythm, one or more insulin to carbohydrate ratios, one or more insulin sensitivity factors, one or more blood glucose levels, one or more temporal factors, one or more diagnostic markers, one or more hormone levels, one or more basal insulin profiles) to maintain the user within the target blood glucose range, and/or to adjust the user's blood glucose levels to arrive within the target blood glucose range. In some cases, the user's blood glucose levels may stabilize for a predetermined period of time, such that the computing device 5 does not require one or more analyte readings from the analyte sensor 3 to continue to maintain the user within the target range.

In some cases, the feedback control method used in an adaptive mode can be one of the following control methodologies: proportional; proportional-integral; proportional-integral-derivative; proportional-derivative; enhancements to proportional control that compensate for active insulin (insulin that has been dosed but has not yet acted on the blood glucose) in the individual; model-predictive-control (MPC); MPC based on physiological models; heuristic feedback methods; or any other feedback control mechanism known to those skilled in the art of feedback control.

In some cases, the mode of operation can be based on any combination of analyte sensor 3, DDS 4, and/or user input. For example, an additional or alternative mode of operation may include an injection pen and a CGM, a syringe and CGM, both a BGM and CGM and a DDS 4 (e.g., syringe, pen, pump), or two or more types of DDSs 4 and one or more types of analyte sensors 3.

Returning again to FIG. 2, the system for diabetes management also includes a second feedback loop 9. The second feedback loop 9 is programmed to collect data from one or more first feedback loops 8a-8n and individualize, to a user, the underlying shared parameters and models used by the plurality of first feedback loops 8a-8n. The underlying shared parameters and models may have initially been factory presets, or they may have been selected (either directly or indirectly through an algorithm for initiation) by the patient's physician, another healthcare professional, or the patient. The individualization tailors the system parameters and models to more closely match the user's underlying physiology, which allows the system 2 and the plurality of first feedback loops 8a-8n to operate more effectively over time. The data collected from the first feedback loops 8a-8n can include one or more of: a timing of a meal; a size of a meal; a quantity of carbohydrates in a meal; a time and quantity of a dose of insulin, glucagon, or other medicine; a blood glucose level; a timing of an activity; an intensity of an activity; a desired aversion to hypoglycemia; a target basal profile; a temporal input; a hormone level; and/or any other type of information. In some cases, the second feedback loop 9 includes accessing the logged data from the plurality of first feedback loops 8a-8n that operated during a pre-defined timeframe, determining if the shared parameters and models require updating based on the logged data from the pre-defined timeframe, and if the shared parameters and models require updating, updating the shared parameters and models for use in subsequent iterations of the plurality of first feedback loops 8a-8n, as will be described in further detail below.

Figure 3:
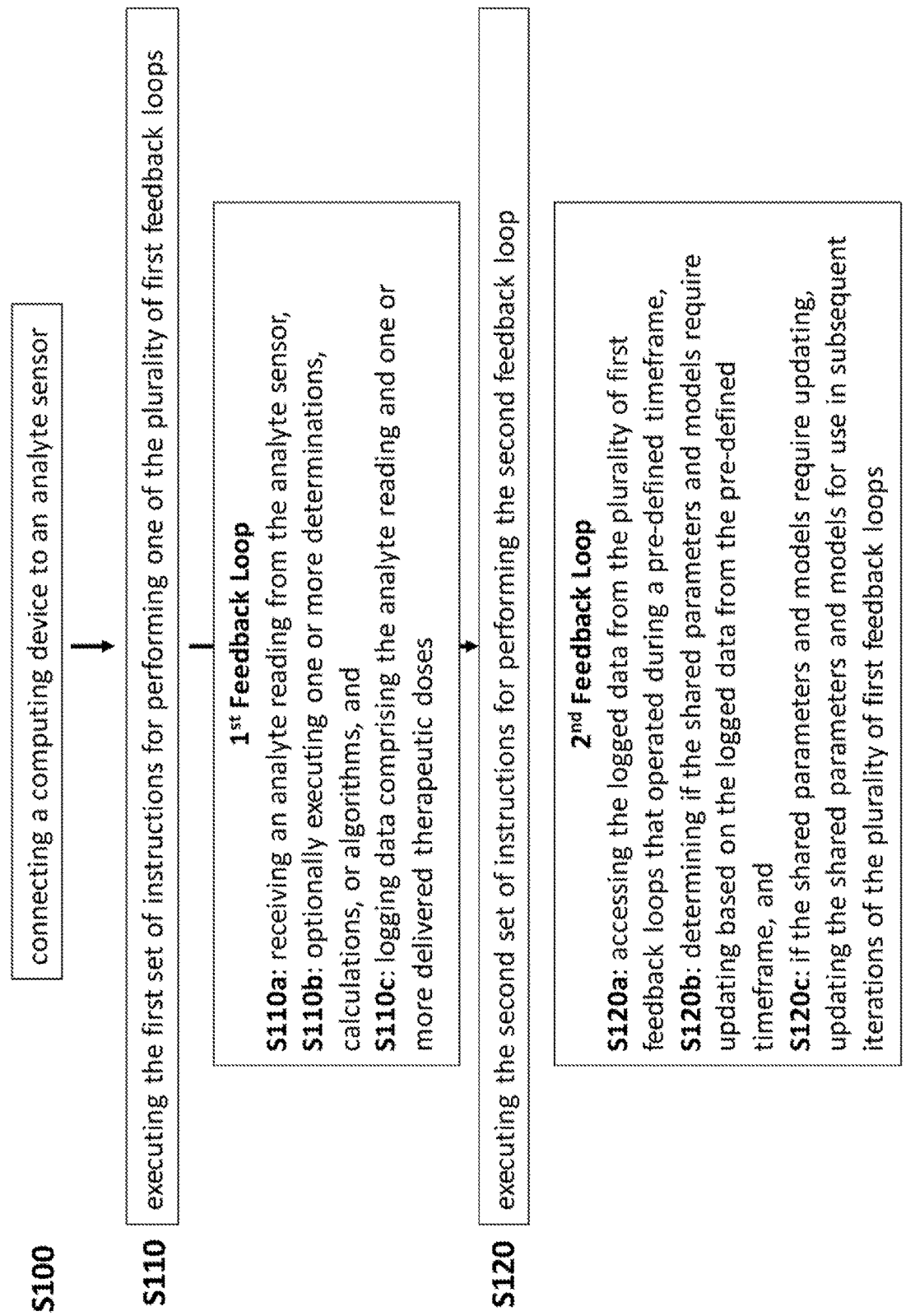
FIG. 3 is a flow chart of an example technique for automated diabetes management.

FIG. 3 is a flowchart that depicts an example technique for automating diabetes management. The example technique can be performed by components of the example system 2, such as the computing device 5, the DDS 4, the analyte sensor(s) 3, the remote computer system 7, and/or other components. The example technique includes connecting a computing device (e.g., the computing device 5) to an analyte sensor (e.g., the analyte sensor 3) S100, executing one of a plurality of first sets of instructions for performing one of the plurality of first feedback loops S110, and executing the second set of instructions for performing the second feedback loop S120. The technique can be programmed to guide a user from manual to semi-automatic or automatic (and in some cases, back to manual) management of diabetes and to individualize diabetes management to a user's physiology over time. The example technique can be used in the field of chronic disease management, but can additionally or alternatively be used for any suitable applications, clinical or otherwise. The example technique can be configured and/or adapted to be used for any suitable disease management or treatment plan.

As shown in FIG. 3, one implementation of the example technique for automation of diabetes management includes block S100, which recites connecting a computing device to an analyte sensor. Further, the computing device may be communicatively coupled to a DDS. For example, step S100 can include communicatively coupling the computing device 5 to the analyte sensor 3 and/or DDS 4. Connecting the computing device 5 to the analyte sensor 3 may include plugging the computing device 5 into the analyte sensor 3, wirelessly pairing the computing device 5 to the analyte sensor 3, and/or sharing electrical signals between a computing device 5 portion and an analyte sensor 3 portion, for example, if the computing device 5 and analyte sensor 3 are contained in a single device. In some cases, the computing device 5 is communicatively coupled to the analyte sensor 3 wirelessly (e.g., via Bluetooth, low energy Bluetooth, Infrared, WLAN, or other RF technology) or through a wired connection (e.g., IEEE 1394, Thunderbolt, Lightning, DVI, HDMI, Serial, Universal Serial Bus, Parallel, Ethernet, Coaxial, VGA, PS/2). Alternatively, in some cases, the computing device 5 and analyte sensor 3 and/or DDS 4 functionality is included within one integrated device.

As shown in FIG. 3, one implementation of the example technique for automation of diabetes management includes block S110, which recites executing one of a plurality of first sets of instructions for performing one of the plurality of first feedback loops. Performance of S110 can result in performance of the basic operations of the diabetes management system. For example, through the performance of the basic operations, the system 2 can collect and log data about a patient's tracked analyte levels and administered medicine doses. The system 2 may also calculate a recommended medicine dose to administer, and in some cases, administers said recommended medicine dose. Through performance of the first feedback loops 8a-8n and basic operation of the system 2, additional data may be collected and logged, including one or more of: a timing of a meal, a size of a meal, a quantity of carbohydrates in a meal, a timing of an activity, an intensity of an activity, a desired aversion to hypoglycemia, a target basal profile, a temporal input, a hormone level, and any other type of information.

In some cases, as shown in FIG. 3, the first set of instructions includes instructions for receiving an analyte reading from the analyte sensor S110a, optionally executing one or more determinations, calculations, or algorithms S110b, and logging data comprising the analyte reading and one or more delivered therapeutic doses S110c.

In some cases, receiving an analyte reading from the analyte sensor S110a refers to a user manually piercing his/her skin, depositing blood on a test strip for analysis by a BGM, and entering the blood glucose value detected by the BGM into the computing device 5. Alternatively, in some cases, receiving an analyte reading from the analyte sensor S110a refers to the user inputting an analyte reading from a CGM into the computing device 5. In other cases, receiving an analyte reading from the analyte sensor 3 refers to the computing device 5 automatically receiving an analyte reading from, for example, a CGM.

In some cases, each set of instructions associated with a unique first feedback loop (from the first feedback loops 8a-8n) includes instructions for the computing device 5 to operate in a unique automation mode, for example, a manual, advisory, personalized, adaptive mode, or any other type of mode, as described above. In some cases, executing one or more determinations, calculations, or algorithms S110b varies by automation mode, with one or more of the automation modes (and first feedback loops) programmed to perform a unique set of determinations, calculations, and/or algorithms. In some cases, executing one or more determinations, calculations, or algorithms S110b may include comparing the analyte reading to one or more of the following: a target or preferred value or range of values; an analyte reading from a previous time or date; a time and amount of a previous insulin or glucagon dose; a previous or future mealtime; or any other input. In some cases, executing one or more determinations, calculations, or algorithms requires reliance on and use of a set of underlying parameters and models.

In some cases, executing one or more determinations, calculations, or algorithms S110b includes running a proportional (P) controller algorithm, a proportional-integral (PI) controller algorithm, a proportional-derivative (PD) controller algorithm, or a proportional-integral-derivative (PID) controller algorithm. The controller algorithm functions to determine the present error (P), the accumulation of past or previous errors (I), and/or a prediction of future errors (D), based on current rate of change. Such a control algorithm may, in some cases, have additional inputs and terms in the control equation to account for insulin-on-board (i.e., insulin that has been dosed but has yet to act on the user's blood glucose level).

In some cases, executing one or more determinations, calculations, or algorithms S110b relies upon a model predictive control (MPC) algorithm. The MPC algorithm may be based upon physiologic models of one or more of the following: insulin transport, glucose transport, glucagon transport, and other medicine or hormone physiology. An MPC algorithm optimizes control actions to minimize the variation of future glucose values to some predetermined optimal set of glucose values according to some pre-determined function. The first control action from such an optimization can then be implemented by the controller and the process is started again from the beginning at the next control interval. There are many implementations of MPC control that would be applicable for a first feedback loop; the systems and methods provided herein are broadly applicable regardless of which MPC or other real-time control algorithm is chosen.

In some cases, the first set of instructions includes logging data including the analyte reading and one or more delivered therapeutic doses S110c. The logged data can be used by the second feedback loop (e.g., second feedback loop 9) to individualize the underlying shared parameters and models used by the plurality of first feedback loops (e.g., first feedback loops 8a-8n). The logged data may also include one or more of: a timing of a meal, a size of a meal, a quantity of carbohydrates in a meal, a time and amount of a dose of insulin or other medicine, a blood glucose level, a timing of an activity, an intensity of an activity, a desired aversion to hypoglycemia, one or more insulin absorption profiles, one or more carbohydrate absorption profiles, a circadian rhythm, one or more insulin to carbohydrate ratios, one or more insulin sensitivity factors, one or more blood glucose levels, one or more temporal factors, one or more diagnostic markers, one or more hormone levels, and/or one or more basal insulin profiles.

As shown in FIG. 3, one implementation of the depicted example technique for automation of diabetes management includes block S120, which recites executing the second set of instructions for performing the second feedback loop. Step S120 includes analyzing logged data from the plurality of first feedback loops and determining whether the underlying shared parameters and models for the plurality of first feedback loops should be updated. The maintained or updated shared parameters and models are then used in subsequent iterations of the plurality of first feedback loops.

In some cases, as shown in FIG. 3, the second set of instructions include: accessing the logged data from the plurality of first feedback loops that operated during a pre-defined timeframe S120a, determining if the shared parameters and models require updating based on the logged data from the pre-defined timeframe S120b, and if the shared parameters and models require updating, updating the shared parameters and models for use in subsequent iterations of the plurality of first feedback loops S120c.

In some cases, accessing the logged data from the plurality of first feedback loops includes retrieving the data from memory (e.g., volatile or non-volatile memory) on the computing device 5. The logged data is from a predefined time frame, for example, from a specified previous hour(s), day(s), week(s), or month(s) or any other time frame. For example, the plurality of first feedback loops 8a-8n can operate at a first frequency or rate. The first frequency or rate may occur at a regular interval or an asynchronous interval based on a configuration of the computing device or the mode, a user configuration, or one or more underlying parameters and models. In some cases, the second feedback loop 9 can operate at a second frequency or rate. The second frequency or rate may occur at a different interval than the first frequency. The second frequency or rate may occur at a regular interval or an asynchronous interval based on a configuration of the computing device or a user configuration. The first feedback loop operating at the first frequency may occur at a higher frequency (i.e., more frequently) than the second feedback loop operating at the second frequency (i.e., less frequently). In some cases, one or more of the plurality of first feedback loops are operating sequentially during one iteration of the second feedback loop. In some cases, multiple first feedback loops 8a-n can operate sequentially before one iteration of the second feedback loop 9. In some cases, the second feedback loop 9 can use the history of all first feedback loops 8a-8n operating in the recent past, which may include one or more first feedback loops 8a-8n. For example, if a first feedback loop 8a-8n operated from 12:00 AM to 6:00 AM, another iteration of a first feedback loop 8b (not shown) operated from 6:00 AM to 9:00 AM, and the second feedback loop 9 operates at 9:00 AM, the second feedback loop 9 may use the history from the first feedback loops 8a-8b that operated from 12:00 AM to 6:00 AM and from 6:00 AM to 9:00 AM.

In some cases, the second set of instructions can include determining if the shared parameters and models require updating based on the logged data from the pre-defined timeframe S120b. The techniques used for adjusting the shared parameters and models may include one or more of the following: feedback control via proportional, integral, derivative, or some combination of the three; model predictive control where the underlying model predicts how the parameters are expected to move over time; and/or other heuristic control algorithms where some form of feedback control is used to compare a current or historical value to a desired value and effectuating a change in a parameter in an attempt to reduce the future deviation of the two values. The value that the feedback control from the second feedback loop may, in some cases, act on include one or more of: one or more insulin absorption profiles, one or more carbohydrate absorption profiles, a circadian rhythm, one or more insulin to carbohydrate ratios, one or more insulin sensitivity factors, one or more target blood glucose levels, one or more temporal factors, one or more diagnostic markers, one or more hormone levels, and one or more basal insulin profiles, and/or other parameters that may be helpful or used by a first feedback loop. The second feedback loop 9 may act on a substantially different set of parameters than those listed above, in some cases, where the first feedback loops are parameterized with different variables than the current standard of diabetes care. Other implementations and combinations are also possible.

Referring to S120b in FIG. 3, a few scenarios are provided as non-limiting examples of how this may be embodied into the system 2. For example, if an analyte reading of a user is consistently above or below a target of the user, the basal profile, insulin to carbohydrate ratio and/or insulin sensitivity factor may be updated so that the user receives more or less insulin, respectively, to more accurately achieve the target or preferred blood glucose level. As another example, if a user consistently eats a meal at 12:00 PM, the underlying parameters and models may be updated to ensure that the user receives an increase in insulin dosing around 12:00 PM and/or a reminder for missed meal notifications shortly after 12:00 PM. In some cases, the logged data may be analyzed for patterns via, for example, machine learning algorithms, so that the underlying parameters and models may be updated to account for the observed pattern(s). As another example, in some cases, the parameters and models may include a range of acceptable basal insulin profiles and a range of acceptable insulin doses and dose frequencies. If the first feedback loop 8a must repeatedly administer or instruct administration of doses and dose frequencies at an upper or lower bound of what is acceptable in order to achieve the target glycemic range, the system 2 may identify that the underlying parameters and models require updating and raise or lower the bounds, respectively, such that bounds are no longer constraining delivery in the first feedback loop 8a.

In some cases, if the shared parameters and models need to be update, the second set of instructions can include updating the shared parameters and models for use in subsequent iterations of the plurality of first feedback loops S120c. In some cases, the shared parameters and models are updated to increasingly individualize the shared parameters and models to a user's underlying physiology and/or regular activity. Over time, a user may experience substantially automatic control or management of his/her diabetes, such that the user does not need to calculate insulin to carbohydrate ratios or insulin doses, or manually calculate or deliver insulin doses during periods of time.

In some cases, the updating of one or more of the shared parameters and models may be constrained by a pre-determined range of values. In such an implementation, the shared parameters and models may be updated within the pre-determined range of values automatically. In such instances, if the parameters and models need to be updated beyond or outside of the pre-determined range of values, an alert or notification may be sent and a person may be required to acknowledge and approve such change prior to it being effected by the second feedback loop. The person may be the user of the system 2, the user's clinician, or another member of the user's health care team. In some such instances, the parameters and models may not be updated until the person redefines or modifies the new parameter or model and approves the desired change.

In some cases, the patient's clinician or other health care provider may need to approve a change beyond a pre-determined range of values. In such cases, updating the shared parameters and models includes: generating an alert that the parameters and models require updating, and waiting for, and receiving, updated parameters and models. In some cases, the computing device 5 automatically generates the alert and displays it to a patient for forwarding to a health care provider. In other cases, the computing device 5 automatically generates the alert and transmits it to a network-connected healthcare professional's computer. In such cases, the healthcare professional is able to access the patient's collected data, stored on a server, via the healthcare professional's computer. The healthcare professional may then enter user inputs into his/her computer to modify the parameters and models based on his or her review of the data. Such modifications can be transmitted to the remote computer system 7. In some cases, the updated parameters and models are pulled by, or automatically pushed to, the patient's computing device 5 where the patient may or may not be required to acknowledge the update for use in subsequent iterations of the first feedback loops. In some cases, all updated parameters and models reside within memory on the patient's computing device. In other cases, some of the parameters and models may reside on the remote computer system 7 and be accessed by the computing device 5 when needed. In other cases, all updated parameters and models are transmitted to the patient's computing device 5 and some such parameters and models are subsequently loaded onto the analyte sensor 3 and/or DDS 4.

In some cases, a method for automation of diabetes management includes notifying the user of one or more maintenance requirements. For example, the system 2 may notify the user that one or more components of the system 2 (e.g., the analyte sensor 3) requires replacement, one or more system components (e.g., the computing device 5 and/or remote computer system 7) need a software update or an upgrade, the DDS 4 reservoir needs to be refilled, the analyte sensor 3 needs calibration, or any other maintenance requirements.

Figure 4:
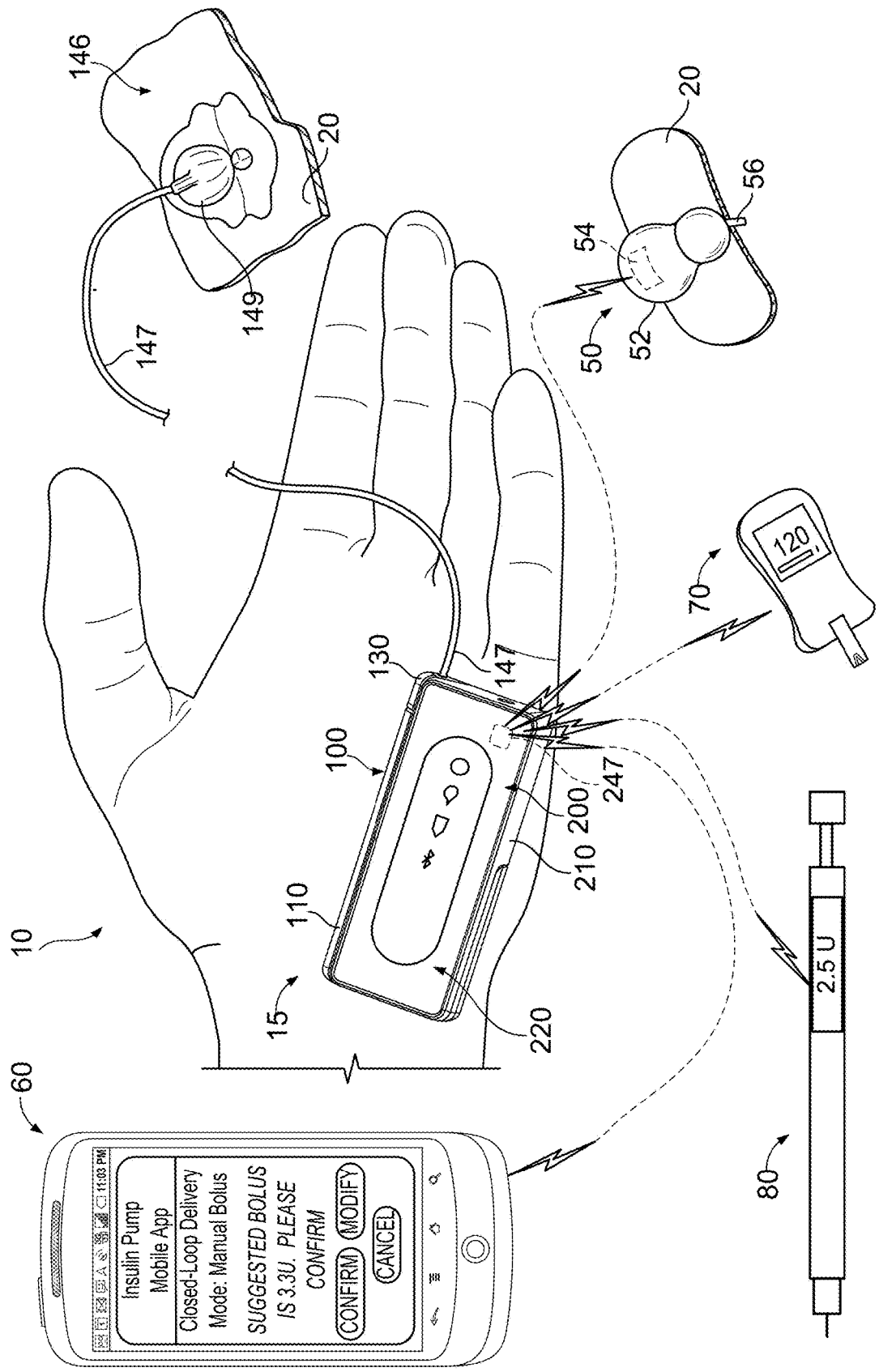
FIG. 4 is a perspective view of an example multi-modal medicine delivery system.

In some cases, a multi-modal medicine delivery system provided herein can be a multi-modal insulin delivery system including an insulin pump, an insulin pen and/or syringe, a CGM, a BGM, a computing device, and/or a remote user interface all in one system. FIGS. 4-12 provide examples of a DDS being an insulin pump and medicine delivered being insulin. The features that are described with regard to these FIGS. 4-12 can be extended to multi-modal medicine delivery system additionally/alternatively using other DDSs (other than insulin pumps) and to delivering other medicines (other than insulin). The infusion pumps described with regard to FIGS. 4-12 can be any of a variety of appropriate pump devices, including patch pumps and/or other commercially available pumps. For example, a multi-modal medicine delivery system 10 depicted in FIG. 4 can include a pump assembly 15 (example DDS 4) featuring a pump device 100 and a controller device 200, which can include a computing device. Optionally, the controller device 200 can be configured to releasably attach with the pump device 100. The controller device 200 can electrically communicate with the pump device 100 to control a drive system housed in the pump device 100 to dispense a medicine to a user (e.g., through a tube 147 of an infusion set 146 in this example). When the controller device 200 and the pump device 100 are assembled together, the user can (in some cases) conveniently wear the multi-modal medicine delivery system 10 on the user's skin under clothing, in a pouch clipped at the waist, or in the user's pocket while receiving the fluid dispensed from the pump device 100. Although FIG. 4 is shown with the controller device 200 being part of pump assembly 15, other implementations use a controller device or computing device that is separate from a pump assembly. In some cases, the controller device can be a remote controller device (e.g., a personal computer, a smartphone, or any of the other computing devices discussed above in association with FIGS. 1-3). In some cases, a multi-modal medicine delivery system provided herein may lack a pumping device and a user can administer insulin with a pen or syringe.

Briefly, in use, the pump device 100 in this example is configured to removably attach to the controller device 200 in a manner that provides a secure fitting, an overall compact size, and a reliable electrical connection. For example, as described in more detail below in connection with FIG. 5, the controller device 200 can include a controller housing 210 having a number of features that mate with complementary features of the pump housing structure 110. In such circumstances, the controller device 200 can removably attach with the pump device 100 in a generally side-by-side configuration. The compact size permits the pump assembly 15 to be discrete and portable. The controller device 200 can receive user input for purposes of operating the multi-modal medicine delivery system 10. In some cases, as described further below in connection with FIGS. 7-10, the pump assembly 15 can be configured (e.g., appropriately designed and programmed) to operate in any of a plurality of delivery modes while in parallel using a secondary feedback loop to determine updates to information (e.g., user-specific dosage parameters, user-specific dosage models, other settings (e.g., the user's insulin sensitivity, the user's carb ratio, or other settings)). For example, the controller device 200 can be configured to operate the multi-modal medicine delivery system 10 according to a closed-loop delivery mode, an open-loop delivery mode, and/or other delivery modes while at the same time using a secondary feedback loop to analyze data obtained for the delivery modes being used to operate the multi-modal medicine delivery system 10 and to provide updates to information used by the delivery modes. For instance, during operations under the closed-loop delivery mode, the controller device 200 can be configured to provide data (e.g., blood glucose readings, delivered dosages) obtained during operation under the closed-loop delivery mode to a secondary feedback loop, which can determine, store, and provide one or more user-specific settings, such as a user's personal dosage parameters, which can be subsequently used during current and future closed-loop operation (and/or during other delivery modes, such as open-loop delivery modes).

Still referring to FIG. 4, the multi-modal medicine delivery system 10 may optionally include any or a combination of a glucose monitoring device 50, a mobile computing device 60 (e.g., a smartphone configured to execute a mobile application associated with the pump assembly 15), a blood glucose meter 70, and a bolus adminstering device 80 in communication with the pump assembly 15 for the purpose of supplying data indicative of the user's blood glucose level, the user's dosage information, or other information to the controller device 200. As described above, in some cases, the infusion pump assembly 15 may not be used but one or more of the other devices (e.g., CGM, BGM, connected bolus administering device 80) can communicate directly to the mobile computing device 60 and/or other user interface device (e.g., other type of computing device). For example, a person could use closed loop system for a while and then take a "pump vacation" while on holiday. While on holiday, the person could just use a BGM and the connected bolus adminstering device 80 (e.g., pen) that operate using the parameters that were determined by the second feedback loop during other modes (e.g., pump open and closed loop modes). In another example, there could be no pump at all: the use of the connected bolus adminstering device 80 and BGM and/or CGM could generate data for the second feedback loop that may be used with the system 10.

In some cases, as described further below in connection with FIG. 7A, the controller device 200 (and/or other devices that are part of the system 10) can operate in any of a plurality of different delivery modes, which can generate and provide data to a secondary feedback loop running in parallel that can receive, from the secondary feedback loop, updated parameters, settings, and/or models for dosage delivery that are specific to the user. For example, as described further below in connection with FIG. 7B, the controller device 200 (and/or other devices that are part of the system 10) can run a secondary feedback loop in parallel with and across multiple different delivery modes that are programmed to determine and provide updates to user-specific parameters, settings, and/or models for dosage delivery based on data from operation under the multiple different delivery modes. Optionally, as describe further below in connection with FIG. 7C, the controller device 200 (and/or other devices that are part of the system 10) can determine when to transition, automatically and/or manually, between delivery modes. In some cases, as described further below in connection with FIGS. 8A and 8B, the controller device 200 can operate in a closed-loop delivery mode by providing data (e.g., blood glucose readings, delivered dosages, food intake information, user activity information, and the like) to a secondary feedback loop, receiving updated user-specific dosage parameters (and other information affecting dosage determinations) from the secondary feedback loop, and determining and delivering dosages using the updated information. Additionally or alternatively, as described further below in connection with FIG. 9, the controller device 200 can also operate in an open-loop delivery mode (e.g., based upon user selection of a predetermined basal rate dispensation schedule and manually selected bolus amounts) in which the controller device 200 also provides data (e.g., blood glucose readings, delivered dosages, user inputs) to the secondary feedback loop, receiving updated user-specific dosage parameters (and other information affecting dosage determinations) from the secondary feedback loop, and determining bolus dosages using the updated information.

The glucose monitoring device 50 can include a housing 52, a wireless communication device 54, and a sensor shaft 56. The wireless communication device 54 can be contained within the housing 52 and the sensor shaft 56 can extend outward from the housing 52. In use, the sensor shaft 56 can penetrate the skin 20 of a user to make measurements indicative of characteristics of the user's blood (e.g., the user's blood glucose level or the like). In some cases, the sensor shaft 56 can measure glucose or another analyte in interstitial fluid or in another fluid and correlate that to blood glucose levels. In response to the measurements made by the sensor shaft 56, the glucose monitoring device 50 can employ the wireless communication device 54 to transmit data to a corresponding wireless communication device 247 housed in the pump assembly 15. In some cases, the glucose monitoring device 50 may include a circuit that permits sensor signals (e.g., data from the sensor shaft 56) to be communicated to the wireless communication device 54. The wireless communication device 54 can transfer the collected data to the controller device 200 (e.g., by wireless communication to the communication device 247). Alternatively, the glucose monitoring device 50 can employ other methods of obtaining information indicative of a user's blood characteristics and transferring that information to the controller device 200. For example, an alternative monitoring device may employ a micropore system in which a laser porator creates tiny holes in the uppermost layer of a user's skin, through which interstitial glucose is measured using a patch. In the alternative, the monitoring device can use iontophoretic methods to non-invasively extract interstitial glucose for measurement. In other examples, the monitoring device can include non-invasive detection systems that employ near IR, ultrasound or spectroscopy, and particular implementations of glucose-sensing contact lenses. Invasive methods involving optical means of measuring glucose could also be added. In yet another example, the monitoring device can include an optical detection instrument that is inserted through the skin for measuring the user's glucose level. Furthermore, it should be understood that in some alternative implementations, the glucose monitoring device 50 can be in communication with the controller device 200 or another computing device via a wired connection.

In some cases, the multi-modal medicine delivery system 10 can further include the mobile computing device 60 that can communicate with the controller device 200 through a wireless and/or wired connection with the controller device 200 (e.g., via a Bluetooth wireless communication connection in this particular implementations). In some cases, mobile computing device 60 communicates wirelessly with other elements of the system 10. Mobile computing device 60 can be any of a variety of appropriate computing devices, such as a smartphone, a tablet computing device, a wearable computing device, a smartwatch, a fitness tracker, a laptop computer, a desktop computer, and/or other appropriate computing devices. In some cases where there is no computing device that is part of a pump, the mobile computing device 60 can receive and log data from other the other elements of system 10. In some cases, a user can input relevant data into mobile computing device 60. In some cases where a pump assembly 15 includes controller device 200, the mobile computing device 60 can receive and log data that is collected by the controller device 200, such as blood glucose readings, dosage delivery information, and also can receive user inputs (e.g., user-selected parameters to be stored on the controller device 200, user-confirmation of bolus dosages (described below), and others). In some cases, mobile computing device 60 can be used to transfer data from controller device 200 to the cloud. In some cases, the mobile computing device 60 provides a user interface (e.g., graphical user interface (GUI), speech-based user interface, motion-controlled user interface) through which users can provide information to control operation of the controller device 200 and the multi-modal medicine delivery system 10. For example, the mobile computing device 60 can be a mobile computing device running a mobile app that communicates with the controller device 200 over short-range wireless connections (e.g., BLUETOOTH connection, Wi-Fi Direct connection) to provide status information for the multi-modal medicine delivery system 10 and allow a user to control operation of the multi-modal medicine delivery system 10 (e.g., toggle between delivery modes, adjust settings, log food intake, confirm/modify/cancel bolus dosages, and the like).

For the specific system depicted in FIG. 4, various configurations for which devices (e.g., the controller device 200 and/or the mobile computing device 60, other remote computing devices/systems that are in communication with the mobile computing device 60) perform multiple delivery modes and a secondary feedback loop for the multi-modal medicine delivery system 10 are possible. For example, the controller device 200 may be programmed to transmit data to the mobile computing device 60 and to deliver medicine based on control signals from the mobile computing device 60, which can be programmed to perform the multiple delivery modes and a secondary feedback loop for the multi-modal medicine delivery system 10 using the data received from the controller device 200 and by transmitting appropriate control signals to the controller device. In another example, the controller device 200 can be programmed to perform operations to implement the multiple delivery modes and to transmit data to the mobile computing device 60, which can be programmed to perform a secondary feedback loop based on the data and to provide updated delivery information (e.g., user-specific dosage parameters, dosage models) to the controller device 200 to use for performing the multiple delivery modes. In a further example, the controller device 200 can be programmed to perform both the multiple delivery modes and a secondary feedback loop for the multi-modal medicine delivery system 10, and the mobile computing device 60 can be programmed to perform other operations for the system 10, such as storing data and/or providing an enhanced user interface. In another example, pump assembly 15 can lack a controller device 200, and mobile computing device 60 can control the pump assembly 15. In another example, pump assembly 15 can be completely lacking from some systems, and mobile computing device 60 can serve as the computing device for making recommendations and/or controlling a pump later added to the system. Other configurations are also possible, including having the processing of one or more of these features (e.g., operations to implement multiple delivery modes, secondary feedback loops) being performed by one or more remote computer systems that are in communication with the mobile computing device 60 and/or the controller device 200.

Still referring to FIG. 4, the multi-modal medicine delivery system 10 may optionally communicate with the blood glucose meter 70 in addition to (or as an alternative to) the glucose monitoring device 50. For example, one or more test strips (e.g., blood test strips) can be inserted into a strip reader portion of the blood glucose meter 70 and then receive blood to be test for characteristics of the blood. In some cases, the glucose meter device is configured to analyze the characteristics of the user's blood and communicate (e.g., via a Bluetooth wireless communication connection) the information to the controller device 200. In some cases, a user can manually input a glucose meter reading. The blood glucose meter 70 can be manually operated by a user and may include an output subsystem (e.g., display, speaker) that can provide the user with blood glucose readings that can be subsequently entered into the controller or user interface to collect the data from an unconnected BGM into the system. The blood glucose meter 70 may be configured to communicate data (e.g., blood glucose readings) obtained to the controller device 200 and/or other devices, such as the mobile computing device 60. Such communication can be over a wired and/or wireless connection, and the data can be used by the controller device 200 and/or the mobile computing device 60 to perform multiple delivery modes and/or a secondary feedback loop for the multi-modal medicine delivery system 10.

Optionally, the multi-modal medicine delivery system 10 may include a bolus administering device 80 (e.g., syringe, an insulin pen, a smart syringe with device communication capabilities, or the like) through which bolus dosages can be manually administered to a user. The dosage for a bolus to be administered using the bolus administering device 80 can be determined as part of multiple delivery modes and a secondary feedback loop that are used to control the multi-modal medicine delivery system 10, and such dosage amounts can be output to a user via the user interface of the controller device 200 and/or the user interface of the mobile computing device 60. In some cases, the bolus administering device 80 can communicate through a wired and/or wireless connection with the controller device 200 and/or the mobile computing device 60. The bolus administering device 80 may be configured to output determined bolus dosages, to regulate the dosage delivery, to determine or recommend an actual bolus dose delivered to a user, and to communicate such information back to the controller device 200 and/or the mobile computing device 60.

In some cases, the pump assembly 15 can be pocket-sized so that the pump device 100 and controller device 200 can be worn in the user's pocket or in another portion of the user's clothing. In some circumstances, the user may desire to wear the pump assembly 15 in a more discrete manner. Accordingly, the user can pass the tube 147 from the pocket, under the user's clothing, and to the infusion site where the adhesive patch can be positioned. As such, the pump assembly 15 can be used to deliver medicine to the tissues or vasculature of the user in a portable, concealable, and discrete manner.

In some cases, the pump assembly 15 can be configured to adhere to the user's skin directly at the location in which the skin is penetrated for medicine infusion. For example, a rear surface of the pump device 100 can include a skin adhesive patch so that the pump device 100 can be physically adhered to the skin of the user at a particular location. In these cases, the cap device 130 can have a configuration in which medicine passes directly from the cap device 130 into an infusion set 146 that is penetrated into the user's skin. In some examples, the user can temporarily detach the controller device 200 (while the pump device 100 remains adhered to the skin) so as to view and interact with the user interface 220.

Figure 5:
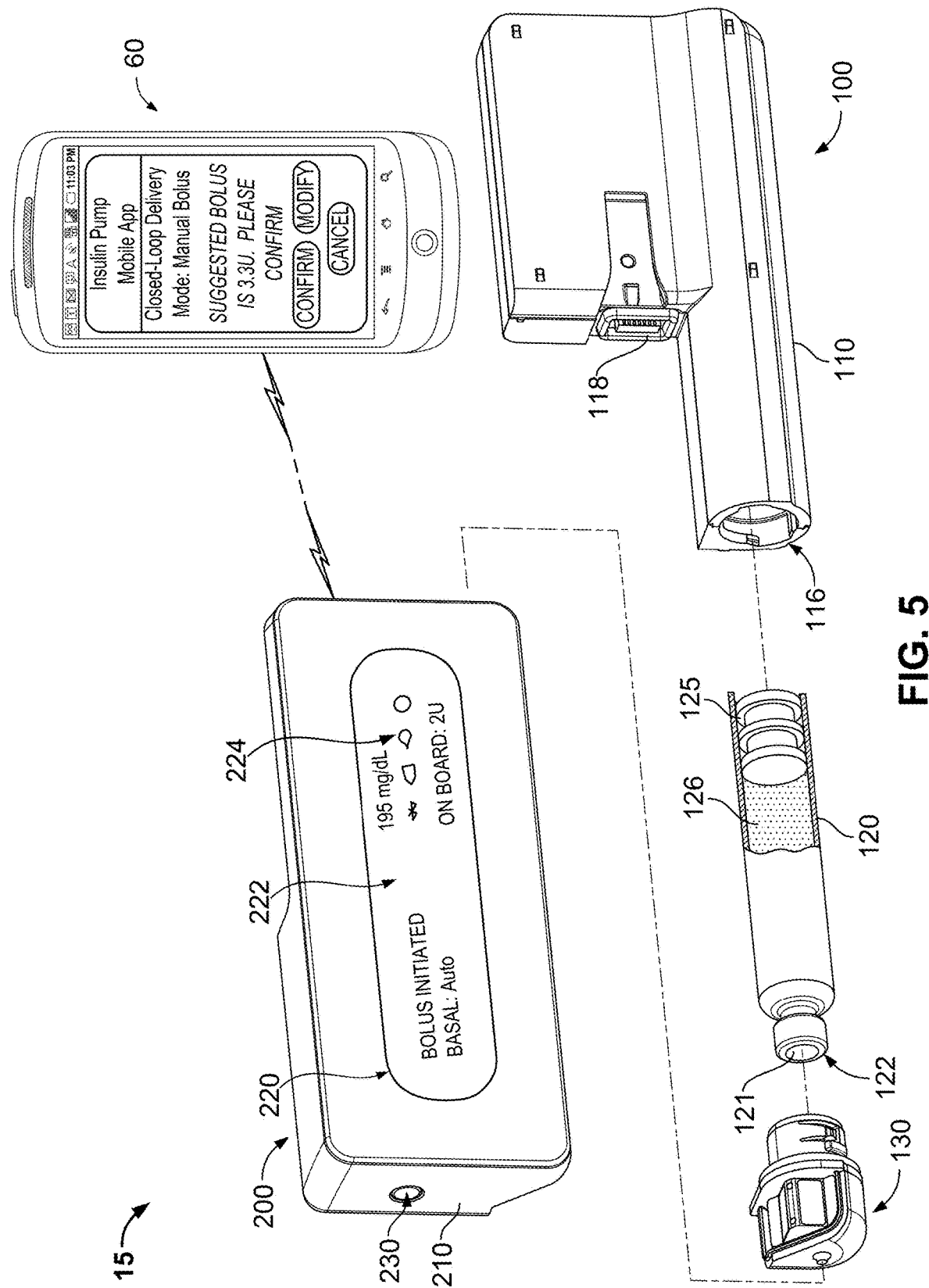
FIG. 5 is an exploded perspective view of an example multi-modal medicine delivery system.

Referring now to FIG. 5, the pump device 100 in this example includes a pump housing structure 110 that defines a cavity 116 in which a fluid cartridge 120 can be received. The pump device 100 also can include a cap device 130 to retain the fluid cartridge 120 in the cavity 116 of the pump housing structure 110. The pump device 100 can include a drive system (e.g., including a battery powered actuator, a gear system, a drive rod, and other items that are not shown in FIG. 5) that advances a plunger 125 in the fluid cartridge 120 so as to dispense fluid therefrom. In this example, the controller device 200 communicates with the pump device 100 to control the operation of the drive system. Optionally, the controller device 200 may be configured as a reusable component that provides electronics and a user interface to control the operation of the pump device 100. In such circumstances, the pump device 100 can be a disposable component that is disposed of after a single use. For example, the pump device 100 can be a "one time use" component that is thrown away after the fluid cartridge 120 therein is exhausted. Thereafter, the user can removably attach a new pump device (having a new fluid cartridge) to the reusable controller device 200 for the dispensation of fluid from a new fluid cartridge. Accordingly, the user is permitted to reuse the controller device 200 (which may include complex or valuable electronics, as well as a rechargeable battery) while disposing of the relatively low-cost pump device 100 after each use. Such a pump assembly 15 can provide enhanced user safety as a new pump device (and drive system therein) is employed with each new fluid cartridge. Additional and/or alternative implementations of the controller device 200 are also possible, including magnetic drive turbine (MDT) monolithic architecture pumps and/or omnipods.

The pump assembly 15 can be a medical infusion pump assembly that is configured to controllably dispense a medicine from the fluid cartridge 120. As such, the fluid cartridge 120 can contain a medicine 126 to be infused into the tissue or vasculature of a targeted individual, such as a human or animal patient. For example, the pump device 100 can be adapted to receive a fluid cartridge 120 in the form of a carpule that is preloaded with insulin or another medicine for use in the treatment of Diabetes (e.g., Exenatide (BY-ETTA®, BYDUREON®) and liraglutide (VICTOZA®) SYMLIN®, or others). Such a fluid cartridge 120 may be supplied, for example, by Eli Lilly and Co. of Indianapolis, Ind. Other examples of medicines that can be contained in the fluid cartridge 120 include: pain relief drugs, hormone therapy, blood pressure treatments, anti-emetics, osteoporosis treatments, or other injectable medicines. The fluid cartridge 120 may have other configurations. For example, the fluid cartridge 120 may comprise a reservoir that is integral with the pump housing structure 110 (e.g., the fluid cartridge 120 can be defined by one or more walls of the pump housing structure 110 that surround a plunger to define a reservoir in which the medicine is injected or otherwise received).

In some cases, the pump device 100 can include one or more structures that interfere with the removal of the fluid cartridge 120 after the fluid cartridge 120 is inserted into the cavity 116. For example, the pump housing structure 110 can include one or more retainer wings (not shown) that at least partially extend into the cavity 116 to engage a portion of the fluid cartridge 120 when the fluid cartridge 120 is installed therein. Such a configuration may facilitate the "one-time-use" feature of the pump device 100. In some cases, the retainer wings can interfere with attempts to remove the fluid cartridge 120 from the pump device 100, thus ensuring that the pump device 100 will be discarded along with the fluid cartridge 120 after the fluid cartridge 120 is emptied, expired, or otherwise exhausted. In another example, the cap device 130 can be configured to irreversibly attach to the pump housing structure 110 so as to cover the opening of the cavity 116. For example, a head structure of the cap device 130 can be configured to turn so as to threadably engage the cap device 130 with a mating structure along an inner wall of the cavity 116, but the head structure may prevent the cap device from turning in the reverse direction so as to disengage the threads. Accordingly, the pump device 100 can operate in a tamper-resistant and safe manner because the pump device 100 can be designed with a predetermined life expectancy (e.g., the "one-time-use" feature in which the pump device is discarded after the fluid cartridge 120 is emptied, expired, or otherwise exhausted).

Still referring to FIG. 5, the controller device 200 can be removably attached to the pump device 100 so that the two components are mechanically mounted to one another in a fixed relationship. In some cases, such a mechanical mounting can also form an electrical connection between the removable controller device 200 and the pump device 100 (for example, at electrical connector 118 of the pump device 100). For example, the controller device 200 can be in electrical communication with a portion of the drive system (show shown) of the pump device 100. In some cases, the pump device 100 can include a drive system that causes controlled dispensation of the medicine or other fluid from the cartridge 120. In some cases, the drive system incrementally advances a piston rod (not shown) longitudinally into the cartridge 120 so that the fluid is forced out of an output end 122. A septum 121 at the output end 122 of the fluid cartridge 120 can be pierced to permit fluid outflow when the cap device 130 is connected to the pump housing structure 110. For example, the cap device 130 may include a penetration needle that punctures the septum 121 during attachment of the cap device 130 to the housing structure 110. Thus, when the pump device 100 and the controller device 200 are mechanically attached and thereby electrically connected, the controller device 200 communicates electronic control signals via a hardwire-connection (e.g., electrical contacts along electrical connector 118 or the like) to the drive system or other components of the pump device 100. In response to the electrical control signals from the controller device 200, the drive system of the pump device 100 causes medicine to incrementally dispense from the fluid cartridge 120. Power signals, such as signals from a battery (not shown) of the controller device 200 and from the power source (not shown) of the pump device 100, may also be passed between the controller device 200 and the pump device 100.

Still referring to FIG. 5, the controller device 200 can include a user interface 220 that permits a user to monitor and (optionally) control the operation of the pump device 100. In this depicted example, the user interface 220 of the controller device 200 may not include physical buttons, but it includes at least a display device 222 and a collection of icons that can be illuminated to convey information regarding the current state of operation for the pump assembly 15. For example, the icons can indicate whether the pump assembly 15 is on, the current mode of operation (e.g., closed-loop mode, open-loop mode), whether there are pending notifications or other information for the user to review, whether user input is required, whether the controller device 200 is wirelessly connected with the mobile computing device 60 (or other computing devices), and/or other notifications. Optionally, the display screen of the user interface 220 may be in the form of a touch screen in which a touch-sensitive layer is positioned over the LCD screen component. Additionally or alternatively, the mobile computing device 60 may provide a more full-featured user interface for purposes of receiving user input (which is then communicated to the controller device 200 via the wireless communication connection) and providing more detailed information displays. For example, as described in more detail below, the user may view and interact with the user interface of the mobile computing device 60 (e.g., an interface of the mobile app configured to work with the pump assembly 15) to shuffle through a number of menus or program screens that show particular operational modes (e.g., closed-loop delivery mode and open-loop delivery mode), settings (e.g., user-specific dosage parameters) and data (e.g., review data that shows the medicine dispensing rate, the total amount of medicine dispensed in a given time period, the amount of medicine scheduled to be dispensed at a particular time or date, the approximate amount of medicine remaining in the fluid cartridge 120, or the like). In this alternative example, the user can adjust the modes and/or settings, or otherwise program the controller device 200 by touching one or more virtual buttons (or physical buttons) on the user interface of the mobile computing device 60. For example, the user may press one or more of the virtual buttons (or physical buttons) on the user interface of the mobile computing device 60 to change the operation of the multi-modal medicine delivery system 10 from a closed-loop delivery mode to an open-loop delivery mode. In some implementations, the display device 222 of the controller, the display of the mobile computing device 60, or both may also be used to communicate information regarding remaining battery life. Optionally, the controller device 200 may be equipped with additional components, such as one or more of the following: motion sensors (not shown), secondary light instruments 230, vibratory output devices (not shown), a microphone to obtain voice input, and the like.

In some alternative implementations, the user interface 220 can include be equipped with one or more user-selectable buttons so that the user can press one or more of the buttons to shuffle through a number of menus or program screens that show particular operational modes (e.g., closed-loop delivery mode and open-loop delivery mode), settings (e.g., user-specific dosage parameters) and data (e.g., review data that shows the medicine dispensing rate, the total amount of medicine dispensed in a given time period, the amount of medicine scheduled to be dispensed at a particular time or date, the approximate amount of medicine remaining in the fluid cartridge 120, or the like).

Referring again to FIGS. 4-5, the pump assembly 15 can be configured to be portable and can be wearable and concealable. For example, a user can conveniently wear the pump assembly 15 on the user's skin (e.g., skin adhesive) underneath the user's clothing or carry the pump device 100 in the user's pocket (or other portable location) while receiving the medicine dispensed from the pump device 100. The pump assembly 15 depicted in FIG. 4 as being held in a user's hand 5 so as to illustrate its size in accordance with some implementations. This example of the pump assembly 15 is compact so that the user can wear the portable pump assembly 15 (e.g., in the user's pocket, connected to a belt clip, adhered to the user's skin, or the like) without the need for carrying and operating a separate module. In such examples, the cap device 130 of the pump device 100 can be configured to mate with an infusion set 146. In general, the infusion set 146 can be a tubing system that connects the pump assembly 15 to the tissue or vasculature of the user (e.g., to deliver medicine into the tissue or vasculature under the user's skin). The infusion set 146 can include a flexible tube 147 that extends from the pump device 100 to a subcutaneous cannula 149 that may be retained by a skin adhesive patch (not shown) that secures the subcutaneous cannula 149 to the infusion site. The skin adhesive patch can retain the subcutaneous infusion cannula 149 in fluid communication with the tissue or vasculature of the user so that the medicine dispensed through the tube 147 passes through the subcutaneous cannula 149 and into the user's body. The cap device 130 can provide fluid communication between the output end 122 (FIG. 5) of the fluid cartridge 120 and the tube 147 of the infusion set 146.

In some cases, the pump assembly 15 can operate (during an open-loop mode, for example) to deliver insulin to the user by a predetermined schedule of basal dosages, manually selected bolus dosages, or a combination thereof. A basal rate of insulin can be delivered in an incremental manner (e.g., dispense 0.25 U every fifteen minutes for a rate of 1.0 U per hour) according to a previously scheduled delivery profile to help maintain the user's blood glucose level within a targeted range during normal activity, when the user is not consuming food items. The user may select one or more bolus deliveries, for example, to offset the blood glucose effects caused by food intake, to correct for an undesirably high blood glucose level, to correct for a rapidly increasing blood glucose level, or the like. In some circumstances, the basal rate delivery pattern may remain at a substantially constant rate for a long period of time (e.g., a first basal dispensation rate for a period of hours in the morning, and a second basal dispensation rate for a period of hours in the afternoon and evening). In contrast, the bolus dosages can be more frequently dispensed based on calculations made by the controller device 200 or the mobile computing device 60 (which then communicates to the controller device 200). For example, the controller device 200 can determine that the user's blood glucose level is rapidly increasing (e.g., by interpreting data received from the glucose monitoring device 50), and can provide an alert to the user (via the user interface 220 or via the mobile computing device 60) so that the user can manually initiate the administration of a selected bolus dosage of insulin to correct for the rapid increase in blood glucose level. In one example, the user can request (via the user interface of mobile computing device 60) a calculation of a suggested bolus dosage (e.g., calculated at the mobile computing device 60 based upon information received from the user and from the controller device 200, or alternatively calculated at the controller device 200 and communicated back the mobile computing device 60 for display to the user) based, at least in part, on a proposed meal that the user plans to consume.

The basal and bolus insulin dispensed into the user's body may act over a period of time to control the user's blood glucose level. As such, the user can benefit from the implementations of the multi-modal medicine delivery system 10 that can take into account different circumstances and information when determining a suggested amount of a basal or bolus dosage. For example, the mobile computing device 60 (or the controller device 200 in some cases) may be triggered to calculate a suggested bolus dosage in response to the user's food intake. When calculating the bolus dosage, however, the user may benefit if the mobile computing device 60 (or the controller device 200 in some cases) employed one or more user-specific dosage parameters that reflect the user's physiological response to insulin. In some cases, the mobile computing device 60 (or the controller device 200 in some cases) can employ the user-specific dosage parameters in combination with data indicative of the user's blood glucose level, historical food intake data previously submitted by the user, the user's insulin load, and the like to provide an accurate dosage calculation. Exemplary information that can be derived from the user's blood glucose information that can be used by the mobile computing device 60 (or the controller device 200 in some cases) in determining a bolus dosage can include the user's current blood glucose level, the rate of change in the user's blood glucose level, the $2^{nd}$ derivative of the user's blood glucose data, the shape and/or appearance of the user's blood glucose curve, or the like. In some cases, the mobile computing device 60 (or the controller device 200 in some cases) can use information from previously entered meals and previously delivered insulin dosages when calculating a suggested bolus dosage. In these examples, information regarding previously entered meals and previously delivered insulin dosages from 12 hours or more (e.g., 24 hours, 12 hours, 8 hours, 6 hours, 0.5 hours, or the like) can be used in the bolus dosage calculations.

Figure 6:
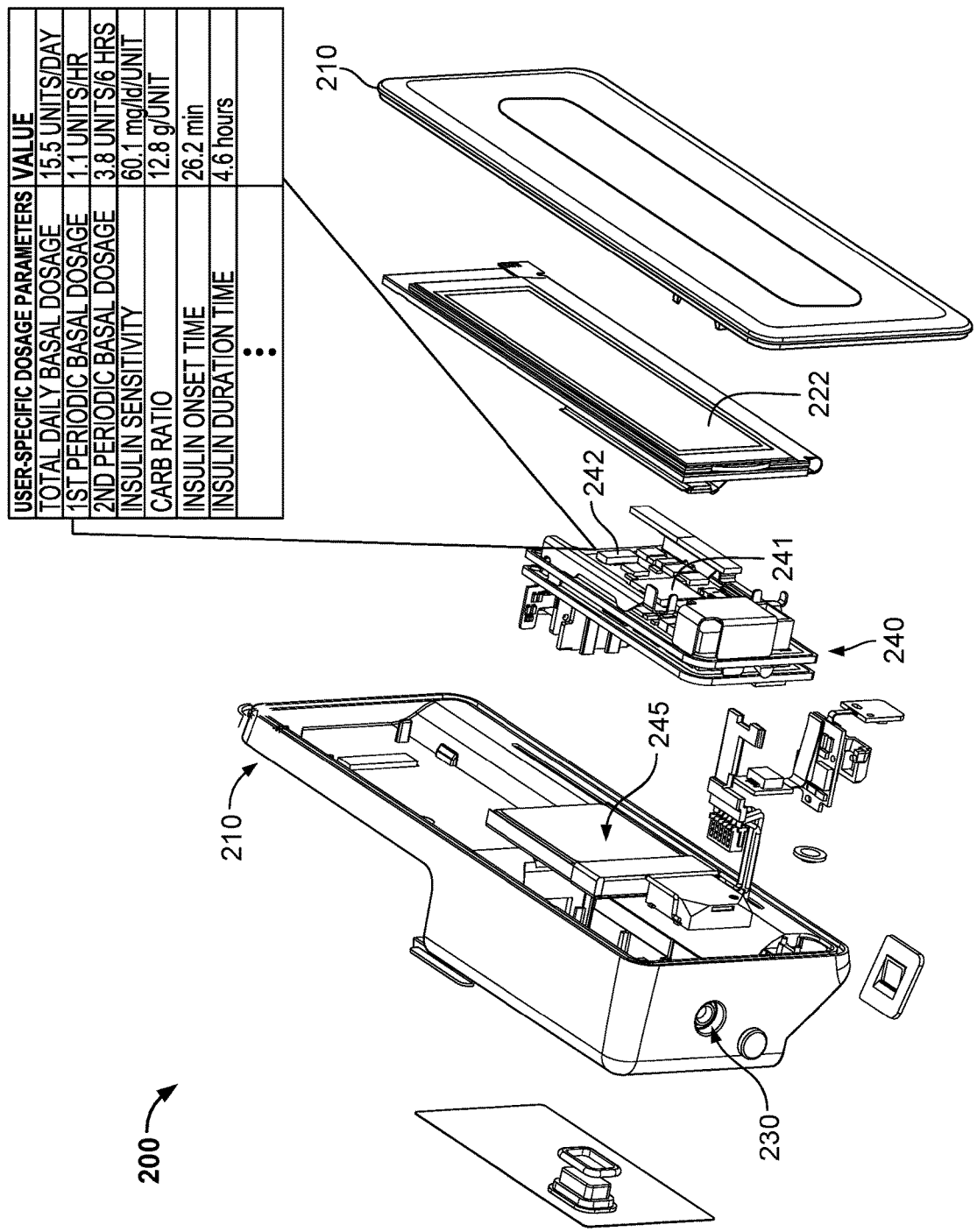
FIG. 6 is an exploded perspective view of an example controller device for a multi-modal medicine delivery system.

Referring now to FIG. 6, the controller device 200 (shown in an exploded view) houses a number of components that can be reused with a series of successive pump devices 100. In particular, the controller device 200 can include control circuitry 240 and a rechargeable battery pack 245, each arranged in the controller housing 210. The rechargeable battery pack 245 may provide electrical energy to components of the control circuitry 240, other components of the controller device (e.g., the display device 222 and other user interface components, sensors, or the like), or to components of the pump device 100. The control circuitry 240 may be configured to communicate control or power signals to the drive system of the pump device 100, or to receive power or feedback signals from the pump device 100.

The control circuitry 240 of the controller device 200 can include one or more microprocessors 241 configured to execute computer-readable instructions stored on one or more memory devices 242 so as to achieve any of the control operations described herein. At least one memory device 242 of the control circuitry may be configured to store a number of user-specific dosage parameters. One or more user-specific dosage parameters may be input by a user via the user interface 220. Further, as described further below in connection with FIG. 7B, various user-specific dosage parameters can be automatically determined and/or updated by control operations implemented by the control circuitry 240 of the controller device 200. For example, the control circuitry 240 can implement a secondary feedback loop to determine and/or update one or more user-specific dosage parameters in parallel with the multi-modal medicine delivery system 10 operating in a closed-loop delivery mode. Whether determined automatically or received via the mobile computing device 60 (or via the user interface 220 of the controller device 200), the control circuitry 240 can cause the memory device 242 to store the user-specific dosage parameters for future use during operations according to multiple delivery modes, such as closed-loop and open-loop delivery modes. Additionally, the control circuitry 240 can cause the controller device 200 to periodically communicate the user-specific dosage parameters to the mobile computing device 60 for future use during operations by the mobile computing device 60 or for subsequent communication to cloud-based computer network.

Such user-specific dosage parameters may include, but are not limited to, one or more of the following: total daily basal dosage limits (e.g., in a maximum number of units/day), various other periodic basal dosage limits (e.g., maximum basal dosage/hour, maximum basal dosage/6 hour period), insulin sensitivity (e.g., in units of mg/dL/insulin unit), carbohydrate ratio (e.g., in units of g/insulin unit), insulin onset time (e.g., in units of minutes and/or seconds), insulin on board duration (e.g., in units of minutes and/or seconds), and basal rate profile (e.g., an average basal rate or one or more segments of a basal rate profile expressed in units of insulin unit/hour). Also, the control circuitry 240 can cause the memory device 242 to store (and can cause the controller device 200 to periodically communicate out to the mobile computing device 60) any of the following parameters derived from the historical pump usage information: dosage logs, average total daily dose, average total basal dose per day, average total bolus dose per day, a ratio of correction bolus amount per day to food bolus amount per day, amount of correction boluses per day, a ratio of a correction bolus amount per day to the average total daily dose, a ratio of the average total basal dose to the average total bolus dose, average maximum bolus per day, and a frequency of cannula and tube primes per day. To the extent these aforementioned dosage parameters or historical parameters are not stored in the memory device 242, the control circuitry 240 can be configured to calculate any of these aforementioned dosage parameters or historical parameters from other data stored in the memory device 242 or otherwise input via communication with the mobile computing device 60.

As previously described, the user interface 220 of the controller device 200 may optionally include input components and/or output components that are electrically connected to the control circuitry 240. For example, the user interface 220 can include the display device 222 having an active area that outputs information to a user, and the mobile computing device 60 may provide a more full-featured user interface for purposes of receiving user input (which is then communicated to the controller device 200 via the wireless communication connection) and providing more detailed information displays. For example, as described in more detail below, the user may view and interact with the user interface of the mobile computing device 60 (e.g., an interface of the mobile app configured to work with the pump assembly 15) to shuffle through a number of menus or program screens that show particular operational modes (e.g., closed-loop delivery mode and open-loop delivery mode), settings (e.g., user-specific dosage parameters) and data (e.g., review data that shows the medicine dispensing rate, the total amount of medicine dispensed in a given time period, the amount of medicine scheduled to be dispensed at a particular time or date, the approximate amount of medicine remaining in the fluid cartridge 120, or the like). Here, the display device 222 of the controller device 200, the display device of the mobile computing device 60, or both can be used to communicate a number of settings (e.g., user-specific dosage parameters) or menu options (e.g., options for switching between closed-loop and open-loop delivery modes) for the multi-modal medicine delivery system 10. In some cases, the control circuitry 240 can receive input data or other information from the mobile computing device 60 (e.g., via user input at the mobile computing device 60) and thereby cause the controller device 200 to output information to the mobile computing device 60 for display on the screen of the mobile computing device 60, such as settings and data (e.g., review data that shows the medicine dispensing rate, the total amount of medicine dispensed in a given time period, the amount of medicine scheduled to be dispensed at a particular time or date, the approximate amount of medicine remaining the fluid cartridge 120, the amount of battery life remaining, or the like). Additionally or alternatively, the control circuitry 240 can receive input data or other information from the mobile computing device 60 (e.g., via user input at the mobile computing device 60) and thereby cause the display device 222 to output show particular settings and data (e.g., review data that shows the medicine dispensing rate, the total amount of medicine dispensed in a given time period, the amount of medicine scheduled to be dispensed at a particular time or date, the approximate amount of medicine remaining the fluid cartridge 120, the amount of battery life remaining, or the like). The control circuitry 240 can be programmable to cause the control circuitry 240 to change any one of a number of settings or modes of operation for the multi-modal medicine delivery system 10. In some cases, the control circuitry 240 can include a cable connector (e.g., a USB connection port or another data cable port) that is accessible on an external portion of the controller housing 210. As such, a cable can be connected to the control circuitry 240 to upload or download data or program settings to the control circuitry.

Figure 7A:
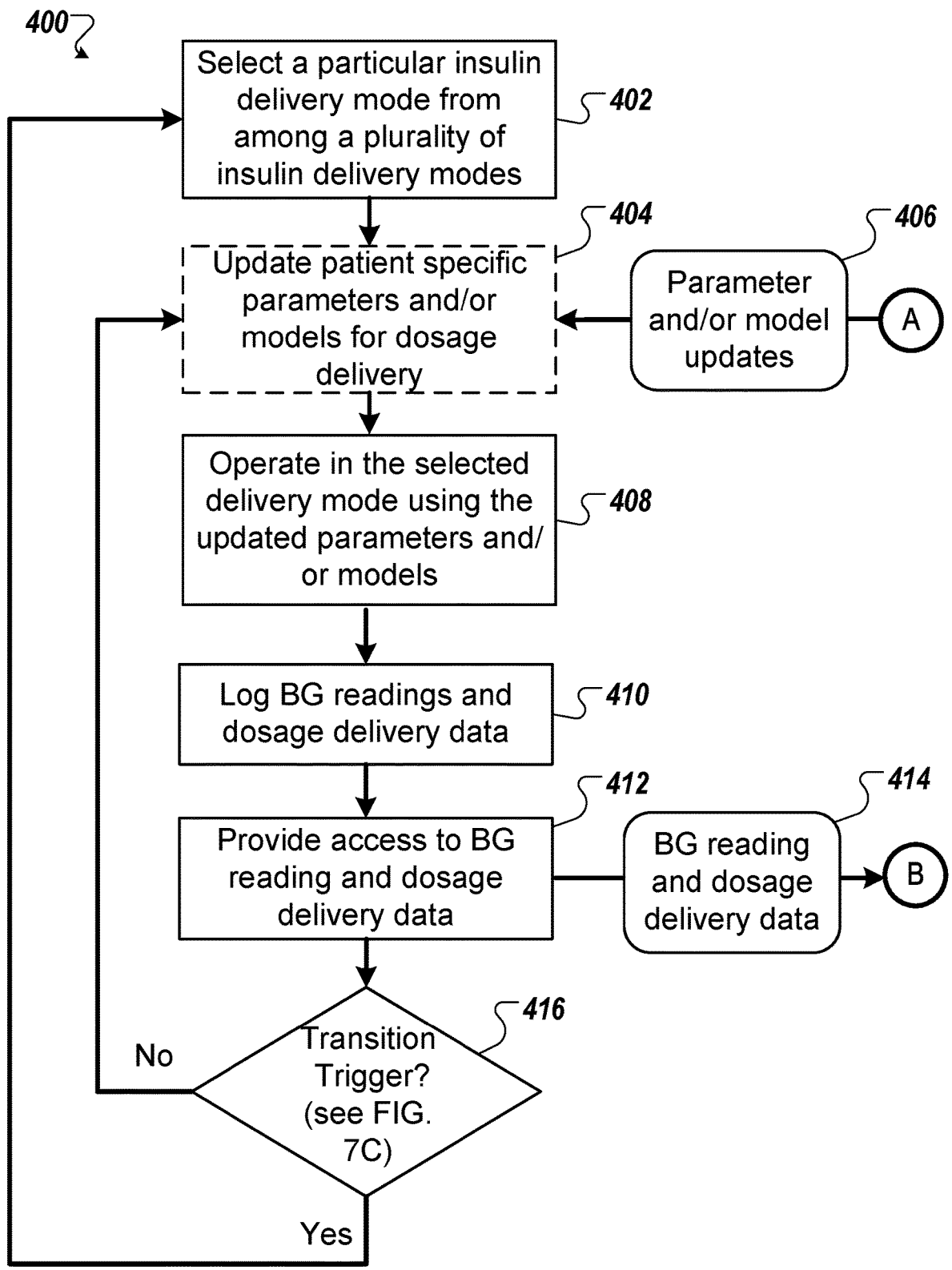
FIG. 7A is a flowchart of an example process for operating a multi-modal medicine delivery system according to multiple dosage delivery modes.
Figure 7B:
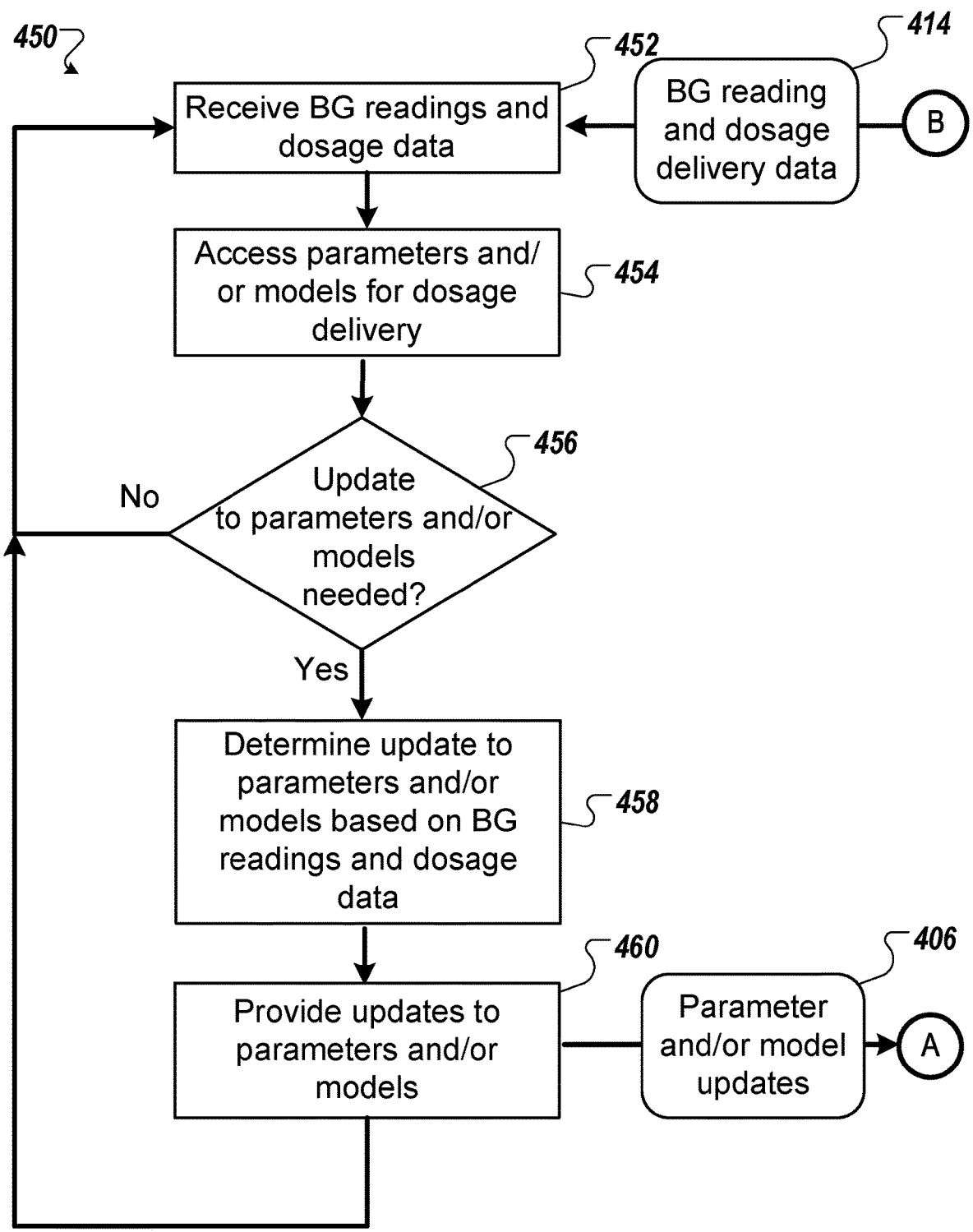
FIG. 7B is a flowchart of an example process for performing a secondary feedback loop to operate a multi-modal medicine delivery system according to multiple dosage delivery modes.
Figure 7C:
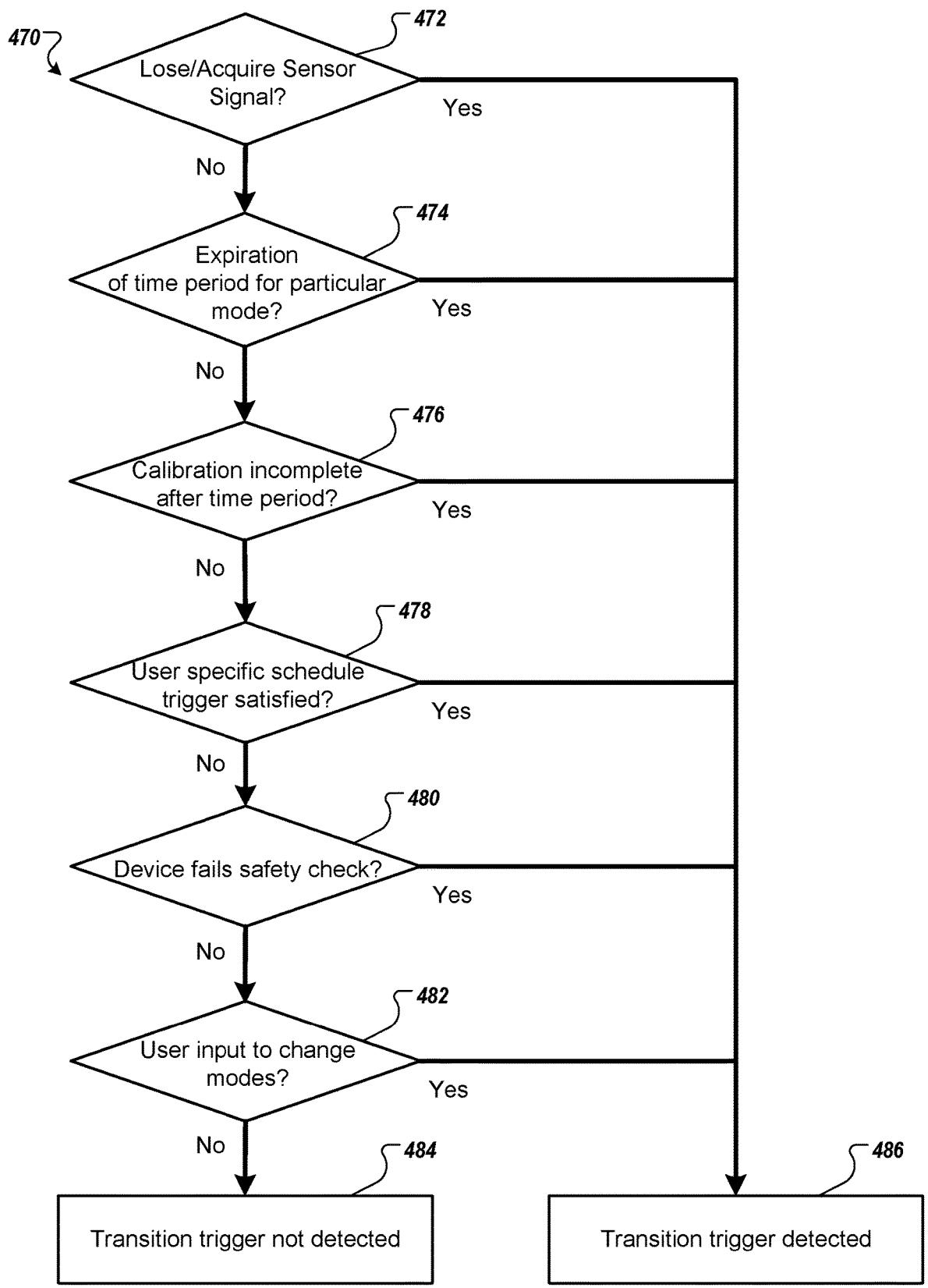
FIG. 7C is a flowchart of an example process for detecting transition triggers between multiple dosage delivery modes for a multi-modal medicine delivery system operating according to multiple dosage delivery modes.

FIGS. 7A-C are flowcharts of example processes 400, 450, and 470 for operating a multi-modal medicine delivery system according to multiple delivery modes and a secondary feedback loop. The example processes 400, 450, and 470 can be examples of the example technique S100-120 described above with regard to FIG. 2. The example process 400, which is depicted in FIG. 7A, selects between multiple delivery modes, obtains information (e.g., updated user-specific dosage parameters, updated user-specific dosage models, user-specific settings) from the secondary feedback loop, operates the multi-modal medicine delivery system according to the selected delivery mode and the information from the secondary feedback loop, and provides data to the secondary feedback loop. The example process 450, which is depicted in FIG. 7B, performs the secondary feedback loop, which includes obtaining data from the process 400, determining/updating information (e.g., updated user-specific dosage parameters, updated user-specific dosage models, user-specific settings) to be used with the process 400 based on the data, and providing the information for use with the process 400. The example process 470, which is depicted in FIG. 7C, evaluates whether one or more of a collection of trigger conditions exist to cause the process 400 to transition between delivery modes.

The processes 400, 450, and/or 470 can be performed by the controller device 200, by the mobile computing device 60, the computing device 5, the DDS 4, the remote computer system 7, the controller device 200, and/or combinations thereof. The processes 400, 450, and/or 470 can be performed by other appropriate computing devices (e.g., remote computer system in communication with the controller device 200 and/or the mobile computing device 60). Such processes 400, 450, and 470, for example, can be implemented by the control circuitry 240 housed in the controller device 200 of an infusion pump assembly 15 (FIGS. 4-6). Performance of the processes 400, 450, and/or 470 (or individual operations within the processes 400, 450, and/or 470) may be split across separate devices of the multi-modal medicine delivery system. For example, in some implementations the controller device 200 can perform the processes 400 and 470, and the mobile computing device 60 can perform the process 450. Other implementations are also possible. The description here is not necessarily limited to any particular multi-modal medicine delivery system with respect to processes 400, 450, and/or 470, and the processes 400, 450, and/or 470 may be implemented using, for example, a multi-modal medicine delivery system in which the control circuitry and drive system components are housed together in a reusable pump unit.

Referring now to FIG. 7A and the process 400, in operation 402 a particular insulin delivery mode can be selected from among a plurality of insulin delivery modes. For example, the controller device 200 and/or the mobile computing device 60 can select from multiple delivery modes, such as a closed-loop delivery mode, an open-loop delivery mode, a learning delivery mode (in which user-specific settings and parameters are learned by the system), and/or other selectable delivery modes. Such a selection of a delivery mode can be based on a variety of factors, such as a previous delivery mode that was being used and a transition trigger that was detected to transition between delivery modes (see, e.g., FIG. 7C). As described below, transition triggers can be automatic and/or manual. For example, the operation 402 can be performed based on an automatically detected transition trigger that is not based on user input, such as a time period associated with a dosage delivery mode expiring, a communication connection with peripheral device (e.g., sensor, the mobile computing device 60) used by the controller device 200 being lost/discovered, and/or calibration of one or more components not being performed within a threshold period of time. In another example, the operation 402 can be performed based on user input selecting a particular dosage delivery mode from a group of dosage delivery modes (e.g., selecting the particular dosage delivery mode from a menu of options). The selection at operations 402 may be performed automatically (e.g., by the controller device 200 and/or the mobile computing device 60 without user input) and/or manually (e.g., based on user input received through a user interface of the controller device 200 and/or through a user interface of the mobile computing device 60).

The plurality of delivery modes can share one or more user-specific parameters and/or models for dosage delivery, which may include: one or more insulin absorption profiles, one or more carbohydrate absorption profiles, a circadian rhythm, one or more mealtimes, one or more insulin to carbohydrate ratios, one or more insulin sensitivity factors, one or more blood glucose levels, one or more temporal factors, one or more diagnostic markers, one or more hormone levels, and/or one or more basal insulin profiles. In some cases, there may be one or more sets of shared parameters and models to the plurality of delivery modes that are applicable to a plurality of different periods in the day, week, month, or year. These multiple sets of parameters and models can result from different insulin and/or medicine requirements based on regular user activities and/or physiologic needs during those time periods.

The delivery mode that is selected may be based on the system's progress toward developing shared parameters and/or models for a specific user. For instance, initially the system may operate in manual delivery modes (e.g., open-loop delivery modes) to obtain data points to be used by a secondary feedback loop to develop shared parameters and/or or models. As more data points are obtained and the variation across the shared parameters and/or models decreases, the system can begin operating under more automated delivery modes (e.g., closed-loop delivery modes). For example, shared parameters and/or models may initially include default values, such as factory presets, and/or they may be manually selected, for example, by a patient's physician, another healthcare professional, or the patient. Through the use of the processes 400 and 450, parameters and models can be generated to more closely match the user's underlying physiology, which can allow the system and the plurality of delivery modes to function more effectively over time.

In operation 404, which may optionally be performed during each iteration of the process 400, an update to patient-specific parameters and/or models for dosage delivery can be performed. Such an update can be performed in response to updated parameters and/or models 406 being provided from the process 450, which is a secondary feedback loop running in parallel with the process 400. For example, in examples where the controller device 200 is implementing the process 400 and the mobile computing device 60 is implementing the process 450, the operation 404 can be performed in response to the mobile computing device 60 having transmitted the parameter and/or model updates 406 to the controller device 200. By using the two separate processes 400 and 450 running in parallel, the process 400 does not need to be interrupted or pause from its current delivery mode to determine parameter and/or model updates, which can be beneficial to implementing a robust and reliable closed-loop delivery mode.

Additionally, the process 450 can run across and incorporate data from each of the multiple delivery modes that may be implemented by the process 400, which can allow for more accurate and complete dosage parameters and/or models to be implemented.

In operation 408, the control circuitry operates the multi-modal medicine delivery system in the selected delivery mode using the updated parameters and/or models and readings for the user (e.g., blood glucose readings). For example, this can include operating in a closed-loop delivery mode (see, e.g., FIGS. 8A and 8B), an open-loop delivery mode (see, e.g., FIG. 10), and/or other appropriate delivery modes. Operation 408 can include automated delivery of medicine (e.g., delivery medicine by a pump device) and/or manual delivery of medicine (e.g., injection of medicine by a user). In a closed-loop delivery mode, the control circuitry can operate the medical device to autonomously (e.g., without user-interaction) alter the dispensation of medication to a user based upon a sensed physiological condition. For example, if the multi-modal medicine delivery system is dispensing insulin, closed-loop operations facilitated by the control circuitry may cause the multi-modal medicine delivery system to imitate a pancreatic beta cell (see FIG. 8A) so that the insulin dispensation is adjusted according to increases or decreases in the user's blood glucose level. This type of closed-loop control delivery mode can be executed by the control circuitry via any suitable control algorithm (e.g., a proportional-integral-derivative (PID), fuzzy logic, or model predictive control algorithm). Further, in some examples, the control circuitry can facilitate closed-loop operations that are consistent with a test regimen (see FIG. 8B). During such closed-loop operations, the control circuitry can monitor one or more sensor signals indicative of the user's response to the dispensation of medication. The sensory feedback signals can be used to implement a feedback control loop (see FIG. 8A), which can be performed using one or more user-specific dosage parameters and/or dosage models as determined by a secondary feedback loop (see FIG. 7B).

In one or more implementations featuring an insulin-dispensing multi-modal medicine delivery system, suitable feedback signals may include, but are not limited to: physiological signals such as blood glucose data, activity data (e.g., heart rate, EKG heart activity, EMG muscle activity, respiration activity, etc.), blood pressure, and the like, glucagon delivery data, and food intake data. As noted above, in such examples, user-specific dosage parameters may include, but are not limited to: insulin sensitivity (e.g., in units of mg/dL/insulin unit), carbohydrate ratio (e.g., in units of g/insulin unit), insulin onset time (e.g., in units of minutes and/or seconds), insulin on board duration (e.g., in units of minutes and/or seconds), and basal rate profile (e.g., an average basal rate or one or more segments of a basal rate profile expressed in units of insulin unit/hour).

In an open-loop delivery mode (see, e.g., FIG. 10), the control circuitry operates the medical device based on the user-specific dosage parameters that can be determined, at least in part, from the secondary feedback loop (process 450). In the open-loop delivery mode, the control circuitry can operate the multi-modal medicine delivery system to dispense medication according to a selected basal delivery pattern and according to user-initiated bolus deliveries. For example, the user may manually input food intake data or blood glucose data and the control circuitry may calculate a suggested bolus dosage of insulin in response. As another example, the control circuitry may monitor a continuous glucose sensor on the user and provide an alert to the user when his/her blood glucose level suggests that a correction bolus dosage is needed. In some cases, the suggested bolus dosage is calculated based on the user-specific dosage parameters that were determined (and stored in the memory) as part of the secondary feedback loop (process 450).

Any of a variety of appropriate techniques can be used to determine and deliver dosages for the selected delivery mode. For example, appropriate dosages can be determined using one or more of: a proportional controller algorithm, a proportional-integral controller algorithm, a proportional-derivative controller algorithm, and a proportional-integral-derivative controller algorithm. Controller algorithms can determine a variety of factors based on, for example, a current rate of change, such as the present error, the accumulation of past or previous errors, and/or a prediction of future errors. Such control algorithms may, in some cases, use additional inputs and/or factors to account for insulin-on-board (e.g., insulin that has been dosed but has yet to act on the user's blood glucose level).

In another example, determining and delivering dosages for the selected delivery mode can use one or more model predictive control (MPC) algorithms. MPC algorithms can be based upon physiologic models of any of a variety of appropriate factors, such as insulin transport, glucose transport, glucagon transport, and other medicine or hormone physiology. MPC algorithms can optimize control actions to minimize the variation of future glucose values to one or more predetermined sets of optimal glucose values. MPC algorithms can be fine-tuned for a specific user by repeatedly optimizing and refining control actions at each iteration of the selected delivery mode.

In operation 410, blood glucose readings and/or dosage delivery data are logged. For example, the controller device 200 can log blood glucose readings that are obtained from the glucose monitoring device 50 and/or blood glucose meter 70, and can log dosages (e.g., timing, quantity, type (e.g., glucagon, insulin, other medicine) that are delivered automatically by the pump assembly 15 using the infusion set 146 and/or manually using the bolus administering device 80. Additional data can also be logged as part of operation 410, such as details about a user's meals (e.g., timing, size, quantity of carbohydrates), activity information (e.g., timing, intensity), a desired aversion to hypoglycemia, a target basal profile, temporal input from the user, one or more hormone levels of the user, insulin absorption profiles, carbohydrate absorption profiles, circadian rhythm for the user, insulin to carbohydrate ratios, insulin sensitivity factors, diagnostic markers, and/or any other type of appropriate information.

In operation 412, the access to the logged blood glucose readings and dosage delivery data 414 can be provided to the process 450. For example, if the processes 400 and 450 are being implemented by separate devices (e.g., process 400 is being implemented by the controller device 200 and process 450 is being implemented by the mobile computing device 60), access can be provided by transmitting the data 414 to the device implementing the process 450. If the processes 400 and 450 are being implemented on the same computing device (e.g., both processes 400 and 450 being implemented by the controller device 200, both processes 400 and 450 being implemented by the mobile computing device 60), access can be provided by, for example, setting appropriate permissions for the data to be accessed by both processes and causing an event to be provided to the processes 450 regarding the availability of the data.

Figure 9:
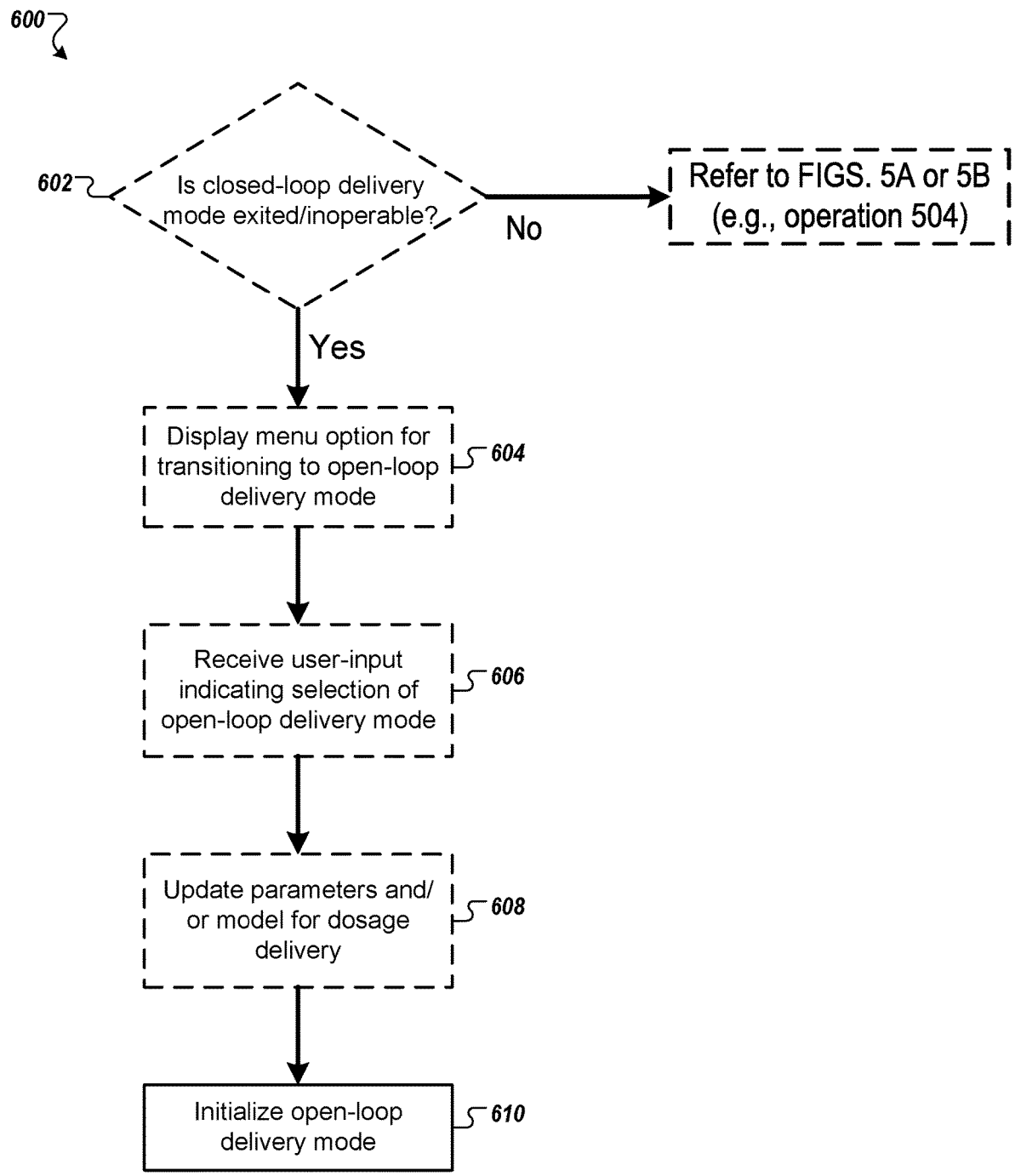
FIG. 9 is a flow chart of an example process for operating a multi-modal medicine delivery system to transition between a closed-loop delivery mode and an open-loop delivery mode.

In operation 416, a determination can be made as to whether a transition trigger has been detected that signals a transition between delivery modes (see, e.g., FIG. 7C and FIG. 9). Transition triggers can be automatic (e.g., time-based transition) and/or manual (e.g., user-input to operate in a different mode). For example, the user may access a menu option displayed by the multi-modal medicine delivery system and press a user interface button that triggers the user's requested change from the closed-loop delivery mode to an open-loop delivery mode. In another example, a transition trigger may arise upon expiration of a predetermined time period for operating in the closed-loop delivery mode.

If a transition trigger is not detected at operation 416, then operations 404-412 are repeated as part of the process 400. For example, if the selected delivery mode is a closed-loop delivery mode, the multi-modal medicine delivery system will continue to operate in a closed-loop delivery mode by performing operations 404-416, which includes updating parameters and/or dosage models from the secondary feedback loop of process 450, until a transition trigger is detected.

If a transition trigger is detected at operation 416, then the operation 402 is repeated and another delivery mode from the plurality of insulin delivery modes is selected and the operations 404-416 are repeated until another transition trigger is detected.

The processes 400 and 450 may run at different frequencies and intervals. For example, iterations of the process 400 may occur more frequently than iterations of the process 450, and vice versa.

In one illustrative example, the plurality of delivery modes can include a manual mode, a personalized mode, an adaptive mode, and an advisory mode, each of which can have a different level of automation. For example, the manual mode can be the lowest level of automation (e.g., open-loop delivery mode) while the adaptive mode can be the highest level of automation (e.g., closed-loop delivery mode). As discussed above, the controller device 200 and/or the mobile computing device 60 can automatically transition between delivery modes and can provide notifications when such transitions are happening/have happened, such as through an audible alarm, a tactile alarm, a visible alarm such as a flashing light or a push notification, a text message, an email, an automated voice message, and/or other types of appropriate notifications.

The controller device 200 and/or the mobile computing device 60 can transition the multi-modal medicine delivery system 10 between delivery modes under a variety of circumstances. For example, a transition from a lower mode of automation to a higher mode of automation can occur based on instructions from a user, all of the components used with the higher mode of delivery being available (e.g., glucose monitoring device 50 and blood glucose meter 70 being communicatively coupled to the controller device 200 and/or the mobile computing device 60), and/or there being no outstanding maintenance actions required from the user.

Further, when switching between the modes of operation, the use of shared parameters and models across all delivery modes can allow for seamless control transfer between modes, which may include the control signal not changed abruptly when the delivery modes are switched due to the consistency of the underlying parameters and models used by the various delivery modes.

The example manual delivery mode includes manual configuration of a continuous basal delivery of insulin and one or more bolus doses of insulin by the bolus administering device 80. In some cases, the system 10 can operate in the manual mode when an analyte sensor used by the system 10 is the blood glucose meter 70 and/or when the user designates the manual mode of operation through a user interface (e.g., the user interface 220). In a manual mode of delivery, the controller device 200 collects data about blood glucose levels and one or more basal doses and one or more bolus doses of insulin, which can be based on wirelessly transmitted data from the blood glucose meter 70 and/or the bolus adminstering device 80, and/or based on user input provided to the controller device 200 and/or the mobile computing device 60.

The example advisory mode of delivery can include use of an injection pen (instead of a syringe) through which the basal or bolus doses are automatically tracked and transmitted to the controller device 200 and/or the mobile computing device 60. Further, in the advisory mode, the user may be responsible for calculating and/or delivering recommended basal or bolus dose.

The example personalized mode (e.g., closed-loop delivery mode) can be used, for example, when a continuous glucose monitor (e.g., glucose monitoring device 50) and/or an automated insulin delivery system (e.g., the pump assembly 15 and the infusion set 146) are available. The personalized mode can also be used when the user provides instructions to operate in the personalized delivery mode.

In some cases, the mode of operation can be selected based on any combination of the type of blood glucose sensor that is available to the system 10 (e.g., blood glucose meter (BGM) 70, continuous glucose monitor (CGM) 50) and the type of treatment that is available to the system 10 (e.g., insulin delivery system, pen/syringe). Example scenarios and corresponding delivery modes are depicted in Table 1 below. Other scenarios are also possible, delivery modes of operation being selected based on an injection pen and a CGM being available; a syringe and CGM being available; both a BGM and CGM, and one or more drug delivery systems (e.g., syringe, pen, pump) being available; and two or more types of drug delivery systems and one or more types of analyte sensors (e.g., BGM, CGM) being available.

TABLE 1

| Mode | BG Sensor | Insulin Delivery System | Treatment Decision |
| --- | --- | --- | --- |
| Personal | CGM | Automated insulin delivery system | Automated by multi-modal medicine delivery system |
| Manual | BGM | Automated insulin delivery system | Automated by multi-modal medicine delivery system |
| Advisory | BGM | Pen/syringe | Manual direction user through interface |

Referring now to FIG. 7B, which depicts process 450 as an example secondary feedback loop, in operation 452 the blood glucose reading and dosage deliver data 414 are received. In response to receiving the data 414, in operation 454 the current user-specific parameters and/or models for dosage delivery can be accessed. For example, a device that is performing process 450 (e.g., controller device 200, mobile computing device 60) can maintain user-specific parameters and/or models for dosage delivery, as well as the underlying data and settings used to determine the parameters and/or models. In operation 456, a determination can be made as to whether to update the parameters and/or models that are currently being used as part of the process 400 based, at least in part, on the received data 414 and the current parameters and/or models. An update may be determined to be warranted when the readings and dosage data fall outside of one or more predetermined threshold/target values.

For example, if a blood glucose reading of a user is consistently above or below a target of the user, a basal profile, insulin to carbohydrate ratio, and/or insulin sensitivity factor may be updated so that the user receives more or less insulin, respectively, to more accurately achieve the target or preferred blood glucose level. As another example, if a user consistently eats a meal at 12:00 PM, the underlying parameters and models may be updated to ensure that the user receives an increase in insulin dosing around 12:00 PM and/or a reminder for missed meal notifications shortly after 12:00 PM. In some cases, the logged data may be analyzed for patterns via, for example, machine learning algorithms, so that the underlying parameters and models may be updated to account for the observed pattern(s). As another example, in some cases, the parameters and models may include a range of acceptable basal insulin profiles and a range of acceptable insulin doses and dose frequencies. In such implementations, if the process 400 is repeatedly delivering and/or instructing delivery of doses and dose frequencies at an upper or lower bound of acceptable ranges in order to achieve the target glycemic range, the system may identify that the underlying parameters and models need to be updated so that upper/lower delivery bounds are not constraining delivery as part of the process 400.

If at the operation 456 it is determined that the update is not warranted, the process 450 repeats operations 452-456. If, in contrast, it is determined that an update is warranted, then an update to the parameters and/or models based, at least in part, on the data 414 and the current parameters and/or models can be determined at operation 458. In some cases, user-specific dosage parameters (e.g., insulin sensitivity, carbohydrate ratio, insulin onset time, insulin on board duration, and basal rate profile) can be determined as a function time and/or as a function of a monitored sensory feedback signal. For instance, the user-specific dosage parameters can be determined and/or updated based on historical sensory feedback data (e.g., historical blood glucose data) and historical pump-usage data generated during the closed-loop delivery operations. As one non-limiting example, a series of multiple insulin sensitivities can be determined based on the time of day and/or based on the user's blood glucose level. The user-specific dosage parameters can be determined using any suitable mathematical technique. For example, in some cases, the control circuitry may employ a predefined data model (e.g., an empirical or statistical model expressed in an algebraic formula) and/or a regression analysis (e.g., a single or multi-variable regression analysis) to determine the parameters. As one example, a regression analysis approximating the relationship between the correction dosage (refer to operation 516, described below) and blood glucose level can be used to determine an insulin sensitivity parameter that is specific to the user (because various users will respond differently to correction dosages of insulin). The scope of the present disclosure is not limited to any particular process, algorithm, or technique for determining the various user-specific dosage parameters and/or models described herein.

In some cases, the updating of one or more of the shared parameters and models may be limited by a pre-determined range of permissible values. In such cases, the user-specific parameters and/or models can only be updated automatically within the pre-determined range of values. In such cases, if the parameters and/or models warrant updating beyond or outside of the pre-determined range of values, an alert or notification may be sent to one or more entities/people who are authorized to approve such deviations, like a patient's physician or other authorized health professional. Such authorization can include providing an appropriate entity with background information on the patient's condition, such as patient data obtained by the system 10, current user-specific parameters and/or models, and recommended modifications outside of the predefined ranges.

In operation 460, updated parameters and/or models 406 can be provided/made available to the process 400, which may include transmitting the updated information 406 and/or otherwise making it accessible to the process 400 (e.g., setting appropriate file permissions, triggering event notifications). After providing the updates, the process 450 can repeat operation 452, which can allow the process 450 to continually refine the user-specific dosage parameter and/or models that are used across the plurality of delivery modes that are implemented in the process 400.

Referring now to FIG. 7C, the process 470 is performed as part of operation 416 of process 400 to determine whether transitioning to a different delivery mode is appropriate. At operation 472, a determination is made as to whether a signal for a sensor (or other system component) has been lost or acquired. For example, the system is operating in a closed-loop delivery mode and the wireless signal to the glucose monitoring device 50 is lost, the system can automatically determine that a transition trigger (to transition to an open-loop delivery mode) has been detected at operation 486. Conversely, if the system is operating is subsequently operating in an open-loop delivery mode and the signal for the glucose monitoring device 50 is reacquired, then the system can automatically determine that a transition trigger (to move back to a closed-loop delivery mode) has been detected at operation 486. The loss and/or acquisition of signals for any of the components within the system 10, such as the mobile computing device 60, the blood glucose meter 70, the glucose monitoring device 50, the pump 100, the bolus administering device 80, and/or other appropriate devices, may cause the trigger condition at operation 472 to be satisfied.

At operation 474, a determination is made as to whether a time period for a particular delivery mode has expired. For example, a closed-loop delivery mode may have an expiration time period of 2 hours, 6 hour, 12 hours, 24 hours, or other appropriate timeframes after which the system 10 automatically transitions out of the closed-loop delivery mode. If the time period corresponding to the selected delivery mode from process 400 has expired, then the transition trigger has been detected at operation 486. The time periods for delivery modes may be user-specific and can be one of the parameters that are determined as part of process 450.

At operation 476, a determination is made as to whether one or more calibrations have been successfully completed after a period of time. For example, the multi-modal medicine delivery system 10 may require a patient or technician to perform system and/or component calibrations with regular intervals (e.g., calibrate all system components every month, every 6 months, every year) to ensure proper operation of the system. Failure to complete one or more identified/recommended calibrations within specified timeframes can be a trigger condition to transition to another delivery mode at operation 486.

At operation 478, a determination is made as to whether one or more user-specific scheduled transitions between delivery modes has occurred. For example, a user can specify that the multi-modal medicine delivery system 10 should operate in a closed-loop mode in the evenings and overnight, and then transition to an open-loop delivery mode at 8:00 am. Schedules can be based on any of a variety of appropriate time-based units, such as time of the day, days of the week, particular scheduled activities/events, and/or other appropriate factors. When the scheduled transition point has been reached between modes of operation, the transition trigger can be detected at operation 486.

At operation 480, a determination can be made as to whether the device has failed one or more safety checks to continue operating with at least a threshold level of reliability. Such safety checks can include evaluating whether any system components require replacement (e.g., component has reached end of useful life, updated model available). Such safety checks can also involve evaluating whether the power sources for various system components are sufficient for at least a threshold period of time (e.g., sufficient charge to operate for 1 hour more, 2 hours more, 4 hours more, 6 hours more). Additional safety checks can include evaluating whether one or more system components (e.g., the mobile computing device 60 and/or controller device 200) need a software/firmware update or an upgrade, and/or the cartridge 120 has less than a threshold amount of medicine remaining and needs to be refilled. If the device is determined to fail one or more safety checks, then a transition trigger can be detected at operation 486.

At operation 482, a determination can be made as to whether user input to change modes of operation has been received. Such user input can be received through one or more user interfaces provided by various components of the multi-modal medicine delivery system 10, such as the controller device 200 and/or the mobile computing device 60. In response to determining that the user has requested that the delivery mode change, the transition trigger can be detected at operation 486. If no transition triggers have been detected, then the no transition trigger operation 484 is performed.

Figure 8A:
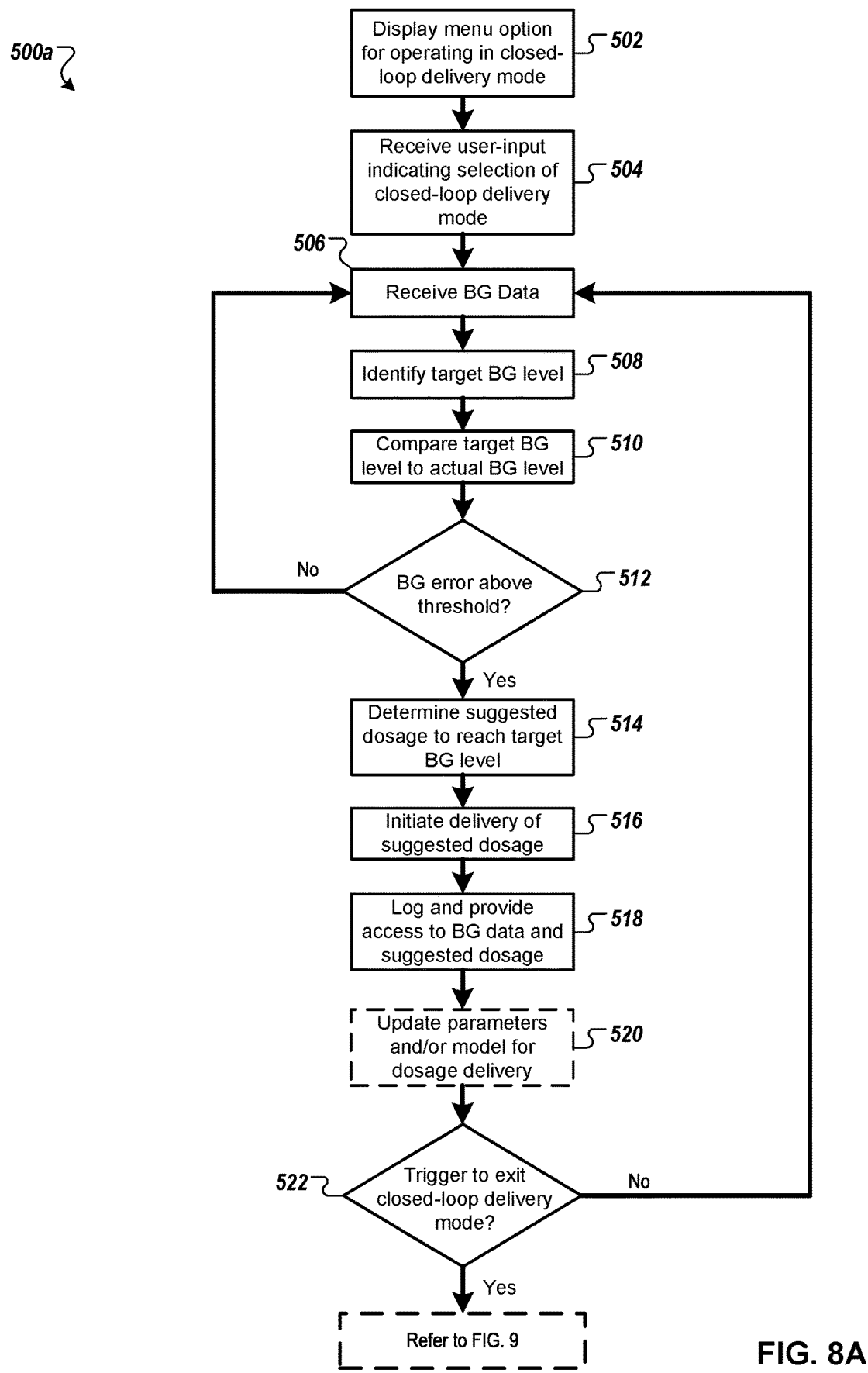
FIG. 8A is a flowchart of a first example process for operating a multi-modal medicine delivery system in a closed-loop delivery mode.

FIG. 8A depicts a first example process 500a executable by the controller device 200 and/or the mobile computing device 60 for operating the multi-modal medicine delivery system 10 in a closed-loop delivery mode to determine one or more user-specific dosage parameters. In operation 502, the mobile computing device 60 or the controller device 200 causes a menu option for operating in a closed-loop delivery mode to be displayed to the user via the user interface of the respective device (see FIGS. 4-5). The user can accept or decline the option by selecting the appropriate user-interface button (e.g., a virtual button on the display of the mobile computing device 60 or a button on the controller device 200). In operation 504, the mobile computing device 60 or the controller device 200 can receive user-input indicating selection of the closed-loop delivery mode. Additionally and/or alternatively, the controller device 200 and/or the mobile computing device 60 can automatically transition into the process 500a based on one or more of the trigger conditions 472-480 being met.

In operation 506, the controller device 200 initiates an iterative sequence of operations that facilitate the closed-loop delivery of medication (e.g., insulin) by receiving blood glucose data. As described above, blood glucose data can be received from a glucose monitoring device 50 in wireless communication with the pump assembly 15 (or received from a blood glucose test strip reader). In operation 508, the controller device 200 identifies a target blood glucose level. For example, one or more target blood glucose levels may be stored in memory device 242 of the control circuitry 240. The target blood glucose levels may correspond to one or more monitored sensory feedback signals. For instance, the target blood glucose level may vary according to the user's food intake and/or physiological status. As one example, the member device 242 stores data indicating at least a fasting target blood glucose level and a postprandial target blood glucose level. In some cases, a target blood glucose level can be expressed as a range. In some cases, the target blood glucose levels can be manually submitted to the controller device 200 via the user interface 220, to the mobile computing device 60, and/or to other appropriate devices. In some cases, the target blood glucose levels can be determined statistically or empirically by the controller device 200 and/or the mobile computing device 60, such as by the process 450 implementing a secondary feedback loop, as a user-specific dosage parameter based on previous iterations of a closed-loop delivery scheme. In operation 510, the controller device 200 and/or the mobile computing device 60 compares the user's actual blood glucose level (as indicated by the received blood glucose data) to the identified target blood glucose level to ascertain a blood glucose error. In operation 512, the controller device determines whether the blood glucose error is above a predetermined threshold. In operation 514, if the controller device 200 and/or the mobile computing device 60 concludes that the actual blood glucose error is above a predetermined threshold (operation 512), a correction dosage to correct the blood glucose error is determined. Otherwise (512), the controller device 200 and/or the mobile computing device 60 returns to operation 506 to await the receipt of further blood glucose data. In some cases, the correction dosage is determined via suitable PID control calculations, fuzzy logic control calculations, and/or model predictive control calculations. In operation 516, the controller device 200 and/or the mobile computing device 60 initiates delivery of the correction dosage. For example, as described above, the controller device 200 and/or the mobile computing device 60 can issue one or more electronic control signals to the drive system of the pump device 100 to cause the dispensation of the correction bolus.

In operation 518, the controller device 200 and/or the mobile computing device 60 can log the detected blood glucose levels and information related to dosage delivery, such as determined correction dosages and times at which the dosages are delivered. The controller device 200 and/or the mobile computing device 60 can provide access to the logged data, which can include transmitting the data to another device that is performing a secondary feedback loop (e.g., process 450) and/or making the data available to the process 450 implementing the secondary feedback loop (e.g., setting data permissions, sending event notifications to the process 450). In operation 520, in some iterations of the process 500*a*, updated dosage parameters and/or models specific to the user are received and used within for closed-loop delivery mode (process 500*a*). For example, the process 450 can generate and provide updated dosage parameters and/or models specific to a user as part of a secondary feedback loop, which can be received at operation 520.

In operation 522, the controller device 200 and/or the mobile computing device 60 can detect a trigger to exit the closed-loop delivery mode (see, e.g., FIG. 7C). If the controller device 200 and/or the mobile computing device 60 detects a trigger to exit the closed-loop delivery mode (operation 522), it initiates a transition sequence (see FIG. 9). Otherwise (522), the controller device 200 and/or the mobile computing device 60 returns to operation 506 to await the receipt of further blood glucose data (and operations under the closed-loop delivery mode).

Figure 8B:
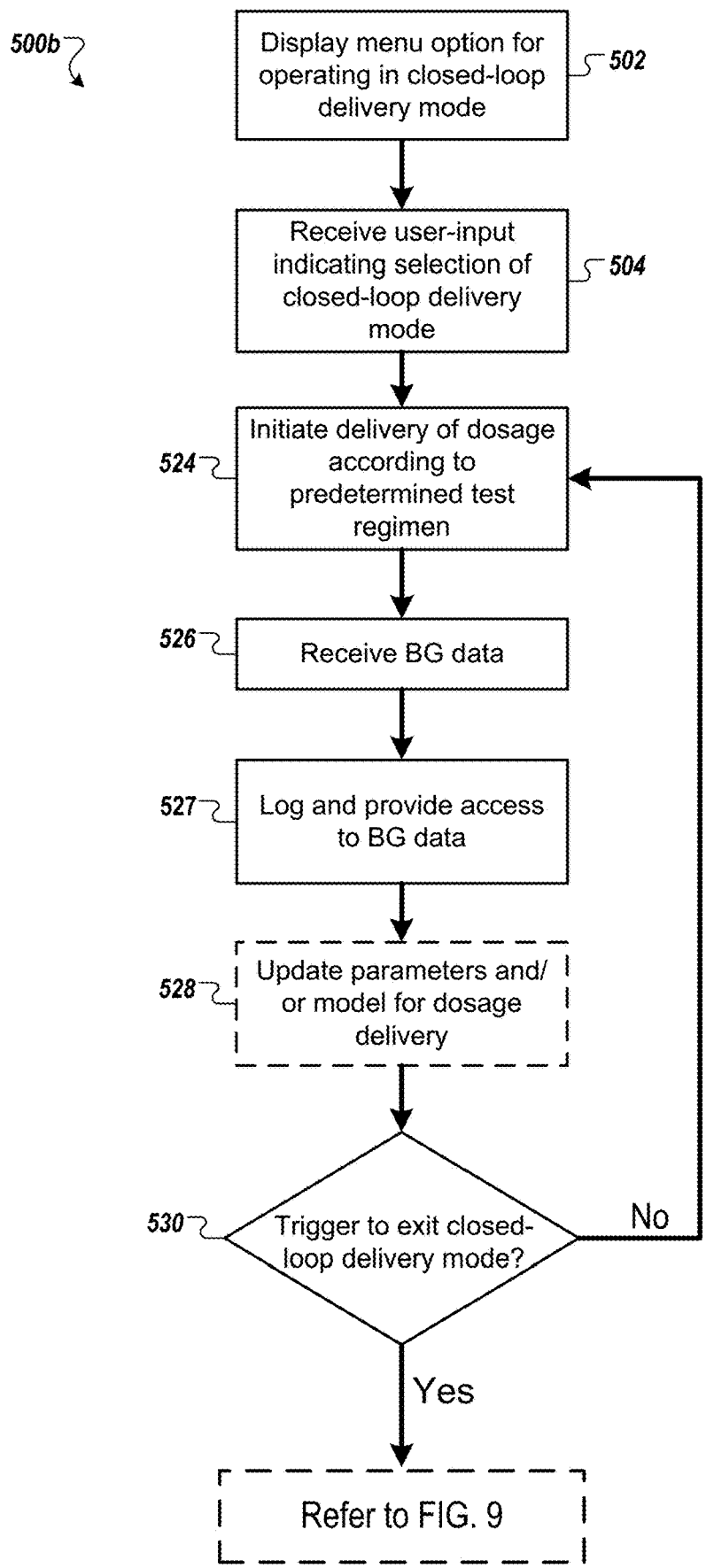
FIG. 8B is a flowchart of a second example process for operating a multi-modal medicine delivery system in a closed-loop delivery mode.

FIG. 8B depicts a second example process 500*b* executable by the controller device 200 and/or the mobile computing device 60 for operating the multi-modal medicine delivery system 10 in a closed-loop delivery mode to determine one or more user-specific dosage parameters. Similar to the first example process 500*a* of FIG. 8A, in operation 502, a menu option for operating in a closed-loop delivery mode is displayed to the user via the display device 222 (see FIGS. 4-5). The user can accept or decline the option by selecting the appropriate user-interface buttons 224. In operation 504, the controller device 200 receives user-input indicating selection of the closed-loop delivery mode (e.g., the user can select the user interface button 224 corresponding to the "YES" option on the display device 222). Additionally and/or alternatively, the controller device 200 and/or the mobile computing device 60 can automatically transition into the process 500*a* based on one or more of the trigger conditions 472-480 being met.

In operation 524, the controller device 200 and/or the mobile computing device 60 initiates the delivery of at least one medicine dosage (e.g., a predetermined, test bolus of insulin) according to a test regimen. In some cases, the test regimen is designed to produce data that can be used to update or determine one or more user-specific dosage parameters, such as part of the process 450. Accordingly, a suitable test regimen may include a plurality of medicine dosages delivered across a predefined time period. In some cases, the test regimen may include a schedule of two or more dosages delivered at predetermined times. For example, a suitable test regimen may provide for X number of medicine dosages (where X is any non-negative whole number) to be delivered at two-hour intervals across a specified time period (e.g., during a time of day that the user is expected to be sleeping or otherwise fasting). In some cases, the test regimen may include a dynamic schedule of two or more dosages. In such cases, the dosage amount and delivery time may vary according to the user's measured bodily response to the medicine. For example, a suitable test regimen may provide for X number of medicine dosages to be delivered across a specified time period when the user's blood glucose level is determined to be at or above a predetermined threshold. Of course, the present disclosure is not limited to these particular example techniques. Any appropriate test regimen involving a planned dispensation of medicine is within the scope of this disclosure.

In operation 526, the controller device 200 and/or the mobile computing device 60 receives blood glucose data. As described above, blood glucose data can be received from a glucose monitoring device 50 in wireless communication with the pump assembly 15 (or received from a blood glucose test strip reader). The blood glucose data received in operation 526 as well as other sensory feedback signals and pump usage data can be stored in a memory device 242 included in the control circuitry 240 of the controller device 200. In operation 527, the controller device 200 and/or the mobile computing device 60 log the blood glucose and dosage data, and provide access to the data for a secondary feedback loop, similar to operation 518.

A secondary feedback loop (e.g., process 450) can determine or updates one or more user-specific dosage parameters (e.g., insulin sensitivity, carbohydrate ratio, insulin onset time, insulin on board duration, and basal rate profile). For example, the controller device 200 and/or mobile computing device 60 may initially calculate the dosage parameters as part of process 450 after one or more iterations of the closed-loop delivery scheme and continue to update the dosage parameters during future iterations. Alternatively, one or more default dosage parameters may be manually input via the user interface 220, and subsequently updated through the process 450 running in parallel with the closed-loop delivery mode (processes 500*a* and 500*b*). In some cases, the controller device 200 and/or the mobile computing device 60 can determine and/or update the user-specific dosage parameters, as part of the process 450, based on historical data (e.g., historical pump data and/or historical sensory feedback data) generated during the test regimen initiated in operation 524. As noted above, the user-specific dosage parameters can be determined using any suitable mathematical technique (e.g., a predefined data model and/or a regression analysis).

In operation 528, in some iteration of the process 500*b* the controller device 200 and/or the mobile computing device 60 can receive and use updated dosage parameters and/or models that have been determined by a secondary feedback loop (e.g., process 450).

In operation 530, the controller device 200 and/or the mobile computing device 60 can detect a trigger to exit the closed-loop delivery mode (see, e.g., FIG. 7C). For example, A transition trigger may arise upon the control circuitry confirming that all dosages of the test regimen (refer to operation 524) have been delivered and the blood glucose data responsive to the test regimen is received. If the controller device 200 and/or the mobile computing device 60 detects a trigger to exit the closed-loop delivery mode (530), it initiates a transition sequence (see FIG. 9). Otherwise (operation 530), the controller device 200 and/or the mobile computing device 60 returns to operation 524 to continue the test regimen.

FIG. 9 depicts an example process 600 executable by the controller device 200 and/or the mobile computing device 60 for operating a multi-modal medicine delivery system to transition between a closed-loop delivery mode and an open-loop delivery mode. In operation 602, the controller device 200 and/or the mobile computing device 60 can determine if the closed-loop delivery mode has been exited (e.g., upon detection of a transition trigger, for example, as described above) or is otherwise inoperable. As one example, the controller device 200 and/or the mobile computing device 60 may determine that a closed-loop delivery mode is completed by confirming that all dosages of a test regimen (see operation 524 of FIG. 8B) have been delivered and the blood glucose data responsive to the test regimen is received. As another example, the controller device 200 and/or the mobile computing device 60 may determine that a closed-loop delivery mode is completed by receiving a trigger signal caused by the user engaging the user interface 220. For instance, the user may interact with the user interface buttons 224 to select on option to terminate the closed-loop delivery mode. As yet another example, the controller device 200 and/or the mobile computing device 60 may determine that the closed-loop delivery mode is inoperable by detecting the disconnecting or malfunctioning of one or more feedback sensors (e.g., the blood glucose monitoring device 50). If the controller device 200 and/or the mobile computing device 60 determines that the closed-loop delivery mode is complete or otherwise inoperable (operation 602), it can display (e.g., via the display device 222 shown in FIGS. 4-5) or otherwise output a menu option for transitioning to an open-loop delivery mode in operation 604. In some cases, the controller device 200 and/or the mobile computing device 60 automatically transition from closed-loop delivery modes to open-loop delivery modes (reference operations 472-480).

In any event, the user can accept or decline the option by selecting the appropriate user-interface buttons 224. In operation 606, the controller device 200 and/or the mobile computing device 60 receives user-input indicating selection of the open-loop delivery mode. For example, the user can select the user interface button 224 corresponding to "YES" on the display screen presenting the menu option. In response to the user's acceptance of the menu option, the controller device 200 and/or the mobile computing device 60 imports (e.g., stores for access during the open-loop delivery mode) the updates to user-specific dosage parameters that were determined by a secondary feedback loop (process 450) in operation 608, and initializes the open loop delivery mode in operation 610.

Figure 10:
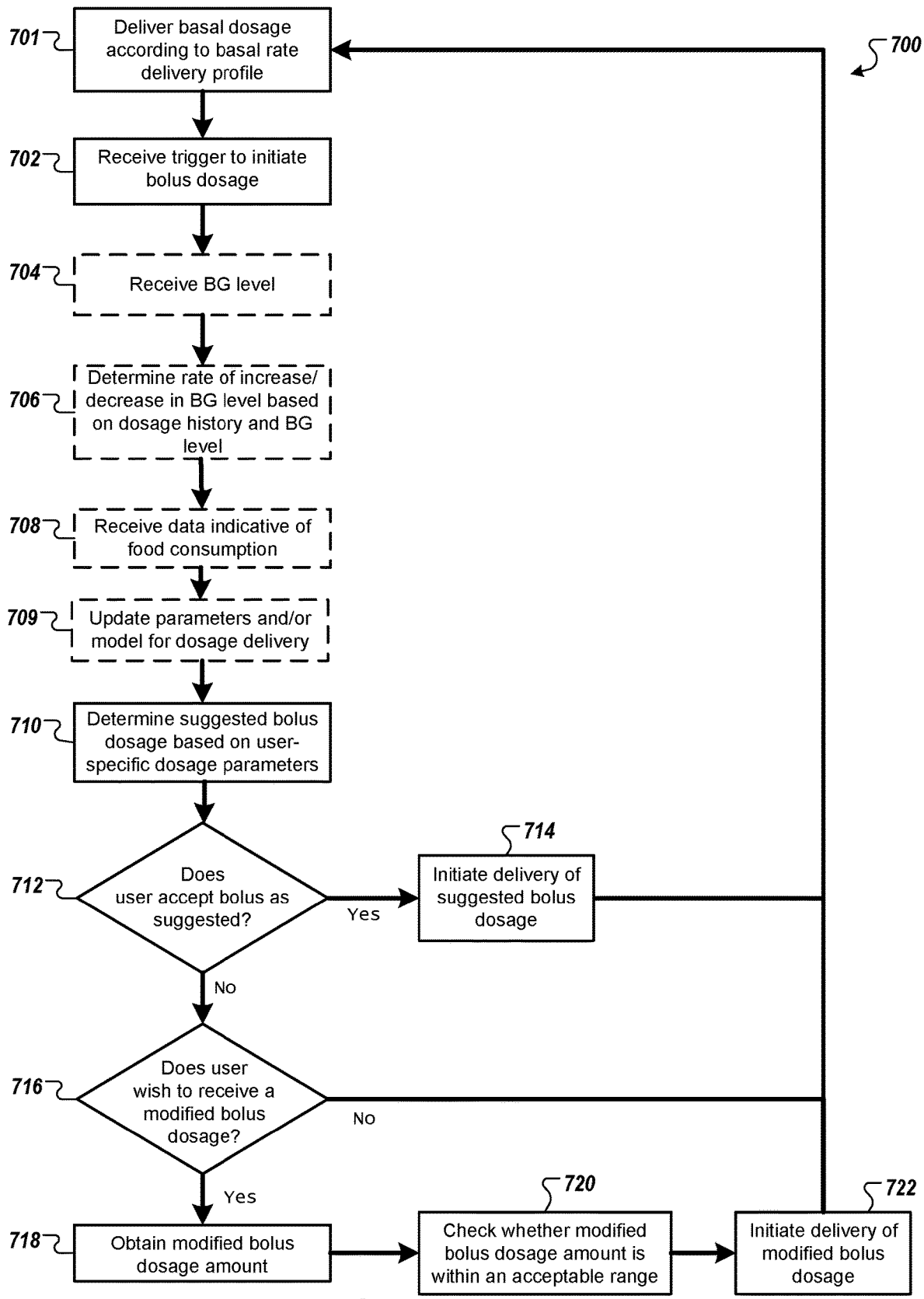
FIG. 10 is a flow chart of an example process for operating a multi-modal medicine delivery system in an open-loop delivery mode.

FIG. 10 depicts a process 700 for operating a multi-modal medicine delivery system in an open-loop delivery mode, where medicine dosages (e.g., bolus dosages of insulin) are calculated in response to a request by the user and/or suggested by the controller device and confirmed by the user. In some cases, the controller device 200 and/or the mobile computing device 60 may implement one or more operations of the process 700 to determine and suggest an insulin bolus dosage, which includes a food offsetting component, a blood glucose correction component, and an insulin load correction component. The food offsetting component can represent an insulin bolus dosage to offset food intake data that have not previously been offset by an earlier bolus dosage. The blood glucose correction component can represent an insulin bolus dosage to maintain or return the user's blood glucose level to a targeted value within a predetermined range. This component can be derived from one or more user-specific dosage parameters (e.g., insulin sensitivity and carbohydrate ratio), data indicative of a user's blood glucose level (e.g., the user's current blood glucose level) and the recent rate of change in the user's blood glucose level. The insulin load correction component can also take into account one or more user-specific dosage parameters (e.g., insulin onset time and insulin on board duration), as well as historical data indicative of insulin that has been previously received and food that has been previously consumed, but has not acted on the user. For example, the delay between a subcutaneous delivery of a bolus dosage of insulin and the peak plasma insulin level achieved from this bolus can be one hour or more. Additionally, the bolus dosage may not enter the subcutaneous tissue all at once. As such, the effect of the bolus can peak at about one to two hours and then decay in a predictable manner over as much as eight hours or. Due to the time decay effects of insulin activity, the user could be susceptible to request a subsequent bolus dosage while some insulin from a previously delivered bolus dosage has not yet acted upon the user (a scenario sometimes referred to as "bolus stacking"). To reduce the likelihood of undesirable bolus stacking, the insulin load information can be determined by the controller device 200 and/or mobile computing device 60 on a periodic basis so that the user can be aware of the previously dispensed insulin which has not yet acted in the user's body. In a similar manner, food that has been previously consumed does not instantaneously act on the user and have its effects quickly decay. Depending on the type of food consumed, the effects of the food can be delayed and then slowly decay over time. In particular implementations, the insulin load correction component may correct for the delayed effects of both previously delivered insulin and previously consumed food items.

Referring in more detail to FIG. 10, in operation 701, the controller device 200 and/or mobile computing device 60 can cause the pump system to dispense basal dosages according to a basal rate delivery profile. The basal rate delivery profile can be stored in the memory of the controller device 200 and/or mobile computing device 60, and can optionally be updated based upon the dosage parameters that are determined as part of a secondary feedback loop (e.g., process 450). In this example, the basal dosages are dispensed in an incremental manner (e.g., dispense 0.25 U every fifteen minutes for a rate of 1.0 U per hour during the period of 8:00 AM to 9:00 PM, and dispense 0.15 U every fifteen minutes for a rate of 0.6 U per hour during the period between 9:00 PM to 8:00 AM) to help maintain the user's blood glucose level within a targeted range during normal activity act selected periods of the day.

In operation 702, the controller device 200 and/or mobile computing device 60 can receive a trigger to initiate a bolus dosage calculation. Exemplary triggers that can cause the controller device 200 and/or mobile computing device 60 to initiate a bolus dosage calculation can include a user input of food intake data (e.g., via the user interface 220), a user request for a bolus dosage, the user's blood glucose level exceeding a predetermined threshold level, the user's blood glucose level increasing at a high rate greater than a predetermined threshold rate, or the like. In some cases, the suggested bolus dosage value can be calculated based on at least two of the three components as previously described: the food offsetting component, the blood glucose correction component, and the insulin load correction component. It should be understood from the description herein that the components can be contemporaneously calculated to provide the suggested bolus dosage value or, alternatively, calculated in discrete steps and then combined to provide the suggested bolus dosage value.

In operation 704, the controller device 200 and/or mobile computing device 60 receives the user's current blood glucose level. As described above, the user's current blood glucose level can be received via wireless communication from the glucose monitoring device 50 (or received from a blood glucose test strip reader, or entered manually by the user via the user interface 220). In operation 706, the controller device 200 and/or mobile computing device 60 can determine a rate of change (e.g., increase or decrease)

based on the dosage history and the blood glucose level. Alternatively, the user may manually enter the rate-of-change information for his or her blood glucose level (rather than this information being determined by the controller device 200 and/or mobile computing device 60). For example, when using a blood glucose test strip reader, the test strip reader may store blood glucose measurements performed by the user, which can be used to determine the rate of change in the user's blood glucose level. When prompted by the controller device 200 and/or mobile computing device 60, the user may enter the most recent rate of change data. In operation 708, the user can optionally enter data indicative of food intake (e.g., a meal that is about to be consumed, a meal that has recently been consumed, or the like). For example, if the user is testing his or her blood glucose level before consuming a meal, the user may input such food intake information when inputting the blood glucose level.

In operation 709, updates to user-specific dosage parameters and/or models can be received and used as part of the process 700. For example, the controller device 200 and/or mobile computing device 60 can perform a secondary feedback loop running in parallel with the process 700 and can determine updates to dosage parameters and/or models based on data from multiple delivery modes (e.g., open-loop delivery mode, closed-loop delivery mode).

After the user's blood glucose information is obtained (e.g., via operations 704-708), in operation 710, the controller device 200 and/or mobile computing device 60 can determined a suggested bolus dosage based on the obtained data and the user-specific dosage parameters that were determined as part of a secondary feedback loop. As noted above, in some cases, the suggested bolus dosage value can be calculated by the controller device 200 and/or mobile computing device 60 based on at least one, but preferably two or more of the three following components: the food offsetting component (which employs the value for the user's carb ratio that was, in this example, calculated during the closed-loop delivery mode), the blood glucose correction component (which employs the value for the user's insulin sensitivity that was, in this example, calculated during the closed-loop delivery mode), and the insulin load correction component. In such implementations, the food offsetting component can represent an insulin bolus dosage to offset food intake data that have not previously been offset by an earlier bolus dosage. The blood glucose correction component can represent an insulin bolus dosage to maintain or return the user's blood glucose level to a targeted value within a predetermined range. The insulin load correction component can take into account insulin that has been previously received and food that has been previously consumed, but has not acted on the user. One non-limiting example is described below:

Suggested Bolus Dosage=(Food Offsetting Component)+(Blood Glucose Correction Component)−(Insulin Load Correction Component), where Food Offsetting Component=(Carbohydrate Intake)*(Insulin to Carb. Ratio), where Carbohydrate Intake represents the number of grams of carbohydrates consumed (or to be consumed) and Insulin to Carb. Ratio represents a user-specific ratio (which was preferably determined and stored during the closed-loop mode during this instance) of the amount of insulin required to offset the consumption of a gram of carbohydrates (e.g., 14.8 U/g or the like).

Blood Glucose Correction Component=(Current Blood Glucose Level−Target Glucose Level)*Insulin Sensitivity, where Current Blood Glucose Level represents the most recent blood glucose level, Target Glucose Level represents the user's desired blood glucose level, Insulin Sensitivity represents a user-specific value (which was preferably determined and stored during the closed-loop mode during this instance) that correlates the number of units of insulin required to alter the user's blood glucose level by 1 mg/dL.

Insulin Load Correction Component=Insulin Load−(Carb. Load)*Insulin to Carb Ratio, where Insulin Load represents the units of previously delivered insulin that have not yet acted on the user, Carb. Load represents the grams of carbohydrates that have been consumed, but have not acted on the user's blood glucose level, and Insulin to Carb. Ratio represents a user-specific ratio (which was preferably determined and stored during the closed-loop mode during this instance) of the amount of insulin required to offset the consumption of a gram of carbohydrates.

In operation 712, the controller device 200 and/or the mobile computing device 60 can determine if the user accepts the suggested bolus dosage. For example, the user can select the user interface button 224 corresponding to the "YES" or "NO" option presented on the display device 222 to accept or decline the suggested bolus dosage. In operation 714, if the accepts the suggested bolus dosage (operation 712), the controller device 200 and/or the mobile computing device 60 can initiate delivery of the suggested bolus dosage by the pump device 100. If the user declines the suggested bolus dosage (operation 712), the controller device 200 and/or the mobile computing device 60 can prompt the user for a modified dosage. In operation 716, the controller device 200 and/or the mobile computing device 60 can determine if the user wishes to receive a modified bolus dosage. In operation 718, if the user wishes to receive a modified bolus dosage (operation 716), the controller device 200 and/or the mobile computing device 60 can obtain the modified bolus dosage. For example, the user can enter a modified bolus dosage or provide additional data that can be used to calculate a modified dosage via the user interface 220. In operation 720, the controller device 200 and/or the mobile computing device 60 can check whether the modified bolus dosage amount is within one or more acceptable ranges. If the modified bolus dosage is outside of one or more acceptable ranges, permission from an authorized person (e.g., physician, heath care professional) may be required before the dosage can be initiated. In operation 720, the controller device 200 and/or the mobile computing device 60 can initiate delivery of the modified bolus dosage by the pump device 100. After a suggested (operation 714) or modified (operation 722) bolus dosage has been initiated, or after the user has declined the suggested (operation 712) and modified dosages (operation 716), the process 700 can return to operation 702, where the controller device 200 and/or the mobile computing device 60 can wait for a subsequent trigger to initiate a bolus dosage calculation.

Figure 11:
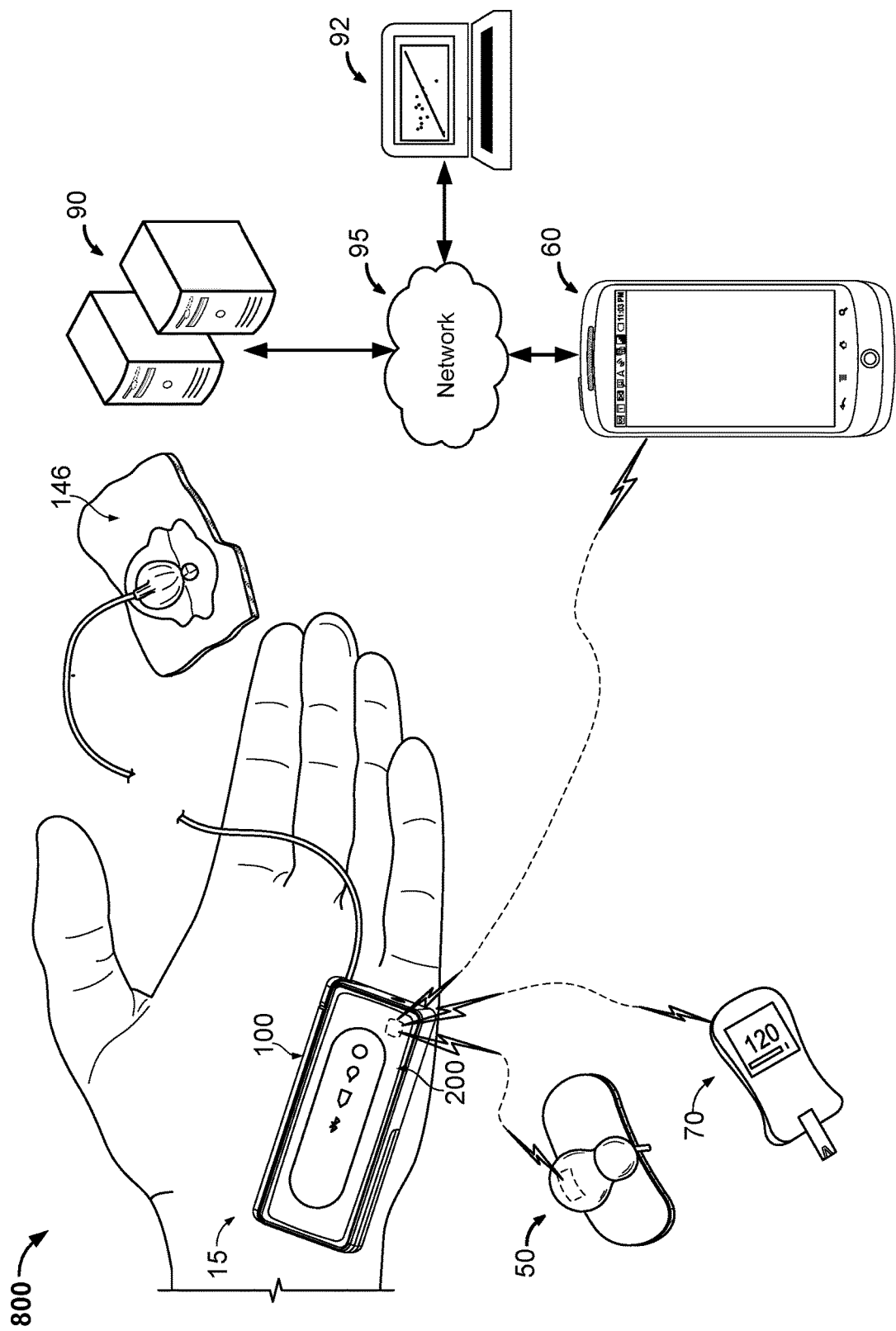
FIG. 11 is a perspective view of another example multi-modal medicine delivery system.

Referring now to FIG. 11, some implementations of a multi-modal medicine delivery system 800 can include a pump assembly 15, featuring a controller device 200 and a pump device 100, mating with an infusion set 146 and a glucose monitoring device 50 (similar to previous implementations described above with reference to FIGS. 4-5). The multi-modal medicine delivery system 800 also includes the mobile computing device 60 or another computing device in wireless communication with the controller device 200 of the pump assembly 15. In general, the term "computing device" refers to any appropriate type of data processing device capable of running operating systems and application programs. Example computing devices can include a general-purpose personal computer (PC), Macintosh, workstation, UNIX-based workstation, a blade server, a handheld computer, a tablet computing device, a personal digital assistant (PDA), a smartphone, or any appropriate combination of any two or more of these data processing devices or other data processing devices. The mobile computing device 60 or other computing device can provide additional processing power to the multi-modal medicine delivery system 800 for executing complex mathematical calculations and algorithms. Thus, the mobile computing device 60 or other computing device can be configured (e.g., appropriately designed and programmed) to execute a suitable program application for determining and/or updating one or more user-specific dosage parameters. As one example, the mobile computing device 60 may determine and/or update one or more user-specific dosage parameters as part of a secondary feedback loop (process 450) based on blood glucose data received from the glucose monitoring device 50 and/or the blood glucose meter 70, and/or pump-usage data received from the controller device 200. The mobile computing device 60 can transmit the user-specific parameters back to the controller device 200 for use in future open-loop and/or closed-loop operations.

The mobile computing device 60 can additionally communicate with local computing device 92, a remote computer system 90, or both over one or more networks 95 to provide the features and functionality described throughout this document. For example, the remote computer system 90 can be a server system (e.g., dedicated computer server, cloud-based computer system, mobile app server system) that is programmed to perform one or more of the processes (or portions thereof) described above, such as the secondary feedback loop (process 450). The network 95 can be any of a variety of appropriate communications networks, such as the internet, wireless networks (e.g., mobile data networks, Wi-Fi networks), local area networks (LANs), wide area networks (WANs), virtual private networks (VPNs), or any combinations thereof.

Figure 12:
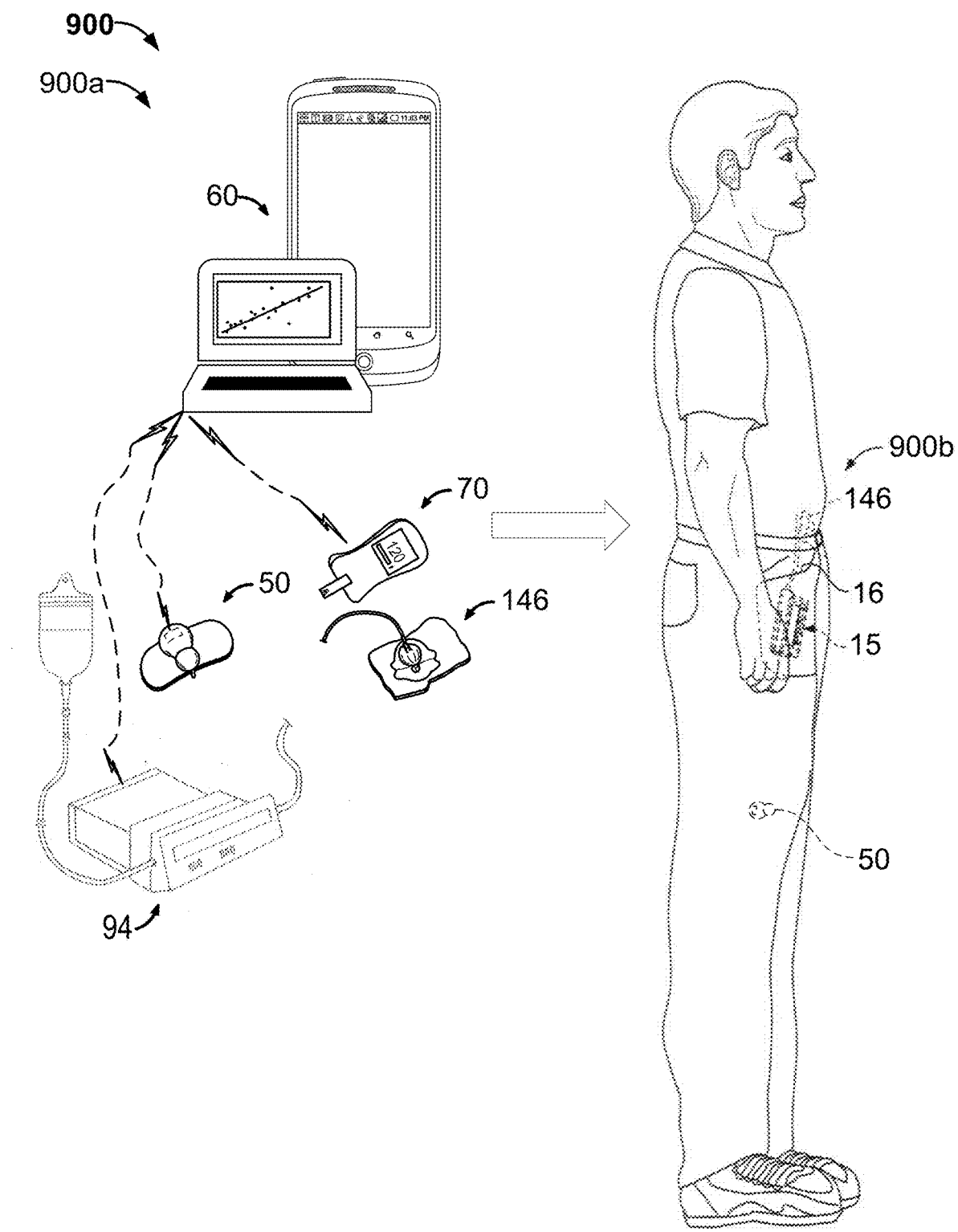
FIG. 12 is a perspective view of another example multi-modal medicine delivery system.

Referring now to FIG. 12, a multi-modal medicine delivery system 900 can include a bedside infusion pump subsystem 900a and a portable infusion pump subsystem 900b. The bedside infusion pump subsystem 900a includes a bedside infusion pump assembly 94 mating with an infusion set 146, a glucose monitoring device 50, a blood glucose meter 70, and a mobile computing device 60. Similar to the previous implementations described above with respect to FIG. 11, the mobile computing device 60 can receive data from the bedside infusion pump assembly 94 and the glucose monitoring device 50 for the purpose of determining one or more user-specific parameters. The portable infusion pump subsystem 900b features a portable pump assembly 15 (see FIGS. 4-5) that is pocket-sized so that the pump device 100 and controller device 200 can be worn in the user's pocket 16 or in another portion of the user's clothing. For example, the pump device 100 and the controller device 200 can be attached together and form the pump assembly 15 that comfortably fits into a user's pocket 16. The user can carry the portable infusion pump assembly 15 and use the tube of an infusion set 146 to direct the dispensed medicine to the desired infusion site. Furthermore, a glucose monitoring device 50 can be worn on the user's skin while the pump assembly 15 is carried by the user (e.g., in a pocket). In some cases, the bedside multi-modal medicine delivery system 900a may be operable to execute operations according to a closed-loop delivery mode (see FIGS. 8A-B) and to use a secondary feedback loop to determine one or more user-specific dosage parameters. The dosage parameters can then be input to the controller device 200 for use in future open-loop and/or closed-loop operations.

A number of implementations have been described. Nevertheless, it will be understood that various modifications may be made without departing from the spirit and scope of the invention. Accordingly, other implementations are within the scope of the following claims.

What is claimed is:

1. A method for delivering one or more medications from a multi-modal medicine delivery system, comprising:

selecting a first delivery mode from among a plurality of delivery modes to use for operating a multi-modal medicine delivery system to dispense one or more medications adapted to alter a blood analyte level;

delivering the one or more medications to a user according to the first delivery mode, the first delivery mode delivering amounts of the one or more medications according to a primary feedback loop that uses analyte sensor data and user-specific dosage parameters to determine at least some of the amounts of the one or more medications to deliver over time without user interaction;

obtaining, while the multi-modal medicine delivery system is operating according to and without exiting the first delivery mode, (i) the analyte sensor data and (ii) one or both of medicine delivery data and food intake data, the analyte sensor data being generated by an analyte sensor and indicating the blood analyte level for the user at one or more specific times, the medicine delivery data identifying amounts and times at which the one or more medications were delivered to the user, the food intake data identifying amounts and times at which one or more foods were consumed by the user;

determining, using a secondary feedback loop, one or more updates to the user-specific dosage parameters based on the analyte sensor data and (ii) the one or both of the medicine delivery data and the food intake data;

delivering the one or more medications to the user according to the first delivery mode using the analyte sensor data and the updated user-specific dosage parameters to determine at least some of the amounts of the one or more medications to deliver over time without user interaction; and switching to a second delivery mode delivering the one or more medications to the user according to the second delivery mode using the updated user-specific dosage parameters to determine a schedule of basal dosages of the one or more medications, and while the multi-modal medicine delivery system is operating according to and without exiting the second delivery mode, performing the following:

obtaining additional analyte sensor data and additional medicine delivery data from operation of the multi-modal medicine delivery system according to the second delivery mode and the updated user-specific dosage parameters;

determining, using the secondary feedback loop, one or more additional updates to the user-specific dosage parameters based on (i) the additional analyte sensor data and (ii) the additional medicine delivery data; and delivering the one or more medications to the user according to the second delivery mode based upon the additional updates to the user-specific dosage parameters.

2. The method of claim 1, wherein the multi-modal medicine delivery system comprises a portable insulin infusion pump system, the analyte sensor data comprises data describing blood glucose readings, and the medicine delivery data identifies insulin dosages delivered to the user from the portable insulin infusion pump system.

3. The method of claim 2, wherein switching to the second delivery mode comprises:
  determining whether to transition out of operating the multi-modal medicine delivery system according to the first delivery mode;
  selecting, in response to a determination to transition out of operating according to the first delivery mode, the second delivery mode to use for operating the multi-modal medicine delivery system from among the plurality of delivery modes; and
  operating the multi-modal medicine delivery system to dispense the one or more medications according to the second delivery mode and the updated user-specific dosage parameters.

4. The method of claim 1, wherein the secondary feedback loop determines the additional updates to the user-specific dosage parameters based on both (i) the analyte sensor data and the medicine delivery data generated during the first delivery mode, and (ii) the additional analyte sensor data and the additional medicine delivery data generated during the second delivery mode.

5. The method of claim 1, wherein detecting a transition trigger event comprises detecting the transition trigger event automatically without user input.

6. The method of claim 1, wherein detecting a transition trigger event comprises detecting a signal to the analyte sensor being lost or acquired.

7. The method of claim 1, wherein detecting a transition trigger event comprises detecting an expiration of a period of time for operating the multi-modal medicine delivery system according to the first delivery mode.

8. The method of claim 1, wherein a transition trigger event comprises detecting that one or more calibrations for one or more components of the multi-modal medicine delivery system has failed to be completed after a period of time.

9. The method of claim 1, wherein detecting a transition trigger event comprises detecting a scheduled transition in a time-based schedule for a patient using the multi-modal medicine delivery system.

10. The method of claim 1, wherein detecting a transition trigger event comprises detecting one or more components of the multi-modal medicine delivery system failing one or more safety checks.

11. The method of claim 1, wherein detecting a transition trigger event comprises detecting a user input to the multi-modal medicine delivery system.

12. The method of claim 1, wherein selecting the first delivery mode from among the plurality of delivery modes comprises:
  selecting the first delivery mode from a group comprising: a closed-loop delivery mode and an open-loop delivery mode, wherein the first delivery mode is a closed-loop delivery mode and the second delivery mode is an open-loop delivery mode.

* * * * *

UNITED STATES PATENT AND TRADEMARK OFFICE
CERTIFICATE OF CORRECTION

Page 1 of 1

PATENT NO. : 10,987,468 B2
APPLICATION NO. : 15/384493
DATED : April 27, 2021
INVENTOR(S) : Bryan Mazlish and Lane Desborough It is certified that error appears in the above-identified patent and that said Letters Patent is hereby corrected as shown below:

In the Specification

| | | |
|---|---|---|
| Column 6, | Line 26, | change "on on" to --on-- |
| Column 11, | Line 56, | change "*8a8-n*" to --*8a-8n*-- |
| Column 14, | Line 10, | change "*8a-n*" to --*8a-8n*-- |
| Column 20, | Line 3, | change "*8a-n*" to --*8a-8n*-- |
| Column 20, | Line 8, | change "*8a-8n*operated" to --*8a* operated-- |
| Column 23, | Line 20, | change "adminstering" to --administering-- |
| Column 23, | Line 33, | change "adminstering" to --administering-- |
| Column 23, | Line 37, | change "adminstering" to --administering-- |
| Column 28, | Line 35, | change "cartridge" to --fluid cartridge-- |
| Column 28, | Line 37, | change "cartridge" to --fluid cartridge-- |
| Column 28, | Line 43, | change "housing" to --pump housing-- |
| Column 38, | Line 36, | change "adminstering" to --administering-- |
| Column 44, | Line 54, | change "(530)" to --(operation 530)-- |
| Column 44, | Line 55, | change "(operation 530)" to --(530)-- |

Signed and Sealed this
Sixth Day of July, 2021

Drew Hirshfeld
*Performing the Functions and Duties of the
Under Secretary of Commerce for Intellectual Property and
Director of the United States Patent and Trademark Office*